US011629190B2

(12) United States Patent
Mourich et al.

(10) Patent No.: US 11,629,190 B2
(45) Date of Patent: Apr. 18, 2023

(54) CANINE ANTIBODY THERAPEUTIC FOR TREATING CANCER

(71) Applicant: Oregon State University, Corvallis, OR (US)

(72) Inventors: Dan Vincent Mourich, Salem, OR (US); Carl E. Ruby, Corvallis, OR (US); Shay Bracha, Corvallis, OR (US); Christopher Keith Cebra, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 420 days.

(21) Appl. No.: 16/992,412

(22) Filed: Aug. 13, 2020

(65) Prior Publication Data

US 2021/0047412 A1 Feb. 18, 2021

Related U.S. Application Data

(60) Provisional application No. 62/887,520, filed on Aug. 15, 2019.

(51) Int. Cl.
*C07K 16/28* (2006.01)
*G01N 33/569* (2006.01)
(Continued)

(52) U.S. Cl.
CPC .... *C07K 16/2818* (2013.01); *A61K 39/39541* (2013.01); *A61K 45/06* (2013.01);
(Continued)

(58) Field of Classification Search
CPC ...................................................... A61P 35/00
See application file for complete search history.

(56) References Cited

U.S. PATENT DOCUMENTS

| 9,605,074 B2 | 3/2017 | Shah |
| 2015/0203579 A1 | 7/2015 | Papadopoulos et al. |
| 2018/0079822 A1 | 3/2018 | Liu et al. |

FOREIGN PATENT DOCUMENTS

| CN | 106029695 A | 10/2016 |
| WO | WO 2015/091911 A2 | 6/2015 |
| WO | WO 2016/020856 A3 | 2/2016 |

OTHER PUBLICATIONS

Bannas et al., "Nanobodies and nanobody-based human heavy chain antibodies as antitumor therapeutics," *Frontiers in Immunology* 8(1603): 13 pages (Nov. 22, 2017).
(Continued)

*Primary Examiner* — Adam Weidner
*Assistant Examiner* — Laura Ann Essex
(74) *Attorney, Agent, or Firm* — Klarquist Sparkman, LLP

(57) ABSTRACT

Disclosed are isolated single heavy chain variable ($V_HH$) monoclonal antibodies, antigen binding fragments thereof, and bispecific antibodies include these $V_HH$ monoclonal antibodies, wherein the $V_HH$ monoclonal antibody or antigen binding fragment specifically binds a canine programmed death (PD)-1. Nucleic acid molecules encoding these $V_HH$ monoclonal antibodies and antigen binding fragments are also disclosed, as are expression vectors including these nucleic acid molecules and host cells including these expression vectors. Methods of detecting canine PD-1, and methods of increasing cytotoxic T cell activity and treating tumors are also disclosed.

20 Claims, 6 Drawing Sheets

Specification includes a Sequence Listing.

(51) Int. Cl.
  *A61K 39/395*  (2006.01)
  *A61K 45/06*  (2006.01)
  *A61P 35/00*  (2006.01)
  *A61K 39/00*  (2006.01)

(52) U.S. Cl.
  CPC ........ *A61P 35/00* (2018.01); *G01N 33/56972* (2013.01); *A61K 2039/505* (2013.01); *C07K 2317/35* (2013.01); *C07K 2317/565* (2013.01); *C07K 2317/567* (2013.01); *C07K 2317/569* (2013.01); *C07K 2317/76* (2013.01); *C07K 2317/92* (2013.01); *G01N 2333/70503* (2013.01)

(56) References Cited

OTHER PUBLICATIONS

Choi et al., "PD-1/PD-L1 monoclonal antibody development for canine cancer therapy," *Journal of Immunology* 200(1 Supplement): 59.28; (May 1, 2018).

Mazzega and de Marco, "Engineered cross-reacting nanobodies simplify comparative oncology between humans and dogs," *Vet Comp Oncol* 16(1): E202-E206 (Epub 2017 Oct. 18, 2017).

Nemoto et al., "Development and characterization of monoclonal antibodies against canine PD-1 and PD-L1," *Vet Immunology Immunopathology* 198: 19-25 (Apr. 2018).

FIG. 2

| NANOBODY | Kd [M] | [50% inhibition (M)] |
|---|---|---|
| 1B5 | $0.95 \times 10^{-9}$ | $9.4 \times 10^{-9}$ |
| 4B4 | $2.30 \times 10^{-9}$ | $5.04 \times 10^{-9}$ |
| 4B2 | $2.51 \times 10^{-9}$ | $5.0 \times 10^{-9}$ |
| 5A5 | $5.01 \times 10^{-9}$ | $6.83 \times 10^{-9}$ |
| 5A1 | $7.00 \times 10^{-9}$ | $8.25 \times 10^{-9}$ |

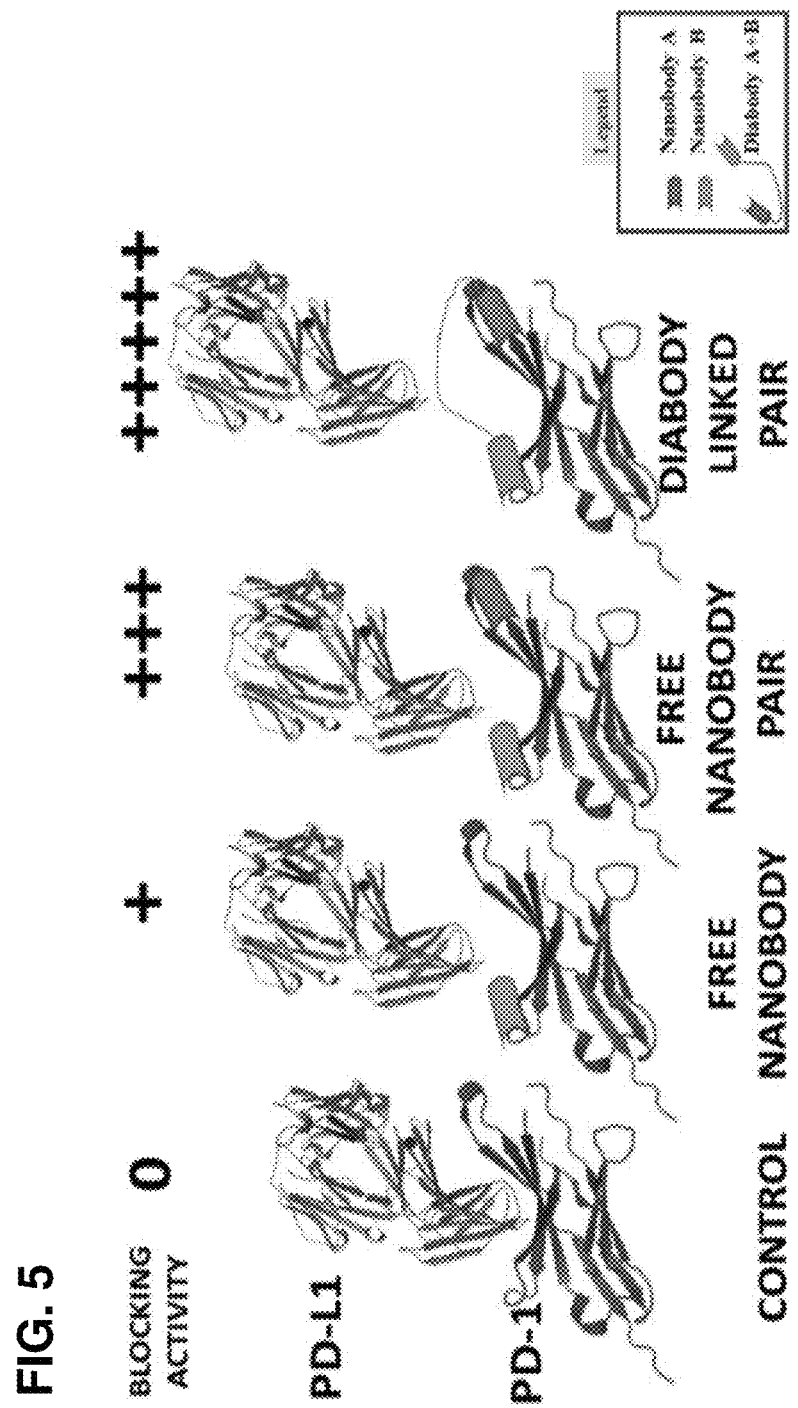

_US 11,629,190 B2_

SEQUENCE LISTING

```
<160> NUMBER OF SEQ ID NOS: 119

<210> SEQ ID NO 1
<211> LENGTH: 121
<212> TYPE: PRT
<213> ORGANISM: Artificial Sequence
<220> FEATURE:
<223> OTHER INFORMATION: VHH domain of NAN4 (5A1).

<400> SEQUENCE: 1

Gln Val Gln Leu Gln Ala Ser Gly Gly Gly Leu Val Gln Pro Gly Gly
1               5                   10                  15
```

```
Ser Leu Thr Leu Ser Cys Ala Ala Ser Gly Ser Ile Asp Ser Ile Leu
            20                  25                  30

Ala Met Gly Trp Tyr Arg Gln Gly Pro Gly Lys Gln Arg Glu Phe Val
            35                  40                  45

Ala Ser Ile Ser Trp Ser Gly Asp Ile Thr Tyr Ala Asp Ser Ala
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Asn Ala Gly Pro Asp Met Gln Ile Ser Gly Pro Thr Asp Tyr Asp
            100                 105                 110

Tyr Trp Gly Gln Gly Thr Gln Val Gly
            115                 120

<210> SEQ ID NO 2
<211> LENGTH: 9
<212> TYPE: PRT
<213> ORGANISM: Artificial Sequence
<220> FEATURE:
<223> OTHER INFORMATION: CDR1 of of NAN4 (5A1)

<400> SEQUENCE: 2

Ser Ile Asp Ser Ile Leu Ala Met Gly
1               5

<210> SEQ ID NO 3
<211> LENGTH: 10
<212> TYPE: PRT
<213> ORGANISM: Artificial Sequence
<220> FEATURE:
<223> OTHER INFORMATION: CDR2 of NAN4 (5A1)

<400> SEQUENCE: 3

Ser Ile Ser Trp Ser Gly Asp Ile Thr Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: CDR3 of NAN4 (5A1)

<400> SEQUENCE: 4

Gly Pro Asp Met Gln Ile Ser Gly Pro Thr Asp Tyr Asp Tyr
1               5                   10              15

<210> SEQ ID NO 5
<211> LENGTH: 115
<212> TYPE: PRT
<213> ORGANISM: Artificial Sequence
<220> FEATURE:
<223> OTHER INFORMATION: VHH domain of NAN7/8 (5A5)

<400> SEQUENCE: 5

Gln Val Gln Leu Gln Ala Ser Gly Gly Gly Leu Val Glu Pro Gly Gly
1               5                   10                  15

Ser Leu Arg Leu Ser Cys Ala Ala Ser Gly Ala Ile Phe Arg Ile Ala
            20                  25                  30

Ala Met Gly Trp Tyr Arg Gln Ala Pro Gly Lys Glu Arg Glu Leu Val
            35                  40                  45
```

```
Ala Thr Ile Thr Arg Gly Gly Ser Thr Asn Tyr Ala Asp Ser Val Lys
    50                  55                  60

Gly Arg Phe Thr Ile Ser Arg Asp Asn Ala Lys Asn Thr Ala Tyr Leu
65                  70                  75                  80

Gln Met Asp Ser Leu Lys Ala Glu Asp Thr Gly Val Tyr Tyr Cys Asn
                85                  90                  95

Ala Gly Leu Trp Ala Thr Thr Ser Ala Asn Tyr Trp Gly Gln Gly Thr
            100                 105                 110

Gln Val Gly
        115

<210> SEQ ID NO 6
<211> LENGTH: 9
<212> TYPE: PRT
<213> ORGANISM: Artificial Sequence
<220> FEATURE:
<223> OTHER INFORMATION: CDR1 of NAN7/8 (5A5).

<400> SEQUENCE: 6

Ala Ile Phe Arg Ile Ala Ala Met Gly
1               5

<210> SEQ ID NO 7
<211> LENGTH: 9
<212> TYPE: PRT
<213> ORGANISM: Artificial Sequence
<220> FEATURE:
<223> OTHER INFORMATION: CDR2 of NAN7/8 (5A5)

<400> SEQUENCE: 7

Thr Ile Thr Arg Gly Gly Ser Thr Asn
1               5

<210> SEQ ID NO 8
<211> LENGTH: 10
<212> TYPE: PRT
<213> ORGANISM: Artificial Sequence
<220> FEATURE:
<223> OTHER INFORMATION: CDR2 of NAN7/8 (5A5)

<400> SEQUENCE: 8

Gly Leu Trp Ala Thr Thr Ser Ala Asn Tyr
1               5                   10

<210> SEQ ID NO 9
<211> LENGTH: 118
<212> TYPE: PRT
<213> ORGANISM: Artificial Sequence
<220> FEATURE:
<223> OTHER INFORMATION: VHH domain of NAN10 (4B4)

<400> SEQUENCE: 9

Gln Val Gln Leu Gln Ala Ser Gly Gly Gly Leu Val Gln Gly Gly Glu
1               5                   10                  15

Ser Leu Arg Leu Ser Cys Ala Ala Ser Gly Arg Thr Val Ala Glu Tyr
                20                  25                  30

Thr Ile Gly Trp Tyr Arg Gln Ala Pro Gly Lys Glu Arg Glu Phe Val
            35                  40                  45

Ala Gly Pro Ser Trp His Ala Arg Gly Thr Ser Tyr Leu Asp Ser Val
        50                  55                  60

Lys Gly Arg Phe Thr Ile Ser Arg Asp Asn Thr Lys Asp Thr Val Tyr
65                  70                  75                  80
```

```
Leu Gln Met Asn Thr Leu Lys Pro Glu Asp Thr Ala Val Tyr Tyr Cys
            85                  90                  95

Asn Ala Asp Val Asn Thr Asp Tyr Ser Glu Tyr Val Glu Tyr Trp Gly
            100                 105                 110

Gln Gly Thr Gln Val Gly
        115

<210> SEQ ID NO 10
<211> LENGTH: 9
<212> TYPE: PRT
<213> ORGANISM: Artificial Sequence
<220> FEATURE:
<223> OTHER INFORMATION: CDR1 of NAN10 (4B4)

<400> SEQUENCE: 10

Arg Thr Val Ala Glu Tyr Thr Ile Gly
1               5

<210> SEQ ID NO 11
<211> LENGTH: 10
<212> TYPE: PRT
<213> ORGANISM: Artificial Sequence
<220> FEATURE:
<223> OTHER INFORMATION: CDR2 of NAN10 (4B4)

<400> SEQUENCE: 11

Gly Pro Ser Trp His Ala Arg Gly Thr Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: CDR3 of NAN10 (4B4)

<400> SEQUENCE: 12

Asp Val Asn Thr Asp Tyr Ser Glu Tyr Val Glu Tyr
1               5                   10

<210> SEQ ID NO 13
<211> LENGTH: 118
<212> TYPE: PRT
<213> ORGANISM: Artificial Sequence
<220> FEATURE:
<223> OTHER INFORMATION: VHH domain of NAN15 (4B2)

<400> SEQUENCE: 13

Gln Val Gln Leu Gln Ala Ser Gly Gly Gly Leu Val Gln Pro Gly Glu
1               5                   10                  15

His Leu Leu Leu Ser Cys Ala Ala Ser Gly Phe Ala Phe Gly Ile Tyr
            20                  25                  30

Thr Met Gly Trp Tyr Arg Gln Ala Pro Gly Lys Glu Arg Glu Lys Val
        35                  40                  45

Ala Ser Ile Ser Arg Thr Ser Asp Ser Trp Asn Tyr Ala Asp Ser Val
    50                  55                  60

Lys Gly Arg Phe Thr Ile Ser Arg Glu Asn Ala Lys Asn Thr Leu Tyr
65                  70                  75                  80

Leu Gln Met Asn Ser Leu Lys Pro Glu Asp Thr Ala Leu Tyr Phe Cys
            85                  90                  95

Ala Lys Ser Arg Ser Ala Trp Asn Thr Asp Asp Ile Glu Tyr Trp Gly
            100                 105                 110
```

Gln Gly Thr Gln Val Gly
        115

<210> SEQ ID NO 14
<211> LENGTH: 9
<212> TYPE: PRT
<213> ORGANISM: Artificial Sequence
<220> FEATURE:
<223> OTHER INFORMATION: CDR1 of NAN15 (4B2)

<400> SEQUENCE: 14

Phe Ala Phe Gly Ile Tyr Thr Met Gly
1               5

<210> SEQ ID NO 15
<211> LENGTH: 10
<212> TYPE: PRT
<213> ORGANISM: Artificial Sequence
<220> FEATURE:
<223> OTHER INFORMATION: CDR2 of NAN15 (4B2)

<400> SEQUENCE: 15

Ser Ile Ser Arg Thr Ser Asp Ser Trp Asn
1               5                   10

<210> SEQ ID NO 16
<211> LENGTH: 12
<212> TYPE: PRT
<213> ORGANISM: Artificial Sequence
<220> FEATURE:
<223> OTHER INFORMATION: CDR3 of NAN15 (4B2)

<400> SEQUENCE: 16

Ser Arg Ser Ala Trp Asn Thr Asp Asp Ile Glu Tyr
1               5                   10

<210> SEQ ID NO 17
<211> LENGTH: 116
<212> TYPE: PRT
<213> ORGANISM: Artificial Sequence
<220> FEATURE:
<223> OTHER INFORMATION: VHH domain of NAN28(1B5)

<400> SEQUENCE: 17

Gln Val Gln Leu Val Gln Ala Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Ser Gly Met Ser Trp Val Arg Gln Ala Pro Gly Lys Gly Leu Glu Trp
        35                  40                  45

Val Ala Gly Ile Asp Ser Ala Gly Gly Tyr Thr Thr Tyr Ala Asp Ser
    50                  55                  60

Val Lys Gly Arg Phe Thr Ile Ser Arg Asp Asn Thr Lys Asn Thr Val
65                  70                  75                  80

Tyr Leu Gln Met Asn Asn Leu Lys Pro Glu Asp Thr Ala Val Tyr Tyr
                85                  90                  95

Cys Asn Ala Thr Phe Ala Tyr Gly Glu Pro Tyr Trp Gly Gln Gly
            100                 105                 110

Thr Gln Val Gly
        115

<210> SEQ ID NO 18

```
<211> LENGTH: 10
<212> TYPE: PRT
<213> ORGANISM: Artificial Sequence
<220> FEATURE:
<223> OTHER INFORMATION: CDR1 of NAN28(1B5)

<400> SEQUENCE: 18

Gly Phe Thr Phe Ser Ser Ser Gly Met Ser
1               5                   10

<210> SEQ ID NO 19
<211> LENGTH: 10
<212> TYPE: PRT
<213> ORGANISM: Artificial Sequence
<220> FEATURE:
<223> OTHER INFORMATION: CDR2 of NAN28(1B5)

<400> SEQUENCE: 19

Gly Ile Asp Ser Ala Gly Gly Tyr Thr Thr
1               5                   10

<210> SEQ ID NO 20
<211> LENGTH: 9
<212> TYPE: PRT
<213> ORGANISM: Artificial Sequence
<220> FEATURE:
<223> OTHER INFORMATION: CDR3 of NAN28(1B5)

<400> SEQUENCE: 20

Thr Phe Ala Tyr Gly Glu Pro Trp Tyr
1               5

<210> SEQ ID NO 21
<211> LENGTH: 115
<212> TYPE: PRT
<213> ORGANISM: Artificial Sequence
<220> FEATURE:
<223> OTHER INFORMATION: VHH domain of NAN 1

<400> SEQUENCE: 21

Gln Val Gln Leu Gln Ala Ser Gly Gly Gly Leu Val Gln Pro Gly Gly
1               5                   10                  15

Ser Leu Arg Leu Ser Cys Ala Ala Ser Gly Ile Ile Asp Ser Ile Tyr
            20                  25                  30

Ala Met Gly Trp Tyr Arg Gln Ala Pro Gly Lys Gln Arg Glu Leu Val
        35                  40                  45

Ala Thr Ile Thr Asp Ser Gly Ser Thr Asn Tyr Ala Asp Ser Val Lys
    50                  55                  60

Gly Arg Phe Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Gly Asp Gly Trp Gly Thr Val Asp Tyr Trp Gly Gln Gly Thr
            100                 105                 110

Gln Val Gly
        115

<210> SEQ ID NO 22
<211> LENGTH: 9
<212> TYPE: PRT
<213> ORGANISM: Artificial Sequence
<220> FEATURE:
<223> OTHER INFORMATION: CDR1 of NAN 1
```

```
<400> SEQUENCE: 22

Ile Ile Asp Ser Ile Tyr Ala Met Gly
1               5

<210> SEQ ID NO 23
<211> LENGTH: 9
<212> TYPE: PRT
<213> ORGANISM: Artificial Sequence
<220> FEATURE:
<223> OTHER INFORMATION: CDR2 of NAN 1

<400> SEQUENCE: 23

Thr Ile Thr Asp Ser Gly Ser Thr Asn
1               5

<210> SEQ ID NO 24
<211> LENGTH: 10
<212> TYPE: PRT
<213> ORGANISM: Artificial Sequence
<220> FEATURE:
<223> OTHER INFORMATION: CDR3 of NAN 1

<400> SEQUENCE: 24

Glu Gly Asp Gly Trp Gly Thr Val Asp Tyr
1               5                   10

<210> SEQ ID NO 25
<211> LENGTH: 120
<212> TYPE: PRT
<213> ORGANISM: Artificial Sequence
<220> FEATURE:
<223> OTHER INFORMATION: VHH domain of NAN 2.

<400> SEQUENCE: 25

Gln Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Leu Asp Tyr Ala
            20                  25                  30

Ile Gly Trp Phe Arg Gln Ala Pro Gly Lys Glu Arg Glu Gly Val Ser
        35                  40                  45

Cys Ile Ser Ser Ser Asp Asp Ser Thr Tyr Tyr Arg Asp Ser Val Lys
    50                  55                  60

Gly Arg Phe Thr Ile Ser Arg Asp Asn Ala Gln Asn Thr Val Tyr Leu
65                  70                  75                  80

Gln Met Asn Asn Leu Lys Pro Glu Asp Thr Ala Val Tyr Tyr Cys Asn
                85                  90                  95

Ala Asp Trp Ala His Ser Asp Tyr Ala Thr Ser Ile Met Gly Asp Tyr
            100                 105                 110

Trp Gly Gln Gly Thr Gln Val Gly
        115                 120

<210> SEQ ID NO 26
<211> LENGTH: 8
<212> TYPE: PRT
<213> ORGANISM: Artificial Sequence
<220> FEATURE:
<223> OTHER INFORMATION: CDr1 of NAN 2

<400> SEQUENCE: 26

Phe Thr Leu Asp Tyr Ala Ile Gly
1               5
```

```
<210> SEQ ID NO 27
<211> LENGTH: 10
<212> TYPE: PRT
<213> ORGANISM: Artificial Sequence
<220> FEATURE:
<223> OTHER INFORMATION: CDR2 of NAN 2

<400> SEQUENCE: 27

Cys Ile Ser Ser Ser Asp Asp Ser Thr Tyr
1               5                   10

<210> SEQ ID NO 28
<211> LENGTH: 15
<212> TYPE: PRT
<213> ORGANISM: Artificial Sequence
<220> FEATURE:
<223> OTHER INFORMATION: CDR3 of NAN 2

<400> SEQUENCE: 28

Asp Trp Ala His Ser Asp Tyr Ala Thr Ser Ile Met Gly Asp Tyr
1               5                   10                  15

<210> SEQ ID NO 29
<211> LENGTH: 112
<212> TYPE: PRT
<213> ORGANISM: Artificial Sequence
<220> FEATURE:
<223> OTHER INFORMATION: VHH domain of NAN3

<400> SEQUENCE: 29

Gln Val Gln Leu Leu Ala Ser Gly Gly Gly Leu Val Gln Pro Gly Gly
1               5                   10                  15

Ser Leu Arg Leu Ser Cys Val Thr Ser Gly Phe Thr Phe Glu Asn Tyr
                20                  25                  30

Val Met Ala Trp Tyr Arg Gln Ala Pro Gly Lys Glu Arg Glu Leu Val
            35                  40                  45

Ala Gly Ile Thr Arg Ser Asp Gly Ser Thr Asn Tyr Ala Asp Ser Val
        50                  55                  60

Lys Gly Arg Phe Thr Ile Ser Arg Asp Asn Ala Lys Asn Thr Val His
65                  70                  75                  80

Leu Gln Met Asn Asn Leu Lys Pro Glu Asp Thr Ala Ile Tyr Tyr Cys
                85                  90                  95

Lys Ala Asn Thr Arg Gly Val Val Ala Glu Ala Tyr Glu Tyr Asp Tyr
            100                 105                 110

<210> SEQ ID NO 30
<211> LENGTH: 9
<212> TYPE: PRT
<213> ORGANISM: Artificial Sequence
<220> FEATURE:
<223> OTHER INFORMATION: CDR1 of NAN3

<400> SEQUENCE: 30

Phe Thr Phe Glu Asn Tyr Val Met Ala
1               5

<210> SEQ ID NO 31
<211> LENGTH: 10
<212> TYPE: PRT
<213> ORGANISM: Artificial Sequence
<220> FEATURE:
<223> OTHER INFORMATION: CDR2 of NAN3

<400> SEQUENCE: 31
```

Gly Ile Thr Arg Ser Asp Gly Ser Thr Asn
1               5                   10

<210> SEQ ID NO 32
<211> LENGTH: 14
<212> TYPE: PRT
<213> ORGANISM: Artificial Sequence
<220> FEATURE:
<223> OTHER INFORMATION: CDR3 of NAN3

<400> SEQUENCE: 32

Asn Thr Arg Gly Val Val Ala Glu Ala Tyr Glu Tyr Asp Tyr
1               5                   10

<210> SEQ ID NO 33
<211> LENGTH: 120
<212> TYPE: PRT
<213> ORGANISM: Artificial Sequence
<220> FEATURE:
<223> OTHER INFORMATION: VHH of NAN5

<400> SEQUENCE: 33

Gln Val Gln Leu Gln Ala Ser Gly Gly Gly Ala Val Gln Pro Gly Gly
1               5                   10                  15

Ser Leu Arg Leu Ser Cys Ala Ala Ser Gly Tyr Ser Phe Ser Lys Tyr
            20                  25                  30

Glu Val Ser Trp Val Arg Gln Ala Pro Gly Lys Gly Leu Glu Trp Val
        35                  40                  45

Ser Ala Ile Ser Arg Gly Gly Asp Ser Ala Tyr Tyr Ala Ala Ser Val
    50                  55                  60

Lys Asp Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Ala Ser Tyr Tyr Cys Ser Pro Leu Pro Leu Tyr Asp Tyr
            100                 105                 110

Trp Gly Gln Gly Thr Gln Val Gly
        115                 120

<210> SEQ ID NO 34
<211> LENGTH: 9
<212> TYPE: PRT
<213> ORGANISM: Artificial Sequence
<220> FEATURE:
<223> OTHER INFORMATION: CDR1 of NAN5

<400> SEQUENCE: 34

Tyr Ser Phe Ser Lys Tyr Glu Val Ser
1               5

<210> SEQ ID NO 35
<211> LENGTH: 10
<212> TYPE: PRT
<213> ORGANISM: Artificial Sequence
<220> FEATURE:
<223> OTHER INFORMATION: CDR2 of NAN5

<400> SEQUENCE: 35

Ala Ile Ser Arg Gly Gly Asp Ser Ala Tyr
1               5                   10

<210> SEQ ID NO 36
<211> LENGTH: 14

```
<212> TYPE: PRT
<213> ORGANISM: Artificial Sequence
<220> FEATURE:
<223> OTHER INFORMATION: CDR3 of NAN5

<400> SEQUENCE: 36

Val Ala Ser Tyr Tyr Cys Ser Pro Leu Pro Leu Tyr Asp Tyr
1               5                   10

<210> SEQ ID NO 37
<211> LENGTH: 115
<212> TYPE: PRT
<213> ORGANISM: Artificial Sequence
<220> FEATURE:
<223> OTHER INFORMATION: VHH domain of NAN6

<400> SEQUENCE: 37

Gln Val Gln Leu Gln Ala Ser Gly Gly Gly Leu Val Gln Pro Gly Gly
1               5                   10                  15

Ser Leu Thr Leu Ser Cys Ala Ala Ser Gly Ser Ile Asp Ser Ile Leu
            20                  25                  30

Ala Met Gly Trp Tyr Arg Gln Gly Pro Gly Lys Gln Arg Glu Leu Val
        35                  40                  45

Ala Thr Ile Thr Ser Asp Gly Gly Ser Thr Asn Tyr Ala Glu Tyr Val
    50                  55                  60

Lys Gly Arg Phe Thr Ile Ser Arg Asp Asp Ala Asn Asn Thr Ala Cys
65                  70                  75                  80

Leu Gln Met Asp Asn Leu Lys Pro Asp Asp Thr Ala Val Tyr Tyr Cys
                85                  90                  95

Asn Ala Lys Gly Arg Arg Leu Ser Tyr Gly Tyr Trp Gly Gln Gly Thr
            100                 105                 110

Gln Val Gly
        115

<210> SEQ ID NO 38
<211> LENGTH: 9
<212> TYPE: PRT
<213> ORGANISM: Artificial Sequence
<220> FEATURE:
<223> OTHER INFORMATION: CDR1 of NAN6

<400> SEQUENCE: 38

Ser Ile Asp Ser Ile Leu Ala Met Gly
1               5

<210> SEQ ID NO 39
<211> LENGTH: 10
<212> TYPE: PRT
<213> ORGANISM: Artificial Sequence
<220> FEATURE:
<223> OTHER INFORMATION: CDR2 of NAN6

<400> SEQUENCE: 39

Thr Ile Thr Ser Asp Gly Gly Ser Thr Asn
1               5                   10

<210> SEQ ID NO 40
<211> LENGTH: 9
<212> TYPE: PRT
<213> ORGANISM: Artificial Sequence
<220> FEATURE:
<223> OTHER INFORMATION: CDR3 of NAN6

<400> SEQUENCE: 40
```

Lys Gly Arg Arg Leu Ser Tyr Gly Tyr
1               5

<210> SEQ ID NO 41
<211> LENGTH: 119
<212> TYPE: PRT
<213> ORGANISM: Artificial Sequence
<220> FEATURE:
<223> OTHER INFORMATION: VHH domain of NAN9

<400> SEQUENCE: 41

Gln Val Gln Leu Gln Ala Ser Gly Gly Gly Leu Val Gln Pro Gly Gly
1               5                   10                  15

Ser Leu Arg Leu Ser Cys Ala Thr Ser Gly Phe Thr Leu Asp Asn Leu
            20                  25                  30

Ala Ile Gly Trp Leu Arg Gln Ala Pro Gly Lys Glu Arg Glu Gly Val
        35                  40                  45

Ser Cys Ile Ser Gly Ser Val Gly Ser Thr Tyr Tyr Val Asp Ser Val
    50                  55                  60

Glu Gly Arg Phe Thr Ile Ser Lys Asp Asn Ala Lys Asn Thr Val Ala
65                  70                  75                  80

Leu Gln Met Asp Arg Leu Asn Pro Glu Asp Thr Ala Val Tyr Tyr Cys
                85                  90                  95

Ser Ala Val Gly Arg Glu Arg Thr His Leu Pro Asn Trp Gln Tyr Trp
            100                 105                 110

Gly Gln Gly Thr Gln Val Gly
        115

<210> SEQ ID NO 42
<211> LENGTH: 9
<212> TYPE: PRT
<213> ORGANISM: Artificial Sequence
<220> FEATURE:
<223> OTHER INFORMATION: CDR1 of NAN9

<400> SEQUENCE: 42

Phe Thr Leu Asp Asn Leu Ala Ile Gly
1               5

<210> SEQ ID NO 43
<211> LENGTH: 10
<212> TYPE: PRT
<213> ORGANISM: Artificial Sequence
<220> FEATURE:
<223> OTHER INFORMATION: CDR2 of NAN9

<400> SEQUENCE: 43

Cys Ile Ser Gly Ser Val Gly Ser Thr Tyr
1               5                   10

<210> SEQ ID NO 44
<211> LENGTH: 13
<212> TYPE: PRT
<213> ORGANISM: Artificial Sequence
<220> FEATURE:
<223> OTHER INFORMATION: CDR3 of NAN9

<400> SEQUENCE: 44

Val Gly Arg Glu Arg Thr His Leu Pro Asn Trp Gln Tyr
1               5                   10

<210> SEQ ID NO 45

```
<211> LENGTH: 117
<212> TYPE: PRT
<213> ORGANISM: Artificial Sequence
<220> FEATURE:
<223> OTHER INFORMATION: VHH domain of NAN11

<400> SEQUENCE: 45

Gln Val Gln Leu Gln Ala Ser Gly Gly Gly Leu Val Gln Pro Gly Gly
1               5                   10                  15

Ser Leu Thr Leu Ser Cys Ala Ala Ser Gly Phe Pro Phe Leu Asp Tyr
            20                  25                  30

Ala Leu Ser Trp Tyr Arg Gln Thr Pro Gly Lys Glu Arg Glu Leu Val
        35                  40                  45

Ala Ser Ile Ser Arg Phe Gly Ser Asn Thr Asn Tyr Ala Asp Ser Val
    50                  55                  60

Lys Gly Arg Phe Thr Ala Ser Lys Asp Ser Thr Thr Asn Thr Val Tyr
65                  70                  75                  80

Leu Gln Met Asn Ser Leu Lys Pro Glu Asp Thr Ala Val Tyr Tyr Cys
                85                  90                  95

Lys Ala Ala Arg Val Leu Gly Tyr Pro Pro Ile Glu His Trp Gly Gln
            100                 105                 110

Gly Thr Gln Val Gly
        115

<210> SEQ ID NO 46
<211> LENGTH: 9
<212> TYPE: PRT
<213> ORGANISM: Artificial Sequence
<220> FEATURE:
<223> OTHER INFORMATION: CDR1 of NAN11

<400> SEQUENCE: 46

Phe Pro Phe Leu Asp Tyr Ala Leu Ser
1               5

<210> SEQ ID NO 47
<211> LENGTH: 10
<212> TYPE: PRT
<213> ORGANISM: Artificial Sequence
<220> FEATURE:
<223> OTHER INFORMATION: CDR2 of NAN11

<400> SEQUENCE: 47

Ser Ile Ser Arg Phe Gly Ser Asn Thr Asn
1               5                   10

<210> SEQ ID NO 48
<211> LENGTH: 11
<212> TYPE: PRT
<213> ORGANISM: Artificial Sequence
<220> FEATURE:
<223> OTHER INFORMATION: CDR3 of NAN11

<400> SEQUENCE: 48

Ala Arg Val Leu Gly Tyr Pro Pro Ile Glu His
1               5                   10

<210> SEQ ID NO 49
<211> LENGTH: 116
<212> TYPE: PRT
<213> ORGANISM: Artificial Sequence
<220> FEATURE:
<223> OTHER INFORMATION: VHH domain of NAN12
```

-continued

```
<400> SEQUENCE: 49

Gln Val Gln Leu Gln Ala Cys Gly Gly Gly Leu Val Gln Pro Gly Gly
1               5                   10                  15

Ser Leu Thr Leu Ser Ala Ala Ser Gly Phe Pro Phe Leu Asp Tyr Ser
            20                  25                  30

Leu Ser Trp Tyr Arg Gln Thr Pro Gly Lys Glu Arg Glu Leu Val Ala
        35                  40                  45

Ser Ile Ser Arg Phe Gly Ser Asn Thr Asn Tyr Ala Asp Ser Val Lys
    50                  55                  60

Gly Arg Phe Thr Ala Ser Lys Asp Ser Thr Thr Asn Thr Val Tyr Leu
65                  70                  75                  80

Gln Met Asn Ser Leu Lys Pro Glu Asp Thr Ala Val Tyr Tyr Cys Lys
                85                  90                  95

Ala Ala Arg Val Leu Gly Tyr Pro Pro Ile Glu His Trp Gly Gln Gly
            100                 105                 110

Thr Gln Val Gly
        115

<210> SEQ ID NO 50
<211> LENGTH: 9
<212> TYPE: PRT
<213> ORGANISM: Artificial Sequence
<220> FEATURE:
<223> OTHER INFORMATION: CDR1 of NAN12

<400> SEQUENCE: 50

Phe Pro Phe Leu Asp Tyr Ser Leu Ser
1               5

<210> SEQ ID NO 51
<211> LENGTH: 10
<212> TYPE: PRT
<213> ORGANISM: Artificial Sequence
<220> FEATURE:
<223> OTHER INFORMATION: CDR2 of NAN12

<400> SEQUENCE: 51

Ser Ile Ser Arg Phe Gly Ser Asn Thr Asn
1               5                   10

<210> SEQ ID NO 52
<211> LENGTH: 11
<212> TYPE: PRT
<213> ORGANISM: Artificial Sequence
<220> FEATURE:
<223> OTHER INFORMATION: CDR3 of NAN12

<400> SEQUENCE: 52

Ala Arg Val Leu Gly Tyr Pro Pro Ile Glu His
1               5                   10

<210> SEQ ID NO 53
<211> LENGTH: 118
<212> TYPE: PRT
<213> ORGANISM: Artificial Sequence
<220> FEATURE:
<223> OTHER INFORMATION: VHH domain of NAN13

<400> SEQUENCE: 53

Gln Val Gln Leu Gln Ala Ser Gly Gly Gly Leu Ala Gln Pro Gly Gly
1               5                   10                  15

Ser Leu Arg Leu Ser Cys Ala Ala Ser Gly Phe Thr Phe Ser Ser Tyr
```

```
                    20                  25                  30
Ala Met Ser Trp Ala Arg Gln Ala Pro Gly Lys Gly Leu Glu Trp Val
                35                  40                  45

Ser Gly Ile Tyr Ser Asp Gly Ser Gly Ser Tyr Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Lys Gly Ser Trp Ser Arg Gly Ile Lys Glu Thr Asp Tyr Trp Gly
            100                 105                 110

Gln Gly Thr Gln Val Gly
        115

<210> SEQ ID NO 54
<211> LENGTH: 9
<212> TYPE: PRT
<213> ORGANISM: Artificial Sequence
<220> FEATURE:
<223> OTHER INFORMATION: CDR1 of NAN13

<400> SEQUENCE: 54

Phe Thr Phe Ser Ser Tyr Ala Met Ser
1               5

<210> SEQ ID NO 55
<211> LENGTH: 10
<212> TYPE: PRT
<213> ORGANISM: Artificial Sequence
<220> FEATURE:
<223> OTHER INFORMATION: CDR2 of NAN13

<400> SEQUENCE: 55

Gly Ile Tyr Ser Asp Gly Ser Gly Ser Tyr
1               5                   10

<210> SEQ ID NO 56
<211> LENGTH: 12
<212> TYPE: PRT
<213> ORGANISM: Artificial Sequence
<220> FEATURE:
<223> OTHER INFORMATION: CDR3 of NAN13

<400> SEQUENCE: 56

Gly Ser Trp Ser Arg Gly Ile Lys Glu Thr Asp Tyr
1               5                   10

<210> SEQ ID NO 57
<211> LENGTH: 118
<212> TYPE: PRT
<213> ORGANISM: Artificial Sequence
<220> FEATURE:
<223> OTHER INFORMATION: VHH domain of NAN14

<400> SEQUENCE: 57

Gln Val Gln Leu Gln Ala Ser Gly Gly Gly Leu Ala Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Ala Arg Gln Ala Pro Gly Lys Gly Leu Glu Trp Val
                35                  40                  45

Ser Gly Ile Tyr Ser Asp Gly Ser Gly Ser Tyr Tyr Ala Asp Ser Val
```

```
                    50                  55                  60
Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Leu Tyr Tyr Cys
                     85                  90                  95

Ala Lys Gly Ser Trp Ser Arg Gly Ile Lys Glu Thr Asp Tyr Trp Gly
            100                 105                 110

Gln Gly Thr Gln Val Gly
        115

<210> SEQ ID NO 58
<211> LENGTH: 9
<212> TYPE: PRT
<213> ORGANISM: Artificial Sequence
<220> FEATURE:
<223> OTHER INFORMATION: CDR1 of NAN14

<400> SEQUENCE: 58

Phe Thr Phe Ser Ser Tyr Ala Met Ser
1               5

<210> SEQ ID NO 59
<211> LENGTH: 10
<212> TYPE: PRT
<213> ORGANISM: Artificial Sequence
<220> FEATURE:
<223> OTHER INFORMATION: CDR2 of NAN14

<400> SEQUENCE: 59

Gly Ile Tyr Ser Asp Gly Ser Gly Ser Tyr
1               5                   10

<210> SEQ ID NO 60
<211> LENGTH: 12
<212> TYPE: PRT
<213> ORGANISM: Artificial Sequence
<220> FEATURE:
<223> OTHER INFORMATION: CDR3 of NAN14

<400> SEQUENCE: 60

Gly Ser Trp Ser Arg Gly Ile Lys Glu Thr Asp Tyr
1               5                   10

<210> SEQ ID NO 61
<211> LENGTH: 121
<212> TYPE: PRT
<213> ORGANISM: Artificial Sequence
<220> FEATURE:
<223> OTHER INFORMATION: Vhh domain of NAN16

<400> SEQUENCE: 61

Gln Val Gln Leu Gln Ala Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Asn Met Gly Trp Phe Arg Gln Ala Pro Gly Lys Gly Leu Glu Trp Ile
        35                  40                  45

Ser Thr Ile Ser Thr Asp Gly Arg Thr Thr Tyr Tyr Ala Asp Ser Val
    50                  55                  60

Lys Gly Arg Phe Thr Ile Ser Arg Ser Asn Ala Glu Asn Thr Leu Tyr
 65                  70                  75                  80

Leu Gln Met Asn Thr Leu Lys Pro Glu Asp Thr Ala Val Tyr Tyr Cys
```

```
            85                  90                  95
Asn Gly Arg Ala Ser Ser Gly Thr Ala Leu Tyr Thr Arg Asn Arg Asp
        100                 105                 110

Tyr Trp Gly Gln Gly Thr Gln Val Gly
        115                 120

<210> SEQ ID NO 62
<211> LENGTH: 9
<212> TYPE: PRT
<213> ORGANISM: Artificial Sequence
<220> FEATURE:
<223> OTHER INFORMATION: CDR1 of NAN16

<400> SEQUENCE: 62

Arg Thr Phe Ser Ser Tyr Asn Met Gly
1               5

<210> SEQ ID NO 63
<211> LENGTH: 10
<212> TYPE: PRT
<213> ORGANISM: Artificial Sequence
<220> FEATURE:
<223> OTHER INFORMATION: CDR2 of NAN16

<400> SEQUENCE: 63

Thr Ile Ser Thr Asp Gly Arg Thr Thr Tyr
1               5                   10

<210> SEQ ID NO 64
<211> LENGTH: 15
<212> TYPE: PRT
<213> ORGANISM: Artificial Sequence
<220> FEATURE:
<223> OTHER INFORMATION: CDR3 of NAN16

<400> SEQUENCE: 64

Arg Ala Ser Ser Gly Thr Ala Leu Tyr Thr Arg Asn Arg Asp Tyr
1               5                   10                  15

<210> SEQ ID NO 65
<211> LENGTH: 109
<212> TYPE: PRT
<213> ORGANISM: Artificial Sequence
<220> FEATURE:
<223> OTHER INFORMATION: VHH domain of NAN17

<400> SEQUENCE: 65

Gln Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Phe Arg Thr Ala
            20                  25                  30

Val Met Lys Trp Tyr Arg Gln Ala Pro Gly Lys Glu Arg Glu Arg Val
        35                  40                  45

Ala Thr Ile Ile Ser Gly Gly Thr Tyr Lys Asn Tyr Ala Glu Phe Val
    50                  55                  60

Lys Gly Arg Phe Thr Ile Ser Arg Asp Asp Thr Lys Asn Met Val Tyr
65                  70                  75                  80

Leu Gln Met Asn Ser Leu Thr Pro Glu Asp Thr Ala Val Tyr Tyr Cys
                85                  90                  95

Ala Asn Gly Asp Leu Trp Gly Gln Gly Thr Gln Val Gly
            100                 105
```

```
<210> SEQ ID NO 66
<211> LENGTH: 9
<212> TYPE: PRT
<213> ORGANISM: Artificial Sequence
<220> FEATURE:
<223> OTHER INFORMATION: CDR1 of NAN17

<400> SEQUENCE: 66

Phe Thr Phe Arg Thr Ala Val Met Lys
1               5

<210> SEQ ID NO 67
<211> LENGTH: 10
<212> TYPE: PRT
<213> ORGANISM: Artificial Sequence
<220> FEATURE:
<223> OTHER INFORMATION: CDR2 of NAN17

<400> SEQUENCE: 67

Thr Ile Ile Ser Gly Gly Thr Tyr Lys Asn
1               5                   10

<210> SEQ ID NO 68
<211> LENGTH: 3
<212> TYPE: PRT
<213> ORGANISM: Artificial Sequence
<220> FEATURE:
<223> OTHER INFORMATION: CDR3 of NAN17

<400> SEQUENCE: 68

Gly Asp Leu
1

<210> SEQ ID NO 69
<211> LENGTH: 115
<212> TYPE: PRT
<213> ORGANISM: Artificial Sequence
<220> FEATURE:
<223> OTHER INFORMATION: VHH domain of NAN18

<400> SEQUENCE: 69

Gln Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Arg Trp Tyr Arg Gln Arg Pro Gly Glu Arg Glu Phe Val
        35                  40                  45

Ala Asp Ile Ser Gly Gly Gly Ser Thr Thr Asp Tyr Thr Asp Ser Val
    50                  55                  60

Lys Gly Arg Phe Thr Ile Ser Arg Glu Asn Ala Glu Arg Thr Val Tyr
65                  70                  75                  80

Leu Gln Met Ser Ser Leu Lys Pro Glu Asp Thr Ala Val Tyr Tyr Cys
                85                  90                  95

Asn Val Tyr Val Ser Arg Tyr Gly Gly Asp Phe Trp Gly Gln Gly Thr
            100                 105                 110

Gln Val Gly
        115

<210> SEQ ID NO 70
<211> LENGTH: 9
<212> TYPE: PRT
<213> ORGANISM: Artificial Sequence
<220> FEATURE:
<223> OTHER INFORMATION: CDR1 of NAN18
```

```
<400> SEQUENCE: 70

Phe Thr Phe Ser Asp Tyr Val Met Arg
1               5

<210> SEQ ID NO 71
<211> LENGTH: 10
<212> TYPE: PRT
<213> ORGANISM: Artificial Sequence
<220> FEATURE:
<223> OTHER INFORMATION: CDR2 of NAN18

<400> SEQUENCE: 71

Asp Ile Ser Gly Gly Gly Ser Thr Thr Asp
1               5                   10

<210> SEQ ID NO 72
<211> LENGTH: 9
<212> TYPE: PRT
<213> ORGANISM: Artificial Sequence
<220> FEATURE:
<223> OTHER INFORMATION: CDR3 of NAN18

<400> SEQUENCE: 72

Tyr Val Ser Arg Tyr Gly Gly Asp Phe
1               5

<210> SEQ ID NO 73
<211> LENGTH: 116
<212> TYPE: PRT
<213> ORGANISM: Artificial Sequence
<220> FEATURE:
<223> OTHER INFORMATION: VHH domain of NAN19

<400> SEQUENCE: 73

Gln Val Gln Leu Gln Ala Ser Gly Gly Gly Leu Pro Gly Gly Ser Leu
1               5                   10                  15

Arg Leu Ser Cys Thr Ala Ser Gly Ile Thr Ser Ser Leu Trp Thr Met
            20                  25                  30

Gly Trp Phe Arg Gln Gly Pro Gly Lys His Arg Asp Leu Val Gly His
        35                  40                  45

Val Thr Arg Gly Gly Ser Thr Thr Ile Val Asp Ser Val Arg Asp Arg
    50                  55                  60

Phe Thr Ile Ser Arg Asp Gly Asn Lys Asn Thr Ile Tyr Leu Gln Met
65                  70                  75                  80

Asn Asp Leu Lys Pro Glu Asp Thr Ala Val Tyr Tyr Cys Asn Gly Gly
                85                  90                  95

Arg Asn Glu Gly Phe Leu Gly Gly Val Asn Asp Tyr Trp Gly Gln Gly
            100                 105                 110

Thr Gln Val Gly
        115

<210> SEQ ID NO 74
<211> LENGTH: 9
<212> TYPE: PRT
<213> ORGANISM: Artificial Sequence
<220> FEATURE:
<223> OTHER INFORMATION: CDR1 of NAN19

<400> SEQUENCE: 74

Ile Thr Ser Ser Leu Trp Thr Met Gly
1               5
```

<210> SEQ ID NO 75
<211> LENGTH: 10
<212> TYPE: PRT
<213> ORGANISM: Artificial Sequence
<220> FEATURE:
<223> OTHER INFORMATION: CDR2 of NAN19

<400> SEQUENCE: 75

His Val Thr Arg Gly Gly Ser Thr Thr Ile
1               5                   10

<210> SEQ ID NO 76
<211> LENGTH: 13
<212> TYPE: PRT
<213> ORGANISM: Artificial Sequence
<220> FEATURE:
<223> OTHER INFORMATION: CDR3 of NAN19

<400> SEQUENCE: 76

Gly Arg Asn Glu Gly Phe Leu Gly Gly Val Asn Asp Tyr
1               5                   10

<210> SEQ ID NO 77
<211> LENGTH: 124
<212> TYPE: PRT
<213> ORGANISM: Artificial Sequence
<220> FEATURE:
<223> OTHER INFORMATION: VHH domain of NAN20

<400> SEQUENCE: 77

Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Thr Trp Ala Arg Gln Ala Pro Gly Lys Gly Leu Glu Trp Val
        35                  40                  45

Gly Gly Ile Tyr Ser Asp Gly Ser Glu Pro Tyr Tyr Ala Asp Ser Met
    50                  55                  60

Lys Gly Arg Phe Thr Ile Ser Arg Asp Asn Val Lys Ser Thr Leu Tyr
65                  70                  75                  80

Leu Gln Met Asn Asp Leu Lys Pro Glu Asp Thr Ala Leu Tyr Phe Cys
                85                  90                  95

Ala Lys Gly Arg Gly Asp Phe Leu Lys Ser Ala Trp Arg Glu Asn Arg
            100                 105                 110

Arg Tyr Asp Ser Trp Gly Gln Gly Thr Gln Val Gly
        115                 120

<210> SEQ ID NO 78
<211> LENGTH: 9
<212> TYPE: PRT
<213> ORGANISM: Artificial Sequence
<220> FEATURE:
<223> OTHER INFORMATION: CDR1 of NAN20

<400> SEQUENCE: 78

Tyr Thr Phe Thr Asn Tyr Gly Ile Thr
1               5

<210> SEQ ID NO 79
<211> LENGTH: 10
<212> TYPE: PRT
<213> ORGANISM: Artificial Sequence
<220> FEATURE:

<223> OTHER INFORMATION: CDR2 of NAN20

<400> SEQUENCE: 79

Gly Ile Tyr Ser Asp Gly Ser Glu Pro Tyr
1               5                   10

<210> SEQ ID NO 80
<211> LENGTH: 18
<212> TYPE: PRT
<213> ORGANISM: Artificial Sequence
<220> FEATURE:
<223> OTHER INFORMATION: CDr3 of NAN20

<400> SEQUENCE: 80

Gly Arg Gly Asp Phe Leu Lys Ser Ala Trp Arg Glu Asn Arg Arg Tyr
1               5                   10                  15

Asp Ser

<210> SEQ ID NO 81
<211> LENGTH: 120
<212> TYPE: PRT
<213> ORGANISM: Artificial Sequence
<220> FEATURE:
<223> OTHER INFORMATION: VHH domain of NAN21

<400> SEQUENCE: 81

Gln Val Gln Leu Gln Ala Ser Gly Gly Gly Leu Val Gln Pro Gly Gly
1               5                   10                  15

Ser Leu Arg Leu Ser Cys Ala Leu Ser Gly Asn Ile Phe Ser Ala Tyr
                20                  25                  30

Ser Met Gly Trp Tyr Arg Gln Ala Pro Gly Lys Gln Arg Glu Leu Val
            35                  40                  45

Ala Thr Ile Ser Asp Ser Gly Arg Thr Asn Phe Gly Asp Phe Ala Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ser Lys Thr Gly Asp His Val Tyr Thr Gly Ala Arg Trp Tyr Glu Tyr
                100                 105                 110

Trp Gly Gln Gly Thr Gln Val Gly
            115                 120

<210> SEQ ID NO 82
<211> LENGTH: 9
<212> TYPE: PRT
<213> ORGANISM: Artificial Sequence
<220> FEATURE:
<223> OTHER INFORMATION: CDR1 of NAN21

<400> SEQUENCE: 82

Asn Ile Phe Ser Ala Tyr Ser Met Gly
1               5

<210> SEQ ID NO 83
<211> LENGTH: 10
<212> TYPE: PRT
<213> ORGANISM: Artificial Sequence
<220> FEATURE:
<223> OTHER INFORMATION: CDR2 of NAN21

<400> SEQUENCE: 83

Thr Ile Ser Asp Ser Gly Arg Thr Asn Phe
1               5                   10

<210> SEQ ID NO 84
<211> LENGTH: 14
<212> TYPE: PRT
<213> ORGANISM: Artificial Sequence
<220> FEATURE:
<223> OTHER INFORMATION: CDR3 of NAN21

<400> SEQUENCE: 84

Thr Gly Asp His Val Tyr Thr Gly Ala Arg Trp Tyr Glu Tyr
1               5                   10

<210> SEQ ID NO 85
<211> LENGTH: 120
<212> TYPE: PRT
<213> ORGANISM: Artificial Sequence
<220> FEATURE:
<223> OTHER INFORMATION: VHH domain of NAN22

<400> SEQUENCE: 85

Gln Val Gln Leu Gln Ala Ser Gly Gly Gly Leu Val Gln Pro Gly Gly
1               5                   10                  15

Ser Leu Arg Leu Ser Cys Ala Ala Ser Gly Ser Ile Phe Gly Leu Tyr
                20                  25                  30

Ala Met Gly Trp Tyr Arg Gln Ala Pro Gly Lys Gln Arg Asp Leu Val
            35                  40                  45

Ala Ala Ile Ala Ser Gly Gly Ser Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Asp Tyr Tyr Cys Asn
                85                  90                  95

Val Ala Gly Asp Val Thr Ala Gln Asn Arg Cys Lys His Leu Glu Val
            100                 105                 110

Trp Gly Gln Gly Thr Gln Val Gly
        115                 120

<210> SEQ ID NO 86
<211> LENGTH: 9
<212> TYPE: PRT
<213> ORGANISM: Artificial Sequence
<220> FEATURE:
<223> OTHER INFORMATION: CDR1 of NAN22

<400> SEQUENCE: 86

Ser Ile Phe Gly Leu Tyr Ala Met Gly
1               5

<210> SEQ ID NO 87
<211> LENGTH: 9
<212> TYPE: PRT
<213> ORGANISM: Artificial Sequence
<220> FEATURE:
<223> OTHER INFORMATION: CDR2 of NAN22

<400> SEQUENCE: 87

Ala Ile Ala Ser Gly Gly Ser Thr Asn
1               5

<210> SEQ ID NO 88
<211> LENGTH: 15

```
<212> TYPE: PRT
<213> ORGANISM: Artificial Sequence
<220> FEATURE:
<223> OTHER INFORMATION: CDR3 of NAN22

<400> SEQUENCE: 88

Ala Gly Asp Val Thr Ala Gln Asn Arg Cys Lys His Leu Glu Val
1               5                   10                  15

<210> SEQ ID NO 89
<211> LENGTH: 117
<212> TYPE: PRT
<213> ORGANISM: Artificial Sequence
<220> FEATURE:
<223> OTHER INFORMATION: VHH domain of NAN23

<400> SEQUENCE: 89

Gln Val Gln Leu Val Gln Ser Gly Gly Glu Val Lys Lys Pro Gly Gly
1               5                   10                  15

Ser Leu Arg Leu Ser Cys Ala Ala Ser Gly Ser Ile Phe Ser Ile Tyr
            20                  25                  30

Asp Met Gly Trp Tyr Arg Gln Ala Pro Gly Lys Gln Arg Glu Leu Val
        35                  40                  45

Ala Phe Ile Thr Arg Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Arg Val Gly Ala Thr Met Arg Arg Val Ser Tyr Trp Gly Gln
            100                 105                 110

Gly Thr Gln Val Gly
        115

<210> SEQ ID NO 90
<211> LENGTH: 9
<212> TYPE: PRT
<213> ORGANISM: Artificial Sequence
<220> FEATURE:
<223> OTHER INFORMATION: CDR1 of NAN23

<400> SEQUENCE: 90

Ser Ile Phe Ser Ile Tyr Asp Met Gly
1               5

<210> SEQ ID NO 91
<211> LENGTH: 9
<212> TYPE: PRT
<213> ORGANISM: Artificial Sequence
<220> FEATURE:
<223> OTHER INFORMATION: CDR2 of NAN23

<400> SEQUENCE: 91

Phe Ile Thr Arg Gly Gly Ser Thr Asn
1               5

<210> SEQ ID NO 92
<211> LENGTH: 12
<212> TYPE: PRT
<213> ORGANISM: Artificial Sequence
<220> FEATURE:
<223> OTHER INFORMATION: CDR3 of NAN23

<400> SEQUENCE: 92
```

Asp Arg Val Gly Ala Thr Met Arg Arg Val Ser Tyr
1               5                   10

<210> SEQ ID NO 93
<211> LENGTH: 109
<212> TYPE: PRT
<213> ORGANISM: Artificial Sequence
<220> FEATURE:
<223> OTHER INFORMATION: VHH domain of NAN24

<400> SEQUENCE: 93

Gln Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Phe Arg Thr Ala
            20                  25                  30

Val Met Lys Trp Tyr Arg Gln Ala Pro Gly Lys Glu Arg Glu Arg Val
        35                  40                  45

Ala Thr Ile Ile Ser Gly Gly Thr Tyr Lys Asn Tyr Ala Glu Phe Val
    50                  55                  60

Lys Gly Arg Phe Thr Ile Ser Arg Asp Asp Thr Lys Asn Met Val Tyr
65                  70                  75                  80

Leu Gln Met Asn Ser Leu Thr Pro Glu Asp Thr Ala Val Tyr Tyr Cys
                85                  90                  95

Ala Asn Gly Asp Leu Trp Gly Gln Gly Thr Gln Val Gly
            100                 105

<210> SEQ ID NO 94
<211> LENGTH: 9
<212> TYPE: PRT
<213> ORGANISM: Artificial Sequence
<220> FEATURE:
<223> OTHER INFORMATION: CDR1 of NAN24

<400> SEQUENCE: 94

Phe Thr Phe Arg Thr Ala Val Met Lys
1               5

<210> SEQ ID NO 95
<211> LENGTH: 10
<212> TYPE: PRT
<213> ORGANISM: Artificial Sequence
<220> FEATURE:
<223> OTHER INFORMATION: CDR2 of NAN24

<400> SEQUENCE: 95

Thr Ile Ile Ser Gly Gly Thr Tyr Lys Asn
1               5                   10

<210> SEQ ID NO 96
<211> LENGTH: 3
<212> TYPE: PRT
<213> ORGANISM: Artificial Sequence
<220> FEATURE:
<223> OTHER INFORMATION: CDR3 of NAN24

<400> SEQUENCE: 96

Gly Asp Leu
1

<210> SEQ ID NO 97
<211> LENGTH: 108
<212> TYPE: PRT
<213> ORGANISM: Artificial Sequence

```
<220> FEATURE:
<223> OTHER INFORMATION: VHH domain of NAN25

<400> SEQUENCE: 97

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Ala Phe Ser Val Leu
            20                  25                  30

Pro Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ser Lys Asn Thr Gln Tyr Leu
65                  70                  75                  80

Gln Met Asn Ser Leu Lys Pro Glu Asp Thr Ala Val Tyr Tyr Cys Asn
                85                  90                  95

Val Gly Gly Glu Phe Gly Gln Gly Thr Gln Val Gly
            100                 105

<210> SEQ ID NO 98
<211> LENGTH: 9
<212> TYPE: PRT
<213> ORGANISM: Artificial Sequence
<220> FEATURE:
<223> OTHER INFORMATION: CDR1 of NAN25

<400> SEQUENCE: 98

Phe Ala Phe Ser Val Leu Pro Met Gly
1               5

<210> SEQ ID NO 99
<211> LENGTH: 9
<212> TYPE: PRT
<213> ORGANISM: Artificial Sequence
<220> FEATURE:
<223> OTHER INFORMATION: CDR2 of NAN25

<400> SEQUENCE: 99

Ala Ile Thr Ser Gly Gly Ser Thr Asn
1               5

<210> SEQ ID NO 100
<211> LENGTH: 3
<212> TYPE: PRT
<213> ORGANISM: Artificial Sequence
<220> FEATURE:
<223> OTHER INFORMATION: CDR3 of NAN25

<400> SEQUENCE: 100

Gly Gly Glu
1

<210> SEQ ID NO 101
<211> LENGTH: 121
<212> TYPE: PRT
<213> ORGANISM: Artificial Sequence
<220> FEATURE:
<223> OTHER INFORMATION: VHH domain of NAN26

<400> SEQUENCE: 101

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Ser Leu Asp Gly Tyr
```

```
            20                  25                  30
Val Ile Gly Trp Phe Arg Gln Ala Pro Gly Lys Glu Arg Gln Gly Val
            35                  40                  45

Ser Cys Ile Ser Ser Gly Gly Thr Val Tyr Lys Asp Pro Val Lys
        50                  55                  60

Gly Arg Phe Thr Ile Ser Arg Asp Asn Ala Lys Asn Thr Val Tyr Leu
65                  70                  75                  80

Gln Met Asn Asn Leu Asn Val Glu Asp Thr Ala Val Tyr Tyr Cys Ala
                85                  90                  95

Ala Val Lys Thr Leu Ser Trp Pro Val Cys Arg Gly Glu Ala Phe Asp
            100                 105                 110

Ser Trp Gly Gln Gly Thr Gln Val Gly
        115                 120

<210> SEQ ID NO 102
<211> LENGTH: 9
<212> TYPE: PRT
<213> ORGANISM: Artificial Sequence
<220> FEATURE:
<223> OTHER INFORMATION: CDR1 of NAN26

<400> SEQUENCE: 102

Phe Ser Leu Asp Gly Tyr Val Ile Gly
1               5

<210> SEQ ID NO 103
<211> LENGTH: 9
<212> TYPE: PRT
<213> ORGANISM: Artificial Sequence
<220> FEATURE:
<223> OTHER INFORMATION: CDR2 of NAN26

<400> SEQUENCE: 103

Cys Ile Ser Ser Ser Gly Gly Thr Val
1               5

<210> SEQ ID NO 104
<211> LENGTH: 16
<212> TYPE: PRT
<213> ORGANISM: Artificial Sequence
<220> FEATURE:
<223> OTHER INFORMATION: CDR3 of NAN26

<400> SEQUENCE: 104

Val Lys Thr Leu Ser Trp Pro Val Cys Arg Gly Glu Ala Phe Asp Ser
1               5                   10                  15

<210> SEQ ID NO 105
<211> LENGTH: 111
<212> TYPE: PRT
<213> ORGANISM: Artificial Sequence
<220> FEATURE:
<223> OTHER INFORMATION: VHH domain of NAN27

<400> SEQUENCE: 105

Gln Pro Gln Ala Phe Gly Gly Gly Leu Val Gln Pro Gly Gly Ser Leu
1               5                   10                  15

Arg Leu Ser Cys Val Ala Ser Gly Ser Thr Asp Ser Ile Tyr Ala Met
            20                  25                  30

Gly Trp Tyr Arg Gln Ala Pro Gly Lys Gln Arg Glu Leu Val Ala Thr
            35                  40                  45

Ile Thr Ser Ala Asp Ser Thr Asn Tyr Ala Asp Ser Val Lys Gly Arg
```

```
                50                  55                  60
Phe Thr Ile Ser Arg Asp Asn Ala Lys Asn Thr Val Val Leu Gln Met
 65                  70                  75                  80

Asn Ser Leu Lys Pro Glu Asp Thr Ala Val Tyr Tyr Cys Asn Ala Gly
                 85                  90                  95

Ser Leu Ala Gly Tyr Asp Tyr Trp Gly Gln Gly Thr Gln Val Gly
            100                 105                 110

<210> SEQ ID NO 106
<211> LENGTH: 7
<212> TYPE: PRT
<213> ORGANISM: Artificial Sequence
<220> FEATURE:
<223> OTHER INFORMATION: CDR1 of NAN27

<400> SEQUENCE: 106

Asp Ser Ile Tyr Ala Met Gly
 1               5

<210> SEQ ID NO 107
<211> LENGTH: 9
<212> TYPE: PRT
<213> ORGANISM: Artificial Sequence
<220> FEATURE:
<223> OTHER INFORMATION: CDR2 of NAN27

<400> SEQUENCE: 107

Thr Ile Thr Ser Ala Asp Ser Thr Asn
 1               5

<210> SEQ ID NO 108
<211> LENGTH: 8
<212> TYPE: PRT
<213> ORGANISM: Artificial Sequence
<220> FEATURE:
<223> OTHER INFORMATION: CDR3 of NAN27

<400> SEQUENCE: 108

Gly Ser Leu Ala Gly Tyr Asp Tyr
 1               5

<210> SEQ ID NO 109
<211> LENGTH: 116
<212> TYPE: PRT
<213> ORGANISM: Artificial Sequence
<220> FEATURE:
<223> OTHER INFORMATION: VHH domain of NAN29

<400> SEQUENCE: 109

Gln Val Gln Leu Val Gln Ala Ser Gly Gly Gly Leu Val Gln Pro Gly
 1               5                  10                  15

Gly Ser Leu Thr Leu Ser Cys Ala Ala Ser Gly Ser Ile Asp Ser Ile
                20                  25                  30

Leu Ala Met Gly Trp Tyr Arg Gln Gly Pro Gly Lys Gln Arg Glu Leu
            35                  40                  45

Val Ala Thr Ile Thr Ser Asp Gly Gly Ser Thr Asn Tyr Ala Glu Tyr
         50                  55                  60

Val Lys Gly Arg Phe Thr Ile Ser Arg Asp Asp Ala Asn Asn Thr Ala
 65                  70                  75                  80

Cys Leu Gln Met Asp Asn Leu Lys Pro Asp Asp Thr Ala Val Tyr Tyr
                 85                  90                  95

Cys Asn Ala Lys Gly Arg Arg Leu Ser Tyr Gly Tyr Trp Gly Gln Gly
```

Thr Gln Val Gly
        115

<210> SEQ ID NO 110
<211> LENGTH: 10
<212> TYPE: PRT
<213> ORGANISM: Artificial Sequence
<220> FEATURE:
<223> OTHER INFORMATION: CDR1 of NAN29

<400> SEQUENCE: 110

Gly Ser Ile Asp Ser Ile Leu Ala Met Gly
1               5                   10

<210> SEQ ID NO 111
<211> LENGTH: 10
<212> TYPE: PRT
<213> ORGANISM: Artificial Sequence
<220> FEATURE:
<223> OTHER INFORMATION: CDR2 of NAN29

<400> SEQUENCE: 111

Thr Ile Thr Ser Asp Gly Gly Ser Thr Asn
1               5                   10

<210> SEQ ID NO 112
<211> LENGTH: 9
<212> TYPE: PRT
<213> ORGANISM: Artificial Sequence
<220> FEATURE:
<223> OTHER INFORMATION: CDR3 of NAN29

<400> SEQUENCE: 112

Lys Gly Arg Arg Leu Ser Tyr Gly Tyr
1               5

<210> SEQ ID NO 113
<211> LENGTH: 119
<212> TYPE: PRT
<213> ORGANISM: Artificial Sequence
<220> FEATURE:
<223> OTHER INFORMATION: VHH domain of NAN30

<400> SEQUENCE: 113

Gln Val Gln Leu Val Gln Ala Ser Gly Gly Gly Leu Ala Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Ala Arg Gln Ala Pro Lys Gly Leu Glu Trp
        35                  40                  45

Val Ser Gly Ile Tyr Ser Asp Gly Ser Gly Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Leu Tyr Tyr
                85                  90                  95

Cys Ala Lys Gly Ser Trp Ser Arg Gly Ile Lys Glu Thr Asp Tyr Trp
            100                 105                 110

Gly Gln Gly Thr Gln Val Gly
        115

```
<210> SEQ ID NO 114
<211> LENGTH: 10
<212> TYPE: PRT
<213> ORGANISM: Artificial Sequence
<220> FEATURE:
<223> OTHER INFORMATION: CDR1 of NAN30

<400> SEQUENCE: 114

Gly Phe Thr Phe Ser Ser Tyr Ala Met Ser
1               5                   10

<210> SEQ ID NO 115
<211> LENGTH: 10
<212> TYPE: PRT
<213> ORGANISM: Artificial Sequence
<220> FEATURE:
<223> OTHER INFORMATION: CDR2 of NAN30

<400> SEQUENCE: 115

Gly Ile Tyr Ser Asp Gly Ser Gly Ser Tyr
1               5                   10

<210> SEQ ID NO 116
<211> LENGTH: 12
<212> TYPE: PRT
<213> ORGANISM: Artificial Sequence
<220> FEATURE:
<223> OTHER INFORMATION: CDR3 of NAN30

<400> SEQUENCE: 116

Gly Ser Trp Ser Arg Gly Ile Lys Glu Thr Asp Tyr
1               5                   10

<210> SEQ ID NO 117
<211> LENGTH: 118
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
```

```
<222> LOCATION: (99)..(108)
<223> OTHER INFORMATION: Xaa can be any naturally occurring amino acid

<400> SEQUENCE: 117

Gln Val Gln Leu Gln Ala Ser Gly Gly Gly Leu Val Gln Pro Gly Gly
1               5                   10                  15

Ser Leu Arg Leu Ser Cys Ala Ala Ser Gly Xaa Thr Phe Ser Xaa Tyr
            20                  25                  30

Xaa Met Gly Trp Tyr Arg Gln Ala Pro Gly Lys Xaa Arg Glu Xaa Val
        35                  40                  45

Ala Xaa Ile Xaa Xaa Xaa Gly Xaa Ser Thr Asn Tyr Ala Asp Ser Val
    50                  55                  60

Lys Gly Arg Phe Thr Ile Ser Gly Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Xaa Xaa Xaa Xaa Xaa Xaa Xaa Xaa Xaa Asp Tyr Trp Gly
            100                 105                 110

Gln Gly Thr Gln Val Gly
        115

<210> SEQ ID NO 118
<211> LENGTH: 115
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (98)..(107)
<223> OTHER INFORMATION: Xaa can be any naturally occurring amino acid

<400> SEQUENCE: 118

Gln Val Gln Leu Gln Ala Ser Gly Gly Gly Leu Val Gln Pro Gly Gly
1               5                   10                  15

Ser Leu Arg Leu Ser Cys Ala Ala Ser Gly Ser Ile Phe Ser Ile Tyr
            20                  25                  30

Ala Met Gly Trp Tyr Arg Gln Ala Pro Gly Lys Gln Arg Glu Leu Val
        35                  40                  45

Ala Thr Ile Xaa Xaa Gly Xaa Ser Thr Asn Tyr Ala Asp Ser Val Lys
    50                  55                  60

Gly Arg Phe Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Xaa Xaa Xaa Xaa Xaa Xaa Xaa Xaa Xaa Trp Gly Gln Gly Thr
            100                 105                 110

Gln Val Gly
        115

<210> SEQ ID NO 119
<211> LENGTH: 115
<212> TYPE: PRT
```

```
<213> ORGANISM: Artificial Sequence
<220> FEATURE:
<223> OTHER INFORMATION: consensus sequence
<220> FEATURE:
<221> NAME/KEY: misc_feature
<222> LOCATION: (29)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid
<220> FEATURE:
<221> NAME/KEY: misc_feature
<222> LOCATION: (98)..(107)
<223> OTHER INFORMATION: Xaa can be any naturally occurring amino acid

<400> SEQUENCE: 119
```

Gln Val Gln Leu Gln Ala Ser Gly Gly Leu Val Gln Pro Gly Gly
1               5                   10                  15

Ser Leu Arg Leu Ser Cys Ala Ala Ser Gly Phe Thr Xaa Xaa Xaa Tyr
            20                  25                  30

Ala Xaa Gly Trp Tyr Arg Gln Ala Pro Gly Lys Gln Arg Glu Leu Val
        35                  40                  45

Ala Xaa Ile Ser Ser Gly Xaa Xaa Thr Tyr Tyr Ala Asp Ser Val Lys
    50                  55                  60

Gly Arg Phe Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Xaa Xaa Xaa Xaa Xaa Xaa Xaa Xaa Xaa Xaa Trp Gly Gln Gly Thr
            100                 105                 110

Gln Val Gly
        115

CANINE ANTIBODY THERAPEUTIC FOR TREATING CANCER

PRIORITY CLAIM

This application claims the benefit of U.S. Provisional Application No. 62/887,520, filed Aug. 15, 2019, which is herein incorporated by reference in its entirety.

FIELD OF THE DISCLOSURE

This relates to the field of antibodies, specifically to single heavy chain variable ($V_HH$) monoclonal antibodies and antigen binding fragments thereof that specifically bind programmed death (PD-1), and methods of use.

BACKGROUND

PD-1 (also known as, PDCD1 or CD279) is a protein expressed on the surface of some immune cells, including T cells and is involved in regulating immune responses to tissues and cells of the body. Binding of PD-1 cognate ligands (e.g. a PD-1-ligand (PD-L), such as PD-L1 and PD-L2) expressed on normal cells and tissues can induce a state of self-tolerance by triggering a signal to suppress potential "self-reactive" T cell killing activity and prevent autoimmune disease. However, some tumor cells also express large amounts of PD-L1, thereby evading T cell killing and promoting tumor growth and metastasis. Antibodies that disrupt the binding of PD-1 to anti-tumor T Cells, or to PD-L1 expressed on tumor cells, can reinvigorate exhausted T cells, thereby abrogating the immune suppressive activity of tumor cells and allow the body's immune system to control and or eliminate cancer disease.

Cancer is the leading cause of death for over 80% of dog breeds and all mix-breed dogs. This equates to cancer killing nearly 30% of all dogs each year (Fleming et al., Journal of Veterinary Internal Medicine, 25(2): p. 187-198, 2011). Unfortunately, primary cancer treatments for dogs are limited to older therapies used at clinically lower doses resulting in inferior outcomes compared to humans (Gustafson, D. L., et al., Pharmacol Ther, Pharmacol Ther, 188:80-96, 2018. Recently, therapies that augment immune cell activity have been shown to control and eradicate human cancers, establishing these immunotherapies as an effective first-line treatment of cancer (Niyongere et al. J. Thorac Dis 10(Suppl 3): p. 5433-s450, 2018; Carretero-Gonzalez, A., et al., Oncotarget 9(9): p. 8706-8715, 2018.

One immune target in cancer treatment is PD-1 (Ahmadzadeh et al., Blood, 114(8): p. 1537-1544, 2009). Two monoclonal antibodies that function therapeutically through the blockade of PD-1/PD-L1 in human cancer patients have been approved by the US Food and Drug Administration, KEYTRUDA® and OPDIVO®. Both have shown to restore the tumor-eradicating immune responses, improve survival, and have cured a number of patients (Carretero-Gonzalez et al., Oncotarget, 9(9): p. 8706-8715, 2018). However, the development of approaches that target PD-1 and other immune molecules for dogs with cancer have been limited, as previous canine-specific agents had limited efficacy and had a high cost of development (Klingemann, Frontiers in Immunology 9(133): 1-5, 2018). To more effectively treat canine cancers, new agents specific for canine immune targets like PD-1 are needed.

SUMMARY $V_HH$ monoclonal antibodies are disclosed that specifically bind to canine PD-1. Antigen binding fragments of these antibodies are also disclosed, as are bispecific antibodies including these $V_HH$ monoclonal antibodies.

In some embodiments, nucleic acid molecules are disclosed that encode these $V_HH$ monoclonal antibodies. In further embodiments, expression vectors are disclosed that include the nucleic acid molecules, and isolated host cells including these vectors.

In more embodiments, methods are also disclosed for using these $V_HH$ monoclonal antibodies, antigen binding fragments thereof, and bispecific antibodies such as for increasing an immune response and/or treating a tumor in a canine subject, for example a dog. Methods are also for detecting canine PD-1 in a biological sample from a canine subject.

The foregoing and other features and advantages of the invention will become more apparent from the following detailed description of several embodiments which proceeds with reference to the accompanying figures.

BRIEF DESCRIPTION OF THE FIGURES

FIG. 2 is Table 1, Results of Analysis of Binding Affinities and Inhibition of PD-1/PD-L1 Binding. Nanobody PD-1 binding or blockade of PD-L1 was carried out using antibodies specific for nanobodies or canine PD-L1, respectively. A colorimetric assay with a peroxidase-based enzyme, determined candidate nanobody binding affinity to canine PD-1 as described in Bobrovnik, J Biochem Biophys Methods. 30; 57(3): p. 213-36, 2003. Blockade of PD-L1 interactions with PD-1 were determined by signal reduction of bound PD-1 to PD-L1 coated plates with increasing amounts of free nanobody added.

FIGS. 3A-3B are sequence comparisons of the $V_HH$ monoclonal antibody amino acid sequences. In these figures, SEQ ID NOs: 1, 5, 9, 13, 17, 21, 25, 29, 33, 37, 41, 45, 49, 53, 57, 61, 65, 69, 73, 77, 81, 85, 89, 93, 97, 101, 105, 109, and 113 are shown (labeled by antibody name). The locations of the complementarity determining regions (CDRs) framework regions (FRs) are shown. The consensus sequence in FIG. 3A is SEQ ID NO: 117. The top consensus sequence in FIG. 3B is SEQ ID NO: 118, and the lower consensus sequence is SEQ ID NO: 119. In the sequences presented, the CDR1 is single underlined, the CDR2 is double underlined, and the CDR3 is italicized.

FIG. 5. PD-1/PD-L1 inhibition by a single nanobody or linked diabody

SEQUENCE LISTING

Figure 1:
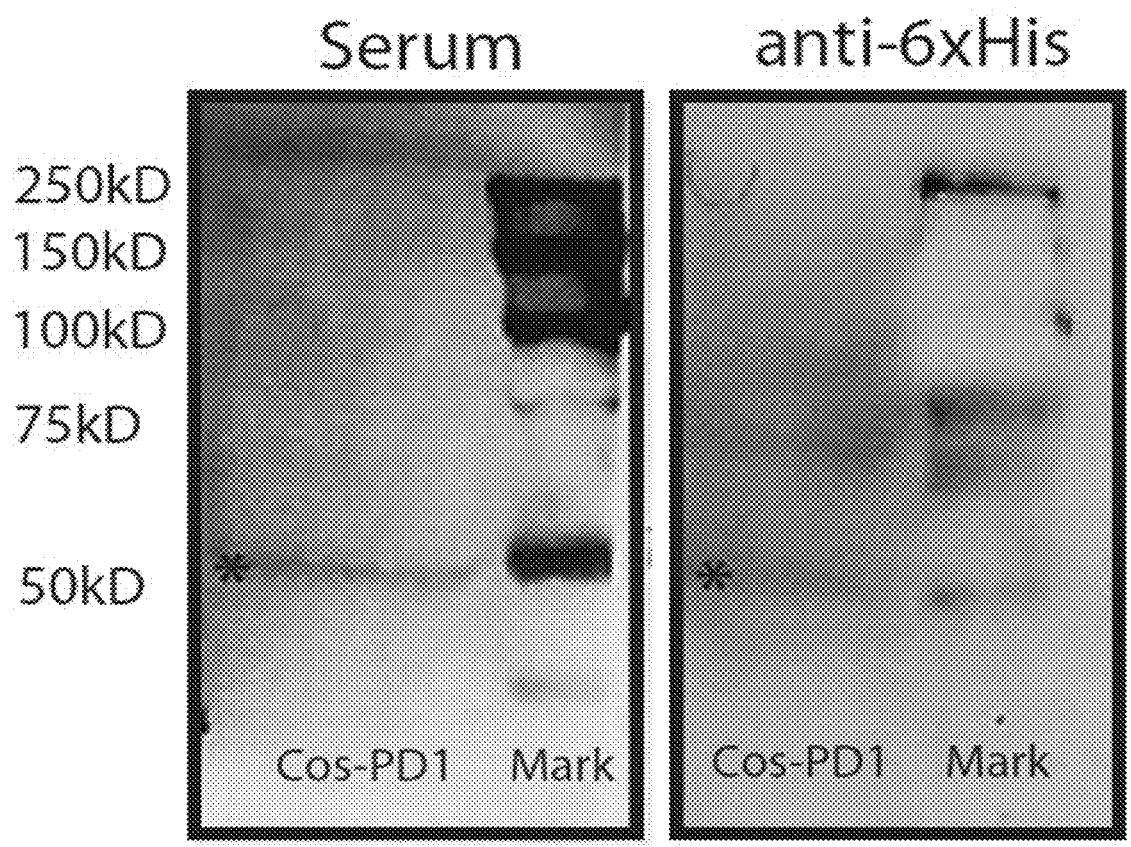
FIG. 1: Detection of Canine PD-1 Reactive Alpaca Sera by Western Blot. Protein lysates from Cos cells expressing a recombinant 6×His-tagged canine PD-1 construct (Cos PD-1) were fractionated on SDS-PAGE electrophoresis gel along with molecular weight markers (Mark) and transferred to nitrocellulose membranes. Membranes were separated and incubated with either serum from an alpaca immunized with canine PD-1 DNA vaccine or anti-6×His HRP (horse radish peroxidase) antibody conjugate in TBS-tween buffer. A secondary anti-camelid antibody-HRP conjugate was used to detect camelid antibody binding. Reactivity of the PD-1 protein was observed at the same molecular mass position in both blots corresponding to PD-1 (*).

The nucleic and amino acid sequences listed are shown using standard letter abbreviations for nucleotide bases, and one letter code for amino acids. Only one strand of each nucleic acid sequence is shown, but the complementary strand is understood as included by any reference to the displayed strand. The Sequence Listing is submitted as an ASCII text file 245-102374-02_Sequence_Listing, Aug. 13, 2020, 53.5 KB, which is incorporated by reference herein. In the accompanying sequence listing:

In the first five V$_H$1 domain sequences, the CDR1 is underlined, the CDR2 is double underlined, and the CDR3 is wiggly underlined. These V$_H$H domain sequences, and the locations of the CDRs, are also shown in FIG. 3.

SEQ ID NO: 1 is the amino acid sequence of a V$_H$H domain of NAN4 (5A1).

QVQLQASGGGLVQPGGSLTLSCAASG [illegible] WYRQGPGKQREFVA [illegible]

YADSAKGRFTISRDNAKNTVYLQMNSLKPEDTAVYYCNA [illegible] WGQGTQVG

SEQ ID NO: 2 is the amino acid sequence of the CDR1 of NAN4 (5A1).
SEQ ID NO: 3 is the amino acid sequence of the CDR2 of NAN4 (5A1).
SEQ ID NO: 4 is the amino acid sequence of the CDR3 of NAN4 (5A1).
SEQ ID NO: 5 is the amino acid sequence of a V$_H$H domain of NAN7/8 (5A5).

QVQLQASGGGLVEPGGSLRLSCAASG [illegible] WYRQAPGKERELVA [illegible]

YADSVKGRFTISRDNAKNTAYLQMDSLKAEDTGVYYCNA [illegible] WGQGTQVG

SEQ ID NO: 6 is the amino acid sequence of the CDR1 of NAN7/8 (5A5).
SEQ ID NO: 7 is the amino acid sequence of the CDR2 of NAN7/8 (5A5).
SEQ ID NO: 8 is the amino acid sequence of the CDR3 of NAN7/8 (5A5).
SEQ ID NO: 9 is the amino acid sequence of a V$_H$H domain of NAN10 (4B4).

QVQLQASGGGLVQGGESLRLSCAASG [illegible] WYRQAPGKEREFVA [illegible]

YLDSVKGRFTISRDNTKDTVYLQMNTLKPEDTAVYYCNA [illegible] WGQGTQVG

SEQ ID NO: 10 is the amino acid sequence of the CDR1 of NAN10 (4B4).
SEQ ID NO: 11 is the amino acid sequence of the CDR2 of NAN10 (4B4).
SEQ ID NO: 12 is the amino acid sequence of the CDR3 of NAN10 (4B4).
SEQ ID NO: 13 is the amino acid sequence of a V$_H$H domain of NAN15 (4B2).

QVQLQASGGGLVQPGEHLLLSCAASG [illegible] WYRQAPGKEREKVA [illegible]

YADSVKGRFTISRENAKNTLYLQMNSLKPEDTALYFCAK [illegible] WGQGTQVG

SEQ ID NO: 14 is the amino acid sequence of the CDR1 of NAN15 (4B2).
SEQ ID NO: 15 is the amino acid sequence of the CDR2 of NAN15 (4B2).
SEQ ID NO: 16 is the amino acid sequence of the CDR3 of NAN15 (4B2).
SEQ ID NO: 17 is the amino acid sequence of a V$_H$H domain of NAN28(1B5).

QVQLVQASGGGLVQPGGSLRLSCAAS [illegible] WVRQAPGKGLEWVA [illegible]

YADSVKGRFTISRDNTKNTVYLQMNNLKPEDTAVYYCNA [illegible] WGQGTQVG

SEQ ID NO: 18 is the amino acid sequence of the CDR1 of NAN28(1B5).
SEQ ID NO: 19 is the amino acid sequence of the CDR2 of NAN28(1B5).
SEQ ID NO: 20 is the amino acid sequence of the CDR3 of NAN28(1B5).
The following sequences are shown in FIG. 3:
SEQ ID NO: 21 is the amino acid sequence of a $V_HH$ domain of NAN 1.
SEQ ID NOs: 22, 23, and 24 are the amino acid sequences of a CDR1, CDR2, and CDR3 of NAN1, respectively.
SEQ ID NO: 25 is the amino acid sequence of a $V_HH$ domain of NAN 2.
SEQ ID NOs: 26, 27, and 28 are the amino acid sequences of a CDR1, CDR2, and CDR3 of NAN2, respectively.
SEQ ID NO: 29 is the amino acid sequence of a $V_HH$ domain of NAN3.
SEQ ID NOs: 30, 31 and 32 are the amino acid sequences of a CDR1, CDR2, and CDR3 of NAN3, respectively.
SEQ ID NO: 33 is the amino acid sequence of a $V_HH$ domain of NAN5.
SEQ ID NOs: 34, 35 and 36 are the amino acid sequences of a CDR1, CDR2, and CDR3 of NAN5, respectively.
SEQ ID NO: 37 is the amino acid sequence of a $V_HH$ domain of NAN6.
SEQ ID NOs: 38, 39 and 40 are the amino acid sequences of a CDR1, CDR2, and CDR3 of NAN6, respectively.
SEQ ID NO: 41 is the amino acid sequence of a $V_HH$ domain of NAN5.
SEQ ID NOs: 42, 43 and 44 are the amino acid sequences of a CDR1, CDR2, and CDR3 of NAN9, respectively.
SEQ ID NO: 45 is the amino acid sequence of a $V_HH$ domain of NAN11.
SEQ ID NOs: 46, 47 and 48 are the amino acid sequences of a CDR1, CDR2, and CDR3 of NAN11, respectively.
SEQ ID NO: 49 is the amino acid sequence of a $V_HH$ domain of NAN12.
SEQ ID NOs: 50, 51 and 52 are the amino acid sequences of a CDR1, CDR2, and CDR3 of NAN12, respectively.
SEQ ID NO: 53 is the amino acid sequence of a $V_HH$ domain of NAN13.
SEQ ID NOs: 54, 55 and 56 are the amino acid sequences of a CDR1, CDR2, and CDR3 of NAN13, respectively.
SEQ ID NO: 57 is the amino acid sequence of a $V_HH$ domain of NAN14.
SEQ ID NOs: 58, 59 and 60 are the amino acid sequences of a CDR1, CDR2, and CDR3 of NAN14, respectively.
SEQ ID NO: 61 is the amino acid sequence of a $V_HH$ domain of NAN16.
SEQ ID NOs: 62, 63 and 64 are the amino acid sequences of a CDR1, CDR2, and CDR3 of NAN16, respectively.
SEQ ID NO: 65 is the amino acid sequence of a $V_HH$ domain of NAN17.
SEQ ID NOs: 66, 67, and 68 are the amino acid sequences of a CDR1, CDR2, and CDR3 of NAN17, respectively.
SEQ ID NO: 69 is the amino acid sequence of a $V_HH$ domain of NAN18.
SEQ ID NOs: 70, 71 and 72 are the amino acid sequences of a CDR1, CDR2, and CDR3 of NAN18, respectively.
SEQ ID NO: 73 is the amino acid sequence of a $V_HH$ domain of NAN19.
SEQ ID NOs: 74, 75 and 76 are the amino acid sequences of a CDR1, CDR2, and CDR3 of NAN19, respectively.
SEQ ID NO: 77 is the amino acid sequence of a $V_HH$ domain of NAN20.
SEQ ID NOs: 78, 79 and 80 are the amino acid sequences of a CDR1, CDR2, and CDR3 of NAN20, respectively.
SEQ ID NO: 81 is the amino acid sequence of a $V_HH$ domain of NAN21.
SEQ ID NOs: 82, 83, 84 are the amino acid sequences of a CDR1, CDR2, and CDR3 of NAN21, respectively.
SEQ ID NO: 85 is the amino acid sequence of a $V_HH$ domain of NAN22.
SEQ ID NOs: 86, 87, and 88 are the amino acid sequences of a CDR1, CDR2, and CDR3 of NAN22, respectively.
SEQ ID NO: 89 is the amino acid sequence of a $V_HH$ domain of NAN23.
SEQ ID NOs: 90, 91 and 92 are the amino acid sequences of a CDR1, CDR2, and CDR3 of NAN23, respectively.
SEQ ID NO: 93 is the amino acid sequence of a $V_HH$ domain of NAN24.
SEQ ID NOs: 94, 95, 96 are the amino acid sequences of a CDR1, CDR2, and CDR3 of NAN24, respectively.
SEQ ID NO: 97 is the amino acid sequence of a $V_HH$ domain of NAN25.
SEQ ID NOs: 98, 99 and 100 are the amino acid sequences of a CDR1, CDR2, and CDR3 of NAN25, respectively.
SEQ ID NO: 101 is the amino acid sequence of a $V_HH$ domain of NAN26.
SEQ ID NOs: 102, 103, and 104 are the amino acid sequences of a CDR1, CDR2, and CDR3 of NAN26, respectively.
SEQ ID NO: 105 is the amino acid sequence of a $V_HH$ domain of NAN27.
SEQ ID NOs: 106, 107 and 108 are the amino acid sequences of a CDR1, CDR2, and CDR3 of NAN27, respectively.
SEQ ID NO: 109 is the amino acid sequence of a $V_HH$ domain of NAN29.
SEQ ID NOs: 110, 111 and 112 are the amino acid sequences of a CDR1, CDR2, and CDR3 of NAN29, respectively.
SEQ ID NO: 113 is the amino acid sequence of a $V_HH$ domain of NAN30.
SEQ ID NOs: 114, 115 and 116 are the amino acid sequences of a CDR1, CDR2, and CDR3 of NAN30, respectively.
SEQ ID NOs: 117-119 are consensus sequences of a $V_HH$ domain of a monoclonal antibody that specifically binds canine PD-1.

DETAILED DESCRIPTION OF SEVERAL EMBODIMENTS

The FDA approval in 2012 of YEVOY® (Ipilimumab), a checkpoint inhibitor-based immunotherapeutic (IT) for the treatment of late stage melanoma, spawned the growth of therapeutics designed to enhance immune responses to tumors. This agent is immensely successful in the treatment, and even eradication, of some human cancers. Unfortunately, this platform of monoclonal antibodies (MAbs) can induce severe life-threating reactions to the drug and a significant percentage of patients must discontinue treatment. More commonly known as "serum sickness," which is similar to an allergic reaction, a patient's immune system recognizes and produces antibodies against the Mab drug. These anti-drug antibodies are long lived, reduces the efficacy of the drug greatly increases the risk of adverse reaction to both subsequent treatments Mab drug as well as other immunotherapy that utilize the same Mab platform. In addition, these drugs are specific to human PD-1, and cannot be used in veterinary subjects.

mAbs have a molecular weight of 150-160 kDa. In contrast, VHH antibodies, are also referred to as "nanobodies," are small antibody-like molecules, with a molecular weight of 12-15 kDa. Camelids (alpaca, llamas and camels)

and cartilaginous fishes naturally produce nanobodies that are a peptide chain of ~110 amino acids that exhibit similar affinity to target (drug-like targeting properties) as the much larger Mab. These nanobodies include only a single heavy chain variable ($V_HH$) domain with three complementarity determining regions (CDRs). There are unique properties of these nanobodies, as they are heat-, detergent-, urea- and acid-resistant. In addition, they have superior solubility and permeability of tissues and tumors, short plasma half-life and renal elimination. Furthermore, these $V_HH$ monoclonal antibodies do not trigger the complement system that can result in cytotoxicity. Therefore, the safety profile of these $V_HH$ monoclonal antibodies disclosed herein is superior and can reduce adverse events and limit reactions that result from the extended half-life of a Mab. The disclosed $V_HH$ monoclonal antibodies and antigen binding fragments thereof also bind canine PD-1 with a high affinity.

Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

About: Unless context indicated otherwise, "about" refers to plus or minus 5% of a reference value. For example, "about" 100 refers to 95 to 105.

Administration: The introduction of a composition into a subject by a chosen route. Administration can be local or systemic. For example, if the chosen route is intravenous, the composition (such as a composition including a disclosed $V_HH$ monoclonal antibody or antigen binding fragment, etc.) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Agent: Any substance or any combination of substances that is useful for achieving an end or result; for example, a substance or combination of substances useful for inhibiting tumor growth or metastasis in a subject. Agents include $V_HH$ monoclonal antibodies, antigen binding fragments thereof, other proteins, nucleic acid molecules, compounds, small molecules, organic compounds, inorganic compounds, or other molecules of interest. An agent can include a therapeutic agent (such as a chemotherapeutic agent), a diagnostic agent or a pharmaceutical agent. The skilled artisan will understand that particular agents may be useful to achieve more than one result.

Amino acid substitutions: The replacement of one amino acid in a polypeptide with a different amino acid or with no amino acid (i.e., a deletion). In some examples, an amino acid in a polypeptide is substituted with an amino acid from a homologous polypeptide, for example, and amino acid in a $V_HH$ monoclonal antibody that specifically binds canine PD-1 or antigen binding fragment thereof can be substituted with the corresponding amino acid from another $V_HH$ monoclonal antibody that specifically binds canine PD-1 or antigen binding fragment thereof.

Amplification: A technique that increases the number of copies of a nucleic acid molecule (such as an RNA or DNA). An example of amplification is the polymerase chain reaction, in which a biological sample is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Publication No. WO 90/01069; ligase chain reaction amplification, as disclosed in European Patent Publication EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals, such as camelids. Similarly, the term "subject" includes both human and veterinary subjects, such as dogs. A "canine" is an animal in the biological family Canidae, and includes domestic dogs, wolves, coyotes, foxes, jackals, and dingoes.

Antibody: A polypeptide substantially encoded by an immunoglobulin gene or immunoglobulin genes, or antigen binding fragments thereof, which specifically binds and recognizes an analyte (antigen) such as, but not limited to, canine PD-1. Immunoglobulin genes include the kappa, lambda, alpha, gamma, delta, epsilon and mu constant region genes, as well as the myriad immunoglobulin variable region genes.

In primates such as humans, and in many other mammalian species, a heavy and the light chain variable domain of an antibody combine to specifically bind the antigen. Generally, a naturally occurring primate (e.g., human) or canine immunoglobulin has heavy (H) chains and light (L) chains interconnected by disulfide bonds. There are two types of light chain, lambda (λ) and kappa (κ). In humans, there are five main heavy chain classes (or isotypes) which determine the functional activity of an antibody molecule: IgM, IgD, IgG, IgA and IgE. Antibodies can be class switched. A camelid $IgG_2$ and $IgG_3$ has only a heavy chain, and no light chain.

Naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). Specifically, antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

In response to antigenic challenge or vaccination, camelids produce both conventional heterotetrameric antibodies, where variable regions of heavy and light chains combine to form an antigen binding site and that also produce unique heavy-chain antibodies (HCAbs). HCAbs consist of only one antigen binding domain named VHH (variable domain of the heavy chain of the HCAbs). The VHH chain of these homodimeric antibodies are structurally and functionally similar to a Fab fragment of conventional antibodies. The structure of the VHH and variability within the sequence of the V domain is localized in three hypervariable regions (HV) surrounded by more conserved framework regions (FR) all coded in the H-locus of the camelid genome.

Conventional camelid antibodies, e.g. $IgG_1$, are formed following gene rearrangement of the light chain locus and the H-locus (IGHV, D and J) and class switching along with dedicated IGHG1 genes (Constant heavy 1 (CH1 exon), hinge region and CH2 and CH3 exons). In other camelid B cells producing HCAbs, a different Immunoglobulin Heavy Chain Variable Region (IGHV3H) is rearranged to one D and one J element to form a VHH. The CH1 exon region is eliminated during RNA Splicing and joined to the VHH to produce homodimeric heavy chain antibodies comprised of only heavy chains containing VHH, hinge and CH2 and CH3 domains.

In some embodiments, such as in camelids, only the heavy chain variable domain is required for antigen binding. The smallest intact functional antigen-binding fragment of an HCAbs is the single domain VHH, which includes the framework regions (FRs) and complementary determining regions (CDRs). These are often expressed as recombinant proteins in phage display libraries for antigen-specific selection. Antigen reactive single domain VHH sequences are also known as Nanobody. (Muyldermans, S., 2013 Annu. Rev. BioChem 82:775-797 Nanobodies: Natural Single-Domain Antibodies).

References to "$V_H$" or "VH" refer to the variable region of an immunoglobulin heavy chain, including that of an antibody fragment. References to "$V_L$" or "VL" refer to the variable region of an immunoglobulin light chain, such as in a primate antibody.

References to "$V_HH$" or "VHH" refer to the singe heavy chain variable region of a "$V_HH$ monoclonal antibody." "$V_HH$ monoclonal antibodies" include two constant domains in the Fc and the $V_HH$ domain. $V_HH$ monoclonal antibodies lack the CH1 domain of conventional (two variable domain) antibodies (Muyldermans, Annu. Rev. Biochem. 2013. 82:775-97, 2013). In some embodiments, a $V_HH$ monoclonal antibody can be an IgG. A $V_HH$ monoclonal antibody is generally composed of only one polypeptide chain of 15 kDa, includes the $V_HH$ domain with the three CDRs, and has antigen-binding capacity.

In all species, heavy (and light) chain variable domains contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space. The CDRs are primarily responsible for antigen binding.

The CDRs are typically referred to as CDR1, CDR2, and CDR3 (from the N-terminus to C-terminus) and are also typically identified by the chain in which the particular CDR is located. For two chain antibodies, a heavy chain (H) CDR3 is located in the variable domain of the heavy chain of the antibody in which it is found, whereas a light chain (L) CDR1 is the CDR1 from the variable domain of the light chain of the antibody in which it is found. Light chain CDRs are sometimes referred to as CDR L1, CDR L2, and CDR L3. Heavy chain CDRs are sometimes referred to as CDR H1, CDR H2, and CDR H3. $V_HH$ monoclonal antibodies have only a heavy chain (no light chain), and thus include only one CDR1, CDR2 and CDR3.

Generally, the CDR3 is primarily responsible for antigen specificity. The sequences of the framework regions of different light or heavy chains are relatively conserved within a species. The framework region of an antibody, that is the combined framework regions of the constituent light and heavy chains, serves to position and align the CDRs in three-dimensional space.

Any variable domain includes in an N- to C-direction, the following structural regions: N-FR1-CDR1-FR2-CDR2-FR3-CDR3-FR4-C, wherein FR denotes a framework region amino acid sequence and CDR denotes a complementary determining region amino acid sequence (see, e.g., Kabat et al., Sequences of Proteins of Immunological Interest, U.S. Department of Health and Human Services, 1991). In specific non-limiting examples, the CDR3 comprises a llama CDR3 $V_HH$ domain amino acid sequence; and wherein the antibody binds to canine PD-1.

In primates and mammalian species wherein the antibodies include a light chain, the extent of the framework region and CDRs have been defined (see, Kabat et al., Sequences of Proteins of Immunological Interest, U.S. Department of Health and Human Services, 1991, which is hereby incorporated by reference in its entirety). The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia and Lesk, J. Mol. Biol., 196: 901-17, 1987), the loop equivalent to CDR-H1 extends from residue 26 to residue 32. Thus "CDR-H1", as used herein, comprises residues 26 to 33, as described by a combination of the Kabat numbering system and Chothia's topological loop definition. In antibodies (such as primate antibodies) that include a light chain, such as a primate antibody, the CDRs of the light chain variable domain are located at residues 24-34 (CDR-L1), residues 50-56 (CDR-L2) and residues 89-97 (CDR-L3) according to the Kabat numbering system. Lefranc, et al. ("IMGT unique numbering for immunoglobulin and T cell receptor variable domains and Ig superfamily V-like domains," Dev. Comp. Immunol., 27:55-77, 2003) discloses the "IMGT" numbering scheme for CDRs. The Kabat database is now maintained online. For single chain $V_HH$ monoclonal antibodies, the location of camelid CDRs can also be determined (see, for example, Sircar et al., J. Immunol. 186: 6357-6367, 2011). A program to determine camelid antibody structure, the RosettaAntibody program, is available on the internet. This program identifies the CDRs of a $V_HH$ domain. In addition, the Institute collection and analysis of Nanobodies (iCAN): a comprehensive database and analysis platform for nanobodies (Zou, J et al 2017 BMC Genomics 18 Article number 797, 2017, incorporated by reference, can also be used.

A "monoclonal antibody" can be an antibody produced by a single clone of B-lymphocytes or by a cell into which the heavy chain gene (and optionally a light chain gene, such as for a primate antibody) of a single antibody have been transfected. A "polyclonal" antibody preparation typically includes different antibodies directed against different determinants (epitopes), each monoclonal antibody of a monoclonal antibody preparation is directed against a single determinant on an antigen. However, the modifier "monoclonal" indicates the character of the antibody as being obtained from a substantially homogeneous population and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject.

Monoclonal antibodies can have conservative amino acid substitutions which have substantially no effect on antigen binding or other immunoglobulin functions. (See, for example, Greenfield (Ed.), *Antibodies: A Laboratory Manual*, $2^{nd}$ ed. New York: Cold Spring Harbor Laboratory Press, 2014). In some embodiments, the $V_HH$ monoclonal antibodies can be produced as recombinant monoclonal antibodies or antigen binding fragments in different expression platforms, avoiding the use of hybridomas and mice. $V_HH$ monoclonal antibodies can be include a heterologous framework region and can be chimeric. In some embodiments, the heterologous framework region is a dog framework region.

Binding affinity: Affinity of an antibody, such as a $V_HH$ monoclonal antibody, or antigen binding fragment thereof, for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay or by Plasmon resonance in a BIOCORE. In several examples, a high binding affinity is at least about $1\times10^{-8}$ M. In other embodiments, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$ M.

The antigen specificity and affinity of $V_HH$ monoclonal antibodies from immune libraries are of good quality. Kinetick (k)on and koff rate constants are generally in the range of $10^5$ to $10^6$ $M^{-1}s^{-1}$ and $10^{-2}$ to $10^{-4}$ $s^{-1}$, respectively, such that low nanomolar or even picomolar equilibrium dissociation constants are obtained. Such affinity parameters are excellent for most applications (Muyldermans, Annu. Rev. Biochem. 2013. 82:775-97, 2013).

Biological sample: A sample obtained from a subject. Biological samples include all clinical samples useful for detection in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a tumor, such as an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy. The biological sample can include T cells.

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be $V_HH$ domains, monoclonal antibodies, antigen-binding fragments (e.g., Fab, scFv, ds-scFv), or combinations thereof. A bispecific antibody can include one or more constant domains but does not necessarily include a constant domain. Bispecific antibodies include diabodies.

Carcinoma: A malignant tumor including transformed epithelial cells. Non-limiting examples of carcinomas include adenocarcinoma, squamous cell carcinoma, anaplastic carcinoma and large and small cell carcinoma.

Chemotherapeutic agent: Any chemical agent with therapeutic usefulness in the treatment of diseases characterized by abnormal cell growth. For example, chemotherapeutic agents are useful for the treatment of cancer, including osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, and/or a hematologic malignancy. In one embodiment, a chemotherapeutic agent is an agent of use in treating a carcinoma. Particular examples of additional therapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. In one embodiment, a chemotherapeutic agent is a radioactive compound. Other examples include the anti-neoplastic drugs 5-fluorouracil (5-FU) and IRT. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemo-*

*therapy and Biotherapy: Principles and Practice* (4th ed.). Philadelphia: Lippincott Willians & Wilkins, 2005; Skeel, *Handbook of Cancer Chemotherapy* (6th ed.). Lippincott Williams & Wilkins, 2003). Combination chemotherapy is the administration of more than one agent to treat cancer.

Chimeric antibody: An antibody which includes sequences derived from two different antibodies, such as from different species. In some examples, a chimeric antibody includes one or more CDRs and/or framework regions from one llama $V_HH$ domains (or monoclonal antibodies) and CDRs and/or framework regions from another llama $V_HH$ domain or a $V_H$ from a canine antibody.

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, *Antibodies, A Laboratory Manual*, $2^{nd}$ ed. Cold Spring Harbor Publications, New York (2013) for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Conjugate: A complex of two molecules linked together, for example, linked together by a covalent bond. In one embodiment, an antibody is linked to an effector molecule such as a label; for example, an antibody that specifically binds to canine PD-1 covalently linked to a label. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to interact with a target protein. For example, a canine PD-1-specific $V_HH$ monoclonal antibody can include up to 1, 2, 3, 4, 5, 6, 7, 8, 9, or up to 10 conservative substitutions compared to a reference antibody sequence and retain specific binding activity for canine PD-1. The term conservative variation also includes the use of a substituted amino acid in place of an unsubstituted parent amino acid.

Individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the anti-canine PD-1 $V_HH$ monoclonal antibody, or antigen binding fragment thereof, such as the ability to specifically bind to canine PD-1 or bind to a cancer cell expressing canine PD-1. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as a peptide, that contacts another polypeptide. Contacting can also include contacting a cell for example by placing a polypeptide in direct physical association with a cell.

Control: A reference standard. In some embodiments, the control is a negative control sample obtained from a healthy patient, such as a canine subject without a tumor. In other embodiments, the control is a positive control sample obtained from a patient known to have increased T cells that express canine PD-1, or recombinantly produced purified canine PD-1. In still other embodiments, the control is a historical control or standard reference value or range of values (such as a previously tested control sample, such as a group of patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%. In some embodiments, tumor growth, volume and/or metastasis is decreased.

Decrease or Reduce: To reduce the quality, amount, or strength of something; for example, a reduction in tumor burden. In one example, a therapy reduces a tumor (such as the size of a tumor, the number of tumors, the metastasis of a tumor, or combinations thereof), or one or more symptoms associated with a tumor, for example as compared to the response in the absence of the therapy. In a particular example, a therapy decreases the size of a tumor, the number of tumors, the metastasis of a tumor, or combinations thereof, subsequent to the therapy, such as a decrease of at least 10%, at least 20%, at least 30%, at least 40%, at least 50%, at least 60%, at least 70%, at least 80%, or at least 90%. Such decreases can be measured using the methods disclosed herein.

Degenerate variant: In the context of the present disclosure, a "degenerate variant" refers to a polynucleotide encoding a polypeptide (such as an antibody) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Methods for using detectable markers and guidance in the choice of detectable markers appropriate for various purposes are discussed for example in Green and Sambrook (*Molecular Cloning: A Laboratory Manual*, 4$^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Detecting: To identify the existence, presence, or fact of something.

Effective amount: A quantity of a specific substance sufficient to achieve a desired effect in a subject to whom the substance is administered, such as a therapeutically effective amount, for treatment. For instance, this can be the amount of a VHH monoclonal antibody or antigen binding fragment thereof necessary to inhibit tumor growth and/or metastasis, or to measurably alter outward symptoms of the tumor.

In some embodiments, administration of an effective amount of a disclosed antibody or antigen binding fragment that binds to canine PD-1 can reduce or inhibit an tumor growth, tumor metastasis, or tumor volume by a desired amount, for example by at least 10%, at least 20%, at least 50%, at least 60%, at least 70%, at least 80%, at least 90%, at least 95%, at least 98%, or even at least 100% (elimination of the tumor), as compared to a suitable control.

The effective amount of an antibody or antigen binding fragment that specifically binds to canine PD-1 that is administered to a subject will vary depending upon a number of factors associated with that subject, for example the overall health and/or weight of the subject. An effective amount can be determined by varying the dosage and measuring the resulting response, such as, for example, a reduction in tumor burden. Effective amounts also can be determined through various in vitro, in vivo or in situ immunoassays.

An effective amount encompasses a fractional dose that contributes in combination with previous or subsequent administrations to attaining an effective response. For example, an effective amount of an agent can be administered in a single dose, or in several doses, for example daily, during a course of treatment lasting several days or weeks. However, the effective amount can depend on the subject being treated, the severity and type of the condition being treated, and the manner of administration. A unit dosage form of the agent can be packaged in an amount, or in multiples of the effective amount, for example, in a vial (e.g., with a pierceable lid) or syringe having sterile components.

Effector molecule: A molecule intended to have or produce a desired effect; for example, a desired effect on a cell to which the effector molecule is targeted. Effector molecules include such molecules as chemical compounds, polypeptides, radioisotopes and small molecules. Non-limiting examples of effector molecules include toxins, chemotherapeutic agents and anti-angiogenic agents. The skilled artisan will understand that some effector molecules may have or produce more than one desired effect. In one example, an effector molecule is the portion of a chimeric molecule, for example a chimeric molecule that includes a disclosed antibody or fragment thereof, that is intended to have a desired effect on a cell to which the chimeric molecule is targeted.

Epitope: An antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on canine PD-1.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Expression control sequences can include appropriate promoters, enhancers, transcription terminators, a start codon (ATG) in front of a protein-encoding gene, splicing signal for introns, maintenance of the correct reading frame of that gene to permit proper translation of mRNA, and a stop codon. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc region: The constant region of an antibody excluding the first heavy chain constant domain. Fc region generally refers to the last two heavy chain constant domains of IgA, IgD, and IgG, and the last three heavy chain constant domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region is typically understood to include immunoglobulin domains Cγ2 and Cγ3 and optionally the lower part of the hinge between Cγ1 and Cγ2. Although the boundaries of the Fc region may vary, the human IgG heavy chain Fc region is usually defined to include residues following C226 or P230 to the Fc carboxyl-terminus, wherein the numbering is according to Kabat. For IgA, the Fc region includes immunoglobulin domains Cα2 and Cα3 and optionally the lower part of the hinge between Cα1 and Cα2.

Heterologous: Originating from a different genetic source. A nucleic acid molecule that is heterologous to a cell originated from a genetic source other than the cell in which it is expressed. In one specific, non-limiting example, a heterologous nucleic acid molecule encoding a protein, such as an scFv, is expressed in a cell, such as a mammalian cell. Methods for introducing a heterologous nucleic acid molecule in a cell or organism are well known in the art, for example transformation with a nucleic acid, including electroporation, lipofection, particle gun acceleration, and homologous recombination.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

IgG: A polypeptide belonging to the class or isotype of antibodies that are substantially encoded by a recognized immunoglobulin gamma gene.

Immune complex: The binding of antibody or antigen binding fragment to antigen forms an immune complex. The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, radiography, and affinity chromatography.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogen: A compound, composition, or substance that can stimulate the production of antibodies or a T cell response in an animal, including compositions that are injected or absorbed into an animal, such as canine PD-1 coupled to a carrier. An immunogen can be used to produce antibodies, such as those disclosed herein.

Inhibiting or Treating a Tumor: A therapeutic intervention (for example, administration of a therapeutically effective amount of a $V_HH$ monoclonal antibody that specifically binds canine PD-1) that reduces a sign or symptom of a tumor. Treatment can also induce remission, such as reducing the size of a tumor. In particular examples, treatment includes inhibiting metastasis.

The term "reduces" is a relative term, such that an agent reduces a disease or condition if the disease or condition is quantitatively diminished following administration of the agent, or if it is diminished following administration of the agent, as compared to a reference agent. Reducing a sign or symptom refers to any observable beneficial effect of the treatment. Reducing a sign or symptom associated with a tumor can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having tumor), a reduction in the number of tumors or the time between removal of a tumor and the reappearance of the tumor, an improvement in the overall health or well-being of the subject, or by other parameters well known in the art that are specific to the particular tumor.

A "prophylactic" treatment is a treatment administered to a subject who does not exhibit signs of a tumor, but has a genetic predisposition to the tumor, or exhibits only early signs, such as a pre-cancerous lesion, for the purpose of decreasing the risk of developing the tumor. The term "prevents" does not necessarily mean that an agent completely eliminates the disease or condition, so long as at least one characteristic of the disease or condition is eliminated. Thus, a composition that reduces or prevents a tumor, can, but does not necessarily completely, prevent risk for developing a tumor.

Isolated: A biological component (such as a nucleic acid, peptide, protein or protein complex, for example a $V_HH$ monoclonal antibody or antigen binding fragment thereof) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Linker: A bi-functional molecule that can be used to link two molecules into one contiguous molecule, for example, to link an effector molecule to an antibody, or a detectable marker to an antibody. Non-limiting examples of peptide linkers include glycine-serine linkers.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as a Vial monoclonal antibody. The linkage can be either by chemical or recombinant means. "Chemical means" refers to a reaction between the antibody moiety and the effector molecule such that there is a covalent bond formed between the two molecules to form one molecule.

Nanoantibody or nanobody (Val): A nanobody is comprised of only one polypeptide chain and is considered the smallest known natural domain with full antigen-binding capacity (15 kDa) that includes three CDRs in a $V_HH$ domain. The DNA encoding the $V_HH$ domain may be obtained and modified by genetic engineering to yield a small recombinant protein having high affinity for a target, resulting in a low molecular weight antibody-derived protein known as a camelid "nanoantibody" or "nanobody" due to the small size. See U.S. Pat. No. 5,759,808 issued Jun. 2, 1998; see also Stijlemans et al., J Biol Chem 279: 1256-1261, 2004; Dumoulin et al., Nature 424: 783-788, 2003; Pleschberger et al., Bioconjugate Chem 14: 440-448, 2003; Cortez-Retamozo et al. Int J Cancer 89: 456-62, 2002; and Lauwereys et al., EMBO J 17: 3512-3520, 1998. As noted above, a $V_HH$ antibody includes in an N- to C-direction, the following structural domains regions: N-FR1-CDR1-FR2-CDR2-FR3-CDR3-FR4-C, wherein FR denotes a framework region amino acid sequence and CDR denotes a complementary determining region amino acid sequence, and C is the constant domain (see, e.g., Kabat et al., Sequences of Proteins of Immunological Interest, U.S. Department of Health and Human Services, 1991). These molecules do not include a light chain variable domain ($V_L$).

Neoplasia, cancer, or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue or can metastasize (or both) is referred to as "malignant."

Tumors of the same tissue type are primary tumors originating in a particular organ (such as head and neck, breast, or bladder). Tumors of the same tissue type may be divided into tumors of different sub-types. For examples, lung carcinomas can be divided into adenocarcinomas, small cell, squamous cell, or non-small cell tumors.

Examples of solid tumors, such as sarcomas (connective tissue cancer) and carcinomas (epithelial cell cancer), include fibrosarcoma, myxosarcoma, liposarcoma, chondrosarcoma, osteogenic sarcoma, and other sarcomas, synoviorna, mesothelioma, Ewing's tumor, leiomyosarcoma, rhabdomyosarcoma, colorectal carcinoma, lymphoid malignancy, pancreatic cancer, breast cancer, head and neck carcinoma, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In specific non-limiting examples, the lymphoid malignancy can be adult T cell leukemia, cutaneous T cell lymphoma, anaplastic large cell lymphoma, Hodgkin's lymphoma, or a diffuse large B cell lymphoma.

In some embodiments, a tumor is an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, and a hematologic malignancy.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A first sequence is an "antisense" with respect to a second sequence if a polynucleotide whose sequence is the first sequence specifically hybridizes with a polynucleotide whose sequence is the second sequence.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed antibodies and antigen binding fragments thereof.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Polypeptide modifications: Polypeptides and peptides, such as the antibodies disclosed herein can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Programmed Death (PD)-1: A protein that forms a complex with PD-L1 or PD-L2 protein and is involved in an immune response, such as the co-stimulation of T cells. Generally, PD-1 proteins are substantially identical to the naturally occurring (wild type) PD-1 (see, for example, Ishida et al. EMBO J. 11:3887-3895, 1992, Shinohara et al. Genomics 23:704-706, 1994; and U.S. Pat. No. 5,698,520, all incorporated by reference herein in their entirety). Exemplary sequences for canine PD-1 are disclosed, for example, in GENBANK® Accession Nos. AAEX03014566 (genomic) AB850882 and AB898677.1 (mRNA), and the corresponding protein sequences, as available on Aug. 1, 2019. In several examples, PD-1 signaling reduces, for example, CD8+ T cell cytoxicity by reducing T cell proliferation or altering cytokine production. Thus, a PD-1 polypeptide can reduce CD8+ T cell cytotoxic activity by at least 5%, 10%, 20%, 30%, 40%, 50%, 60%, 70%, 80%, 90%, or more than 100% below control levels as measured by any standard method.

As used herein, the term "activity" with respect to a PD-1 polypeptide or protein includes any activity which is inherent to the naturally occurring PD-1 protein, such as the ability to modulate an inhibitory signal in an activated immune cell, such as by engaging a natural ligand on an antigen presenting cell. Such modulation of an inhibitory signal in an immune cell results in modulation of proliferation and/or survival of an immune cell and/or cytokine secretion by an immune cell. PD-1 protein can also modulate a costimulatory signal by competing with a costimulatory receptor for binding of a B7 molecule. Thus, the term "PD-1 activity" includes the ability of a PD-1 polypeptide or protein to bind its natural ligand(s), the ability to modulate immune cell costimulatory or inhibitory signals, and the ability to modulate (decrease) the immune response.

"Reduce the activity of PD-1" refers to a decrease in the level or biological activity of PD-1 relative to the level or biological activity of PD-1 protein in a control, such as an untreated subject or sample. In specific examples, the level or activity is reduced by at least 10%, 20%, 30%, 40%, 50%, 60%, 70%, 80%, 90%, 100%, or even greater than 100%, relative to an untreated control. For example, the biological activity of PD-1 protein is reduced if binding of PD-1 protein to PD-L1, PD-L2, or both is reduced, thereby resulting in a reduction in PD-1 signaling and therefore resulting in an increase in CD8+ T cell cytotoxicity.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

As used herein, reference to "at least 80% identity" refers to "at least 80%, at least 85%, at least 90%, at least 91%, at least 92%, at least 93%, at least 94%, at least 95%, at least 96%, at least 97%, at least 98%, at least 99%, or even 100% identity" to a specified reference sequence. As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Specifically bind: When referring to an antibody or antigen binding fragment, refers to a binding reaction which determines the presence of a target protein in the presence of a heterogeneous population of proteins and other biologics. Thus, under designated conditions, an antibody binds preferentially to a particular target protein, peptide or polysaccharide (such as an antigen present on the surface of a T cell, for example canine PD-1) and does not bind in a significant amount to other proteins present in the sample or subject. Specific binding can be determined by standard methods. See Harlow & Lane, *Antibodies, A Laboratory Manual*, $2^{nd}$ ed., Cold Spring Harbor Publications, New York (2013), for a description of immunoassay formats and conditions that can be used to determine specific immunoreactivity.

With reference to an antibody-antigen complex, specific binding of the antigen and antibody has a $K_D$ of less than about $10^{-7}$ Molar, such as less than about $10^{-8}$ Molar, $10^{-9}$, or even less than about $10^{-10}$ Molar. $K_D$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

An antibody, such as a $V_HH$ monoclonal antibody, that specifically binds to an epitope on canine PD-1 is an antibody that binds substantially to canine PD-1 protein, including cells (such as T cells) or tissue expressing canine PD-1, substrate to which canine PD-1 is attached, or canine PD-1 protein in a biological specimen or isolated from a biological specimen. It is, of course, recognized that a certain degree of non-specific interaction may occur between an antibody and a non-target (such as a cell of the same tissue type that does not express canine PD-1). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein.

Subject: Living multi-cellular vertebrate organisms, a category that includes human and non-human mammals. In an example, a subject is a human. In a particular example, the subject has a cancer. In an additional example, a subject is selected that is in need of inhibiting of growth of a tumor or metastasis. For example, the subject has be diagnosed with a tumor that expresses PD-L1, such as an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy, and is in need of treatment.

T Cell: A white blood cell critical to the immune response. T cells include, but are not limited to, $CD4^+$ T cells and CD8+ T cells. A CD4+ T lymphocyte is an immune cell that expresses CD4 on its surface. These cells, also known as helper T cells, help orchestrate the immune response, including antibody responses as well as killer T cell responses. Th1 and Th2 cells are functional subsets of helper T cells. Th1 cells secrete a set of cytokines, including interferon-gamma, and whose principal function is to stimulate phagocyte-mediated defense against infections, especially related to intracellular microbes. Th2 cells secrete a set of cytokines, including interleukin (IL)-4 and IL-5, and whose principal functions are to stimulate IgE and eosinophil/mast cell-mediated immune reactions and to downregulate Th1 responses. Antigen specific CD8+ T cells become functionally tolerant ('exhausted') to a tumor antigen following the induction of the Programmed Death-1 polypeptide (PD-1). Accordingly, by reducing the expression or activity of PD-1, an immune response specific to an infectious agent or to tumor cells can be enhanced, see PCT Publication No. 2008/083174, incorporated herein by reference.

Therapeutic agent: Used in a generic sense, it includes treating agents, prophylactic agents, and replacement agents. A therapeutic agent is used to ameliorate a specific set of conditions in a subject with a disease or a disorder.

Treating or preventing a disease: Inhibiting the full development of a disease or condition, for example, in a subject who is at risk of or has a disease such as a tumor. "Treatment" refers to a therapeutic intervention that ameliorates a sign or symptom of a disease or pathological condition, such as a particular tumor type, after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Transformed cell: A transformed cell is a cell into which a nucleic acid molecule has been introduced by molecular biology techniques. As used herein, the term transformed and the like (e.g., transformation, transfection, transduction, etc.) encompasses all techniques by which a nucleic acid molecule might be introduced into such a cell, including transduction with viral vectors, transformation with plasmid vectors, and introduction of DNA by electroporation, lipofection, and particle gun acceleration.

Vector: An entity containing a nucleic acid molecule (such as a DNA or RNA molecule) bearing a promoter(s) that is operationally linked to the coding sequence of a protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can include one or more selectable marker genes and other genetic elements. Viral vectors are recombinant nucleic acid vectors having at least some nucleic acid sequences derived from one or more viruses. In some embodiments, a viral vector comprises a nucleic acid molecule encoding a disclosed antibody or antigen binding fragment that specifically binds canine PD-1.

Under conditions sufficient for: A phrase that is used to describe any environment that permits a desired activity.

II. Description of Several Embodiments

PD-1 molecules are members of the immunoglobulin gene superfamily. The human PD-1 has an extracellular region containing immunoglobulin superfamily domain, a transmembrane domain, and an intracellular region including an immunoreceptor tyrosine-based inhibitory motif (ITIM) ((Ishida et al., EMBO J. 11:3887, 1992; Shinohara et al., Genomics 23:704, 1994; U.S. Pat. No. 5,698,520). These features also define a larger family of molecules, called the immunoinhibitory receptors, which also includes gp49B, PIR-B, and the killer inhibitory receptors (KIRs) (Vivier and Daeron (1997) Immunol. Today 18:286). Without being bound by theory, it is believed that the tyrosyl phosphorylated ITIM motif of these receptors interacts with S112-domain containing phosphatase, which leads to inhibitory signals. A subset of these immuno-inhibitory receptors bind to major histocompatibility complex (MHC) molecules, such as the KIRs, and CTLA4 binds to B7-1 and B7-2.

In humans, PD-1 is a 50-55 kDa type I transmembrane receptor that was originally identified in a T cell line undergoing activation-induced apoptosis. PD-1 is expressed on T cells, B cells, and macrophages. The ligands for PD-1 are the B7 family members PD-ligand 1 (PD-L1, also known as B7-H1) and PD-L2 (also known as B7-DC). In canines, PD-1 sequences are disclosed at GENBANK® Accession No. A13898677.1 and A13850882.1 (Canine mRNA). AAEX03014566.1 (Canine Genomic), and corresponding protein sequences, as available on Aug. 1, 2019. Human PD-1 sequences are disclosed at GEN BANK No. AC131097 (Human genomic) and AK313848 (Human cDNA), as available on Aug. 1, 2019. The disclosed VHH antibodies antigen binding fragments thereof specifically bind canine PD-1.

In vivo, PD-1 is expressed on activated T cells, B cells, and monocytes. Experimental data implicates the interactions of PD-1 with its ligands in downregulation of central and peripheral immune responses. In particular, proliferation in wild-type T cells but not in PD-1-deficient T cells is inhibited in the presence of PD-L1. Additionally, PD-1-deficient mice exhibit an autoimmune phenotype.

Isolated $V_HH$, monoclonal antibodies and antigen binding fragments thereof that specifically bind canine PD-1 are disclosed herein. These $V_HH$, monoclonal antibodies and antigen binding fragments bind canine PD-1 and interfere with signaling by a ligand (such as PD-L1 or PD-L2) through PD-1. Thus, these $V_HH$, monoclonal antibodies and antigen binding fragments thereof can be used to increase cytotoxic activity of exhausted T cells.

Also disclosed herein are compositions including the antibodies and antigen binding fragments and a pharmaceutically acceptable carrier. Nucleic acids encoding the antibodies or antigen binding fragments, expression vectors including these nucleic acids, and isolated host cells that express the nucleic acids are also provided.

Compositions comprising the $V_HH$ monoclonal antibodies and antigen binding fragments thereof (such as the $V_HH$ domain), that specifically bind canine PD-1 can be used for research, diagnostic and therapeutic purposes. For example, the monoclonal antibodies can be used to increase cytotoxic T cell activity and can be used to treat a canine subject that has a tumor. In several embodiments, the V$_H$H monoclonal antibody, and antigen binding fragments thereof, that specifically bind canine PD-1, can be used to treat a tumor, such as, but not limited to an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy.

A. Antibodies and Antigen Binding Fragments

Figure 3A:
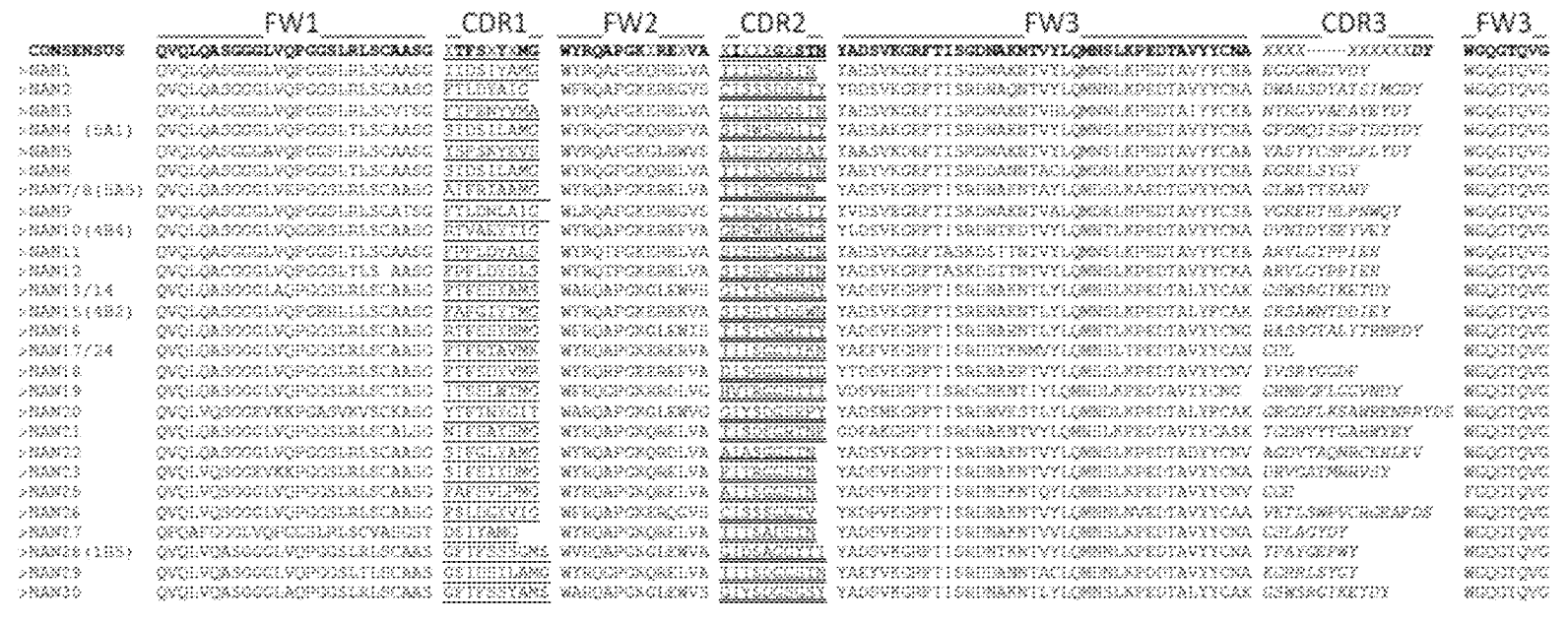
Figure 3B:
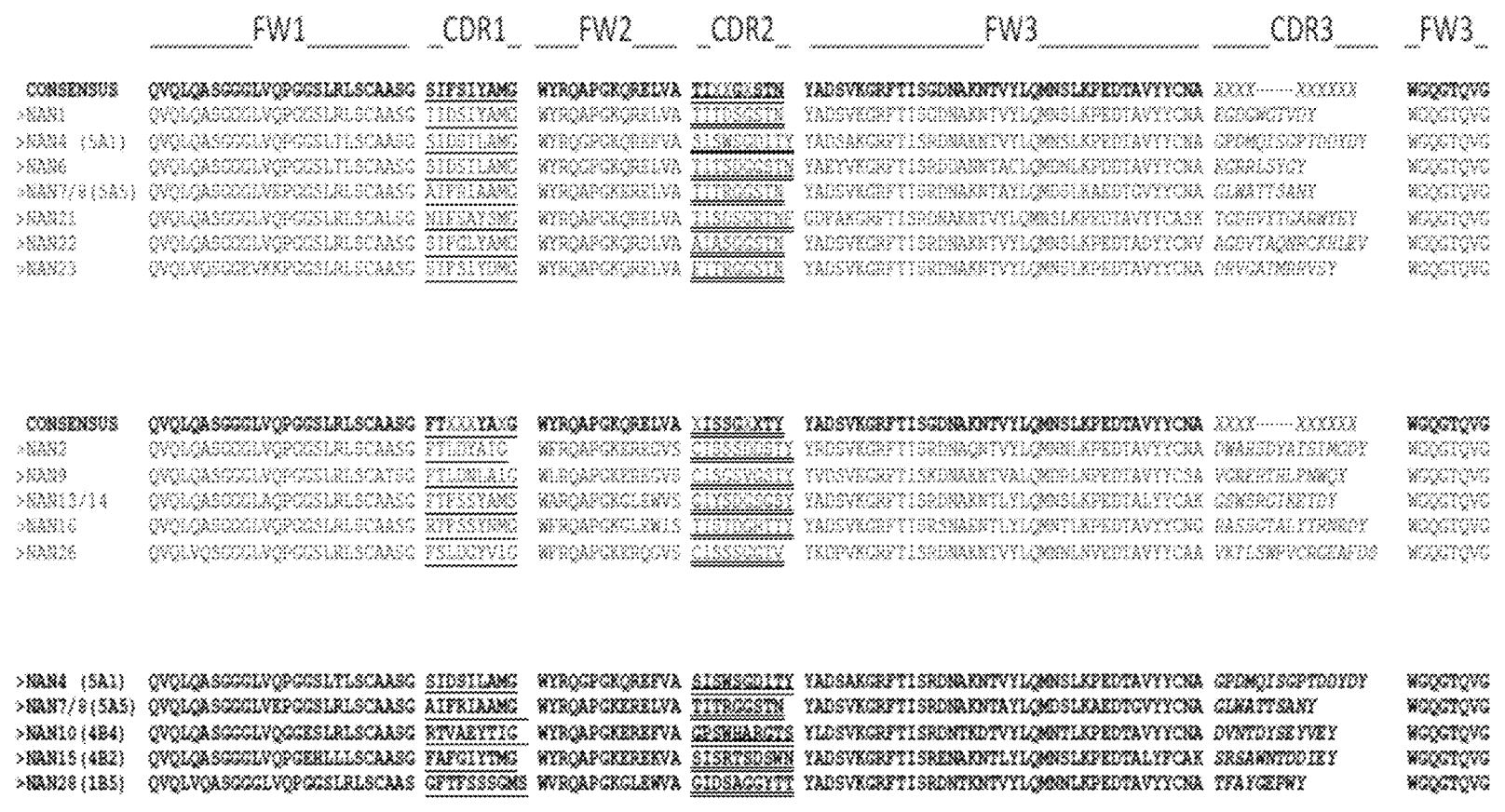

Disclosed are isolated Vial monoclonal antibodies, and antigen binding fragments thereof that include a V$_H$H domain, wherein the V$_H$H domain includes a complementarity determining region (CDR)1, a CDR2 and a CDR3, and wherein the V$_H$H monoclonal antibodies or antigen binding fragments specifically binds a canine programmed death (PD)-1, such as dog PD-1, see, for Example, FIGS. 3A-3B. In some embodiments, the V$_H$H monoclonal antibody or antigen binding fragment includes the CDR1, CDR2, or CDR3 of one of SEQ ID NOs: 1, 5, 9, 13, 17, 21, 25, 29, 33, 37, 41, 45, 49, 53, 57, 61, 65, 69, 73, 77, 81, 85, 89, 93, 97, 101, 105, 109, and 113, and specifically binds canine PD-1.

In specific non-limiting examples, a) the CDR1 includes the amino acid sequence of SEQ ID NO: 2, the CDR2 includes the amino acid sequence of SEQ ID NO: 3, and/or the CDR3 includes amino the amino acid sequence of SEQ ID NO: 4; b) the CDR1 includes the amino acid sequence of SEQ ID NO: 6, the CDR2 includes the amino acid sequence of SEQ ID NO: 7, and/or the CDR3 includes amino the amino acid sequence of SEQ ID NO: 8; c) the CDR1 includes the amino acid sequence of SEQ ID NO: 10, the CDR2 includes the amino acid sequence of SEQ ID NO: 11, and/or the CDR3 includes amino the amino acid sequence of SEQ ID NO: 12; d) the CDR1 includes the amino acid sequence of SEQ ID NO: 14, the CDR2 includes the amino acid sequence of SEQ ID NO: 15, and/or the CDR3 includes amino the amino acid sequence of SEQ ID NO: 16; or e) the CDR1 includes the amino acid sequence of SEQ ID NO: 18, the CDR2 includes the amino acid sequence of SEQ ID NO: 19, and/or the CDR3 includes amino the amino acid sequence of SEQ ID NO: 20. In further specific non-limiting examples, a) the CDR1 includes the amino acid sequence of SEQ ID NO: 2, the CDR2 includes the amino acid sequence of SEQ ID NO: 3, and the CDR3 includes amino the amino acid sequence of SEQ ID NO: 4; b) the CDR1 includes the amino acid sequence of SEQ ID NO: 6, the CDR2 includes the amino acid sequence of SEQ ID NO: 7, and the CDR3 includes amino the amino acid sequence of SEQ ID NO: 8; c) the CDR1 includes the amino acid sequence of SEQ ID NO: 10, the CDR2 includes the amino acid sequence of SEQ ID NO: 11, and the CDR3 includes amino the amino acid sequence of SEQ ID NO: 12; d) the CDR1 includes the amino acid sequence of SEQ ID NO: 14, the CDR2 includes the amino acid sequence of SEQ ID NO: 15, and the CDR3 includes amino the amino acid sequence of SEQ ID NO: 16; or e) the CDR1 includes the amino acid sequence of SEQ ID NO: 18, the CDR2 includes the amino acid sequence of SEQ ID NO: 19, and the CDR3 includes amino the amino acid sequence of SEQ ID NO: 20.

In some embodiments, the V$_H$H monoclonal antibody or antigen binding fragment includes a heavy chain variable domain comprising an amino acid sequence at least 90%, 91%, 92%, 93%, 94%, 95%, 96%, 97%, 98% or 99% identical to one of SEQ ID NOs: 1, 5, 9, 13, 17, 21, 25, 29, 33, 37, 41, 45, 49, 53, 57, 61, 65, 69, 73, 77, 81 85, 89, 93, 97, 101, 105, 109, and 113, and specifically binds canine PD-1. In specific non-limiting examples, the V$_H$H monoclonal antibody or antigen binding fragment includes a heavy chain variable domain comprising an amino acid sequence at least 90%, 91%, 92%, 93%, 94%, 95%, 96%, 97%, 98% or 99% identical to one of SEQ ID NOs: 1, 5, 9, 13, or 17, and specifically binds canine PD-1.

In further embodiments, a) the CDR1 includes the amino acid sequence of SEQ ID NO: 2, the CDR2 includes the amino acid sequence of SEQ ID NO: 3, and the CDR3 includes amino the amino acid sequence of SEQ ID NO: 4; b) the CDR1 includes the amino acid sequence of SEQ ID NO: 6, the CDR2 includes the amino acid sequence of SEQ ID NO: 7, and the CDR3 includes amino the amino acid sequence of SEQ ID NO: 8; c) the CDR1 includes the amino acid sequence of SEQ ID NO: 10, the CDR2 includes the amino acid sequence of SEQ ID NO: 11, and the CDR3 includes amino the amino acid sequence of SEQ ID NO: 12; d) the CDR1 includes the amino acid sequence of SEQ ID NO: 14, the CDR2 includes the amino acid sequence of SEQ ID NO: 15, and the CDR3 includes amino the amino acid sequence of SEQ ID NO: 16; or e) the CDR1 includes the amino acid sequence of SEQ ID NO: 18, the CDR2 includes the amino acid sequence of SEQ ID NO: 19, and the CDR3 includes amino the amino acid sequence of SEQ ID NO: 20, and the V$_H$H monoclonal antibody or antigen binding fragment includes a heavy chain variable (V$_H$H) domain comprising an amino acid sequence at least 90%, 91%, 92%, 93%, 94%, 95%, 96%, 97%, 98% or 99% identical to a) SEQ ID NO: 1, b) SEQ ID NO: 5; c) SEQ ID NO: 9; d) SEQ ID NO: 13; or e) SEQ ID NO: 17, respectively, and specifically binds canine PD-1. In more embodiments, a) the CDR1 includes the amino acid sequence of SEQ ID NO: 2, the CDR2 includes the amino acid sequence of SEQ ID NO: 3, and the CDR3 includes amino the amino acid sequence of SEQ ID NO: 4; b) the CDR1 includes the amino acid sequence of SEQ ID NO: 6, the CDR2 includes the amino acid sequence of SEQ ID NO: 7, and the CDR3 includes amino the amino acid sequence of SEQ ID NO: 8; c) the CDR1 includes the amino acid sequence of SEQ ID NO: 10, the CDR2 includes the amino acid sequence of SEQ ID NO: 11, and the CDR3 includes amino the amino acid sequence of SEQ ID NO: 12; d) the CDR1 includes the amino acid sequence of SEQ ID NO: 14, the CDR2 includes the amino acid sequence of SEQ ID NO: 15, and the CDR3 includes amino the amino acid sequence of SEQ ID NO: 16; or e) the CDR1 includes the amino acid sequence of SEQ ID NO: 18, the CDR2 includes the amino acid sequence of SEQ ID NO: 19, and the CDR3 includes amino the amino acid sequence of SEQ ID NO: 20, and the, the V$_H$H monoclonal antibody or antigen binding fragment includes a heavy chain variable domain comprising an amino acid sequence at least 95%, 96%, 97%, 98% or 99% identical to a) SEQ ID NO: 1, b) SEQ ID NO: 5; c) SEQ ID NO: 9; d) SEQ ID NO: 13; or e) SEQ ID NO: 17, respectively. In further embodiments, a) the CDR1 includes the amino acid sequence of SEQ ID NO: 2, the CDR2 includes the amino acid sequence of SEQ ID NO: 3, and the CDR3 includes amino the amino acid sequence of SEQ ID NO: 4; b) the CDR1 includes the amino acid sequence of SEQ ID NO: 6, the CDR2 includes the amino acid sequence of SEQ ID NO: 7, and the CDR3 includes amino the amino acid sequence of SEQ ID NO: 8; c) the CDR1 includes the amino acid sequence of SEQ ID NO: 10, the CDR2 includes the amino acid sequence of SEQ ID NO: 11, and the CDR3 includes amino the amino acid sequence of SEQ ID NO: 12; d) the CDR1 includes the amino acid sequence of SEQ ID NO: 14, the CDR2 includes the amino acid sequence of SEQ ID NO: 15, and the CDR3 includes amino the amino acid sequence of SEQ ID NO: 16; or e) the CDR1 includes the amino acid sequence of SEQ ID NO: 18, the CDR2 includes the amino acid sequence of SEQ ID NO: 19, and the CDR3 includes amino the amino acid sequence of SEQ ID NO: 20, and the V$_H$H monoclonal antibody or antigen binding fragment includes a heavy chain variable domain comprising an amino acid sequence at least 98% or 99% identical to a) SEQ ID NO: 1, b) SEQ ID NO: 5; c) SEQ ID NO: 9; d) SEQ ID NO: 13; or e) SEQ ID NO: 17, respectively.

In additional embodiments, the V$_H$H monoclonal antibody or antigen binding fragment includes at most 10, at most 9, at most 8, at most 7, at most 6, at most 5, at most 4, at most 3, at most two or at most one conservative amino acid substitutions in an amino acid sequence of one of SEQ ID NOs: 1, 5, 9, 13, 17, 21, 25, 29, 33, 37, 41, 45, 49, 53, 57, 61, 65, 69, 73, 77, 81 85, 89, 93, 97, 101, 105, 109, and 113, and specifically binds canine PD-1. In specific, non-limiting examples, the heavy chain variable domain or antigen binding fragment includes at most 10, at most 9, at most 8, at most 7, at most 6, at most 5, at most 4, at most 3, at most two or at most one conservative amino acid substitutions in an amino acid sequence set forth as one of SEQ ID NOs: 1, 5, 9, 13, or 17. These V$_H$H monoclonal antibody and antigen binding fragments specifically bind canine PD-1.

In specific non-limiting examples, conservative amino acid substitutions are in the framework regions. Thus, in some embodiments, a) the CDR1 includes the amino acid sequence of SEQ ID NO: 2, the CDR2 includes the amino acid sequence of SEQ ID NO: 3, and the CDR3 includes amino the amino acid sequence of SEQ ID NO: 4; b) the CDR1 includes the amino acid sequence of SEQ ID NO: 6, the CDR2 includes the amino acid sequence of SEQ ID NO: 7, and the CDR3 includes amino the amino acid sequence of SEQ ID NO: 8; c) the CDR1 includes the amino acid sequence of SEQ ID NO: 10, the CDR2 includes the amino acid sequence of SEQ ID NO: 11, and the CDR3 includes amino the amino acid sequence of SEQ ID NO: 12; d) the CDR1 includes the amino acid sequence of SEQ ID NO: 14, the CDR2 includes the amino acid sequence of SEQ ID NO: 15, and the CDR3 includes amino the amino acid sequence of SEQ ID NO: 16; or e) the CDR1 includes the amino acid sequence of SEQ ID NO: 18, the CDR2 includes the amino acid sequence of SEQ ID NO: 19, and the CDR3 includes amino the amino acid sequence of SEQ ID NO: 20; and the V$_H$H monoclonal antibody or antigen binding fragment has a VHH domain with a) SEQ ID NO: 1, b) SEQ ID NO: 5; c) SEQ ID NO: 9; d) SEQ ID NO: 13; ore) SEQ ID NO: 17, respectively, with at most 1, 2, 3, 4, 5, 6, 7, 8, 9, or 10 amino acid substitutions In further embodiments, the V$_H$H monoclonal antibody or antigen binding fragment includes the amino acid sequence of one of SEQ ID NOs: 1, 5, 9, 13, 17, 21, 25, 29, 33, 37, 41, 45, 49, 53, 57, 61, 65, 69, 73, 77, 81 85, 89, 93, 97, 101, 105, 109, and 113. In specific non-limiting examples, the V$_H$H monoclonal antibody or antigen binding fragment includes the amino acid sequence of SEQ ID NOs: 1, 5, 9, 13, or 17.

1. Additional Description of Antibodies and Antigen Binding Fragments

A V$_H$H monoclonal antibody or antigen binding fragment can be a chimeric antibody or antigen binding fragment thereof. The antibody or antigen binding fragment can include any suitable framework region, such as (but not limited to) one or more human framework regions or canine regions. Human framework regions, and mutations that can be made in a human antibody framework region, are known in the art (see, for example, in U.S. Pat. No. 5,585,089, which is incorporated herein by reference). Chimeric antibodies can also include different mammalian region, such as a mouse framework region (See, for example, Jones et al., Nature 321:522, 1986; Riechmann et al., Nature 332:323, 1988; Verhoeyen et al., Science 239:1534, 1988; Carter et al., Proc. Natl. Acad. Sci. U.S.A. 89:4285, 1992; Sandhu, Crit. Rev. Biotech. 12:437, 1992; and Singer et al., J. Immunol. 150:2844, 1993.) Gearing et al., BMC Veterinary Research 9, Article Number 226 (2013) discloses a caninised anti-NGF monoclonal antibody for pain relief in dogs. Exemplary framework regions are disclosed and can be used to produce chimeric antibodies. In some embodiments, one or more of FR1, FR2 and FR3 are canine. In some embodiments, FR1 and FR3 are canine framework regions. In further embodiments, FR2 can be caninised, excluding residues 42, 49 50 and 52. In other embodiments, the FR2 is a llama framework region.

The antibody can be of any isotype. The antibody can be, for example, a V$_H$H IgG antibody. The class of an antibody that specifically binds canine PD-1 can be switched with another. In one aspect, a nucleic acid molecule encoding the V$_H$H domain is isolated using methods well-known in the art, such that it does not include any nucleic acid sequences encoding the constant region. This nucleic acid molecule is then operatively linked to a nucleic acid sequence encoding a C$_H$ from a different class of immunoglobulin molecule, such as a canine constant domain. This can be achieved using a vector or nucleic acid molecule that includes a C$_H$ chain, as known in the art. For example, an antibody that specifically binds canine PD-1 that was originally llama IgG may be class switched.

(a) Binding Affinity

In several embodiments, the V$_H$H monoclonal antibody or antigen binding fragment can specifically bind canine PD-1, such as dog PD-1, with an affinity (e.g., measured by K$_d$) of no more than $1.0 \times 10^{-8}$M, no more than $5.0 \times 10^{-8}$M, no more than $1.0 \times 10^{-9}$M, no more than $5.0 \times 10^{-9}$M, no more than $1.0 \times 10^{-10}$ M, no more than $5.0 \times 10^{-10}$ M, or no more than $1.0 \times 10^{-11}$ M. K$_d$ can be measured, for example, by a radiolabeled antigen binding assay (RIA) performed with the V$_H$H monoclonal antibody and canine PD-1 using known methods. In one assay, solution binding affinity for antigen is measured by equilibrating Fab with a minimal concentration of $^{25}$I)-labeled antigen in the presence of a titration series of unlabeled antigen, then capturing bound antigen with an anti-V$_H$H monoclonal antibody-coated plate (see, e.g., Chen et al., J. Mol. Biol. 293:865-881 (1999)). To establish conditions for the assay, MICROTITER® multi-well plates (Thermo Scientific) are coated overnight with 5 μg/ml of a capturing anti-PD-1 V$_H$H monoclonal antibody in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 μM or 26 pM [$^{125}$I]-antigen are mixed with serial dilutions of a V$_H$H of interest (e.g., consistent with assessment). The V$_H$H monoclonal antibody of interest is then incubated overnight; however, the incubation may continue for a longer period about 65 hours) to ensure that equilibriums is reached. Thereafter, the mixtures are transferred to the capture plate for incubation at room temperature (e.g., for one hour). The solution is then removed, and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each $V_HH$ monoclonal antibody that give less than or equal to 20% of maximal binding are chosen for use in competitive binding assays.

In another assay, $K_d$ can be measured using surface plasmon resonance assays using a BIACORE® D-2000 or a BIACORE®-3000 (BIAcore, Inc., Piscataway, N.J.) at 25° C. with immobilized antigen CMS chips at ~10 response units (RU). Briefly, carboxymethylated dextran biosensor chips (CMS, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µminute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody ($V_HH$ form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

(b) Multispecific Antibodies

In some embodiments, the $V_HM$ monoclonal antibody or antigen binding fragment is included on a multispecific antibody, such as a bi-specific antibody. Such multispecific antibodies can be produced by known methods, such as crosslinking two or more antibodies, antigen binding fragments (such as an scFv) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

In some embodiments, the $V_HH$ monoclonal antibody or antigen binding fragment is included on a bispecific antibody that that specifically binds to canine PD-1 and further specifically binds to a tumor antigen, such as Her-2, or any other tumor antigen. Exemplary tumor antigens are listed below:

Exemplary Tumors and their Tumor Antigens

| Tumor | Tumor Antigens |
|---|---|
| Acute myelogenous leukemia | Wilms tumor 1 (WT1), preferentially expressed antigen of melanoma (PRAME), PR1, proteinase 3, elastase, cathepsin G |
| Chronic myelogenous leukemia | WT1, PRAME, PR1, proteinase 3, elastase, cathepsin G |
| Myelodysplastic syndrome | WT1, PRAME, PR1, proteinase 3, elastase, cathepsin G |
| Acute lymphoblastic leukemia | PRAME |
| Chronic lymphocytic leukemia | Survivin |
| Non-Hodgkin's lymphoma | Survivin |
| Multiple myeloma | New York esophageous 1 (NY-Eso1) |
| Malignant melanoma | MAGE, MART, Tyrosinase, PRAME, GP100 |
| Breast cancer | WT1, herceptin |
| Lung cancer | WT1 |
| Prostate cancer | Prostate-specific antigen (PSA) |
| Colon cancer | Carcinoembryonic antigen (CEA) |
| Renal cell carcinoma (RCC) | Fibroblast growth factor 5 (FGF-5) |

Bispecific forms can also be produced that include two of the $V_HH$ monoclonal antibodies disclosed herein. One type of $V_HH$ antibody is produced by crosslinking two or more $V_HH$ to create bispecific antibodies called diabodies. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

In one embodiment, the bispecific antibody includes a $V_HH$ that specifically binds a first epitope of canine PD-1, wherein the $V_HH$ is covalently linked to a first constant domain; and antigen binding fragment (such as an scFv or $V_HH$) that specifically binds a second epitope of canine PD-1. Any of the $V_HH$ disclosed herein can be included in the bispecific antibody. Exemplary bispecific antibodies are disclosed in the examples section. In one non-limiting example, the bispecific antibody is a diabody.

The $V_HH$ or bispecific antibody can be derivatized or linked to another molecule (such as another peptide or protein). In general, the $V_HH$ or bispecific antibody is derivatized such that the binding to canine PD-1 is not affected adversely by the derivatization or labeling. For example, the $V_HH$ or bispecific antibody can be functionally linked (by chemical coupling, genetic fusion, noncovalent association or otherwise) to one or more other molecular entities, such as another antibody (for example, to form a bispecific antibody), a detection agent, a pharmaceutical agent, and/or a protein or peptide that can mediate association of the $V_HH$ or bispecific antibody with another molecule (such as a streptavidin core region or a polyhistidine tag).

Polypeptides typically contain a variety of functional groups; such as carboxylic acid (COOH), free amine (—NH$_2$) or sulfhydryl (—SH) groups, which are available for reaction with a suitable functional group on a $V_HH$, or a bispecific form thereof, to result in the binding of an effector molecule. Alternatively, the $V_HH$, or bispecific form thereof, can be derivatized to expose or attach additional reactive functional groups. The derivatization may involve attachment of any of a number of linker molecules such as those available from Pierce Chemical Company, Rockford, Ill. The linker can be any molecule used to join the $V_HH$ to another $V_HH$, or to join the $V_HH$ or the bispecific antibody to the effector molecule. In some embodiments, linker is capable of forming covalent bonds to both the V$_H$H (or bispecific form thereof) and to the effector molecule. Suitable linkers are well known to those of skill in the art and include, but are not limited to, straight or branched-chain carbon linkers, heterocyclic carbon linkers, or peptide linkers. Where the V$_H$H and the effector molecule are polypeptides, the linkers may be joined to the constituent amino acids through their side groups (such as through a disulfide linkage to cysteine) or to the alpha carbon amino and carboxyl groups of the terminal amino acids. In fact, similar methods can be used to form a bispecific antibody, such as by attaching to V$_H$H molecules together. Conjugates are further described below.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack, *J. Immunol.*, 158:3965-3970, 1997; Mack, *PNAS*, 92:7021-7025, 1995; Kufer, *Cancer Immunol. Immunother.*, 45:193-197, 1997; Loffler, *Blood*, 95:2098-2103, 2000; and Bruhl, *J. Immunol.*, 166:2420-2426, 2001. Production of bispecific Fab-scFv ("bibody") molecules are described, for example, in Schoonjans et al. (J. Immunol. 165:7050-57, 2000) and Willems et al. (J Chromatogr B Analyt Technol Biomed Life Sci. 786:161-76, 2003). For bibodies, a scFv molecule can be fused to one of the VL-CL (L) or VH-CH1 chains, e.g., to produce a bibody one scFv is fused to the C-term of a Fab chain.

(c) Antigen Binding Fragments

Antigen binding fragments are encompassed by the present disclosure, such as the V$_H$H domain and specifically bind canine PD-1. These antibody fragments retain the ability to selectively bind with the antigen and are "antigen-binding" fragments. In some embodiments, the constant domain is deleted or truncated. In other embodiments, FR4 is truncated or deleted.

In some embodiments, one or more of the CDRs from a disclosed antibody is/are expressed on the surface of another protein, such as a scaffold protein. The expression of domains of antibodies on the surface of a scaffolding protein are known in the art (see e.g. Liu et al., *J. Virology* 85(17): 8467-8476, 2011). Such expression creates a chimeric protein that retains the binding for canine PD-1.

(d) Additional Variants

In certain embodiments, amino acid sequence variants of the V$_H$H monoclonal antibodies and antigen binding fragments provided herein are contemplated. For example, it may be desirable to improve the binding affinity and/or other biological properties of the antibody. Amino acid sequence variants of a V$_H$H monoclonal antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, V$_H$H monoclonal antibody variants having one or more amino acid substitutions are provided. Sites of interest for substitutional mutagenesis include the CDRs and the framework regions. Amino acid substitutions may be introduced into a V$_H$H monoclonal antibody of interest and the products screened for a desired activity, e.g., retained/improved antigen binding to canine PD-1 and/or decreased immunogenicity.

The variants typically retain amino acid residues necessary for correct folding and stabilizing between the regions is the V$_H$H domain and retain the charge characteristics of the residues in order to preserve the low pI and low toxicity of the molecules. Amino acid substitutions can be made in the V$_H$H domain to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In some embodiments, the V$_H$H domain includes up to 10 (such as up to 1, up to 2, up to 3, up to 4, up to 5, up to 6, up to 7, up to 8, or up to 9) amino acid substitutions (such as conservative amino acid substitutions) compared to the amino acid sequence of one of SEQ ID NOs: 1, 5, 9, 13, 17, 21, 25, 29, 33, 37, 41, 45, 49, 53, 57, 61, 65, 69, 73, 77, 81 85, 89, 93, 97, 101, 105, 109, and 113. In some embodiments, the antibody or antigen binding fragment can include up to 10 (such as up to 1, up to 2, up to 3, up to 4, up to 5, up to 6, up to 7, up to 8, or up to 9) amino acid substitutions (such as conservative amino acid substitutions) in the framework regions of the V$_H$H domain, compared to a known framework region, or compared to the framework regions of the antibodies as disclosed herein, and maintain the specific binding activity for canine PD-1

In certain embodiments, substitutions, insertions, or deletions may occur within one or more CDRs so long as such alterations do not substantially reduce the ability of the V$_H$H monoclonal antibody to bind canine PD-1. For example, conservative alterations (e.g., conservative substitutions as provided herein) that do not substantially reduce binding affinity may be made in CDRs. In certain embodiments of the variant the V$_H$H domain sequences provided above, each CDR either is unaltered, or contains no more than one, two or three amino acid substitutions.

To increase binding affinity of the antibody, the V$_H$H domain can be randomly mutated, such as within CDR3 region, in a process analogous to the in vivo somatic mutation process responsible for affinity maturation of antibodies during a natural immune response. Thus in vitro affinity maturation can be accomplished by amplifying V$_H$H domains using PCR primers complementary to the CDR3. In this process, the primers have been "spiked" with a random mixture of the four nucleotide bases at certain positions such that the resultant PCR products encode V$_H$H domain into which random mutations have been introduced. These randomly mutated segments can be tested to determine the binding affinity for canine PD-1. Methods of in vitro affinity maturation are known (see, e.g., Chowdhury, *Methods Mol, Biol.* 207:179-196 (2008)), and Hoogenboom et al. in *Methods in Molecular Biology* 1.78:1-37 (O'Brien et al., ed., Human Press, Totowa, N.J., (2001).)

A useful method for identification of residues or regions of a V$_H$H monoclonal antibody that may be targeted for mutagenesis is called "alanine scanning mutagenesis" as described by Cunningham and Wells (1989) *Science*, 244: 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the $V_HH$ monoclonal antibody with canine PD-1 is affected. Further substitutions may be introduced at the amino acid locations demonstrating functional sensitivity to the initial substitutions. Alternatively, or additionally, a crystal structure of an antigen-$V_HH$ complex is used to identify contact points between the $V_HH$ monoclonal antibody and antigen. Such contact residues and neighboring residues may be targeted or eliminated as candidates for substitution. Variants may be screened to determine whether they contain the desired properties.

In certain embodiments, a $V_HH$ monoclonal antibody provided herein may be further modified to contain additional nonproteinaceous moieties that are known in the art and readily available. The moieties suitable for derivatization of the $V_HH$ monoclonal antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymer is attached, it can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The $V_HH$ monoclonal antibody or antigen binding fragment can be derivatized or linked to another molecule (such as another peptide or protein). In general, the $V_HH$ monoclonal antibody or antigen binding fragment is derivatized such that the binding to canine PD-1 is not affected adversely by the derivatization or labeling. For example, the $V_HH$ monoclonal antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the $V_HF'$ monoclonal antibody or antibody portion with another molecule (such as a streptavidin core region or a polyhistidine tag).

Also included are antibodies that bind to the same epitope on canine PD-1 to which the disclosed antibodies provided herein bind. An antibody "competes" for binding when the competing antibody inhibits canine PD-1 binding of a $V_HH$ monoclonal antibody of the present disclosure by more than 50%, in the presence of competing antibody concentrations higher than $10^6 \times K_D$ of the competing antibody. In a certain embodiment, the antibody that binds to the same epitope on canine PD-1, and is a chimeric antibody.

B. Conjugates

As noted above, the $V_HH$ monoclonal antibodies, or antibody fragments disclosed herein, can be derivatized or linked to another molecule (such as another peptide, protein, enzyme, chromogen or antibody). In general, the derivatization is performed so that binding to canine PD-1 is not affected adversely by the derivatization or labeling. For example, the antibody can be functionally linked, for example, by chemical coupling, genetic fusion, noncovalent association or otherwise to one or more other molecular entities, such as a detection agent and/or a protein or peptide that can mediate associate of the antibody or antibody portion with another molecule (such as a streptavidin core region or a polyhistidine tag).

A $V_HH$ monoclonal antibody, or antigen binding fragment thereof, that specifically binds canine PD-1, can be conjugated to a chemotherapeutic agent or toxin. These conjugates are of use for treating a T cell lymphoma that expresses PD-1 in a canine subject, such as, but not limited to, a dog. One example of a T cell lymphoma that expresses PD-1 is angioimmunoblastic lymphoma. However, any T cell lymphoma that expresses PD-1 can be treated using these conjugates.

Methods that have been reported for attaching a variety of radiodiagnostic compounds, radiotherapeutic compounds, labels (such as enzymes or fluorescent molecules), toxins, and other agents to antibodies and thus a suitable method can be determined for attaching a given agent to an antibody or antigen binding fragment or other polypeptide(s). For example, the antibody or antigen binding fragment can be conjugated with small molecular weight drugs such as Monomethyl Auristatin E (MMAE), Monomethyl Auristatin F (MMAF), maytansine, maytansine derivatives, including the derivative of maytansine known as DM1 (also known as mertansine), or other chemotherapeutic agents to make an antibody drug conjugate (ADC).

Toxins can be employed with a $V_HH$ monoclonal antibody, or antigen binding fragment thereof, that specifically binds canine PD-1. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., *Bio/Technology*, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

In one embodiment, the toxin is *Pseudomonas* exotoxin (PE) (U.S. Pat. No. 5,602,095). As used herein, PE includes full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., J. Biol. Chem. 264:14256-14261, 1989). PE employed with the provided antibodies can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE25, PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pal et al., Proc. Natl. Acad. Sci. USA, 88:3358-3362, 1991; Kondo et al., J. Biol. Chem., 263:9470-9475, 1988; Pastan et al., Biochim. Biophys. Acta, 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., Blood 113(16): 3792-3800, 2009; Onda et al., Proc. Natl. Acad. Sci. USA, 105(32):11311-11316, 2008; and PCT Publication Nos. WO 2007/016150, WO 2009/032954 and WO 2011/032022, which are herein incorporated by reference). The PE variant can be PE25, see Weldon et al., Blood 2009; 113:3792-3800, herein incorporated by reference.

In some examples, the PE is a variant that is resistant to lysosomal degradation, such as PE-LR (Weldon et al., Blood 113(16):3792-3800, 2009; PCT Publication No. WO 2009/032954). In other examples, the PE is a variant designated PE-LR/6X (PCT Publication No. WO 2011/032022). In other examples, the PE is a variant designated PE-LR/8M (PCT Publication No. WO 2011/032022).

Effector molecules and detectable markers can be linked to a $V_H H$ monoclonal antibody, or antigen binding fragment thereof, that specifically binds canine PD-1, by any number of means known to those of skill in the art. Both covalent and non-covalent attachment means may be used. The procedure for attaching an effector molecule or detectable marker to an antibody or antigen binding fragment varies according to the chemical structure of the effector. Polypeptides typically contain a variety of functional groups; such as carboxylic acid (COOH), free amine (—$NH_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the $V_H H$ monoclonal antibody, or antigen binding fragment thereof, and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

Additionally, in several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

A $V_H H$ monoclonal antibody, or antigen binding fragment thereof, that specifically binds canine PD-1, can be labeled with a detectable moiety. Useful detection agents include fluorescent compounds, including fluorescein, fluorescein isothiocyanate, rhodamine, 5-dimethylamine-1-napthalene-sulfonyl chloride, phycoerythrin, lanthanide phosphors, ALEXA FLUOR® and the like. Bioluminescent markers are also of use, such as luciferase, green fluorescent protein (GFP), or yellow fluorescent protein. A $V_H H$ monoclonal antibody, or antigen binding fragment thereof, can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin and detected through indirect measurement of avidin or streptavidin binding. It should be noted that the avidin itself can be labeled with an enzyme or a fluorescent label.

A $V_HH$ monoclonal antibody, or antigen binding fragment thereof, may be labeled with a magnetic agent, such as gadolinium. Antibodies can also be labeled with lanthanides (such as europium and dysprosium), and manganese. Paramagnetic particles, such as superparamagnetic iron oxide, are also of use as labels. An antibody may also be labeled with a predetermined polypeptide epitope recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. Examples of radiolabels include, but are not limited to, the following radioisotopes or radionucleotides: $^3H$, $^{14}C$, $^{15}N$, $^{35}S$, $^{90}Y$, $^{99}Tc$, $^{111}In$, $^{125}I$, $^{131}I$. The radiolabel may be used for both diagnostic purposes.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

C. Polynucleotides and Expression

Nucleic acid molecules encoding the $V_HH$ monoclonal antibodies, antigen binding fragments, and conjugates are provided herein. These nucleic acid molecules can readily be produced by one of skill in the art, using the amino acid sequences provided herein (such as the CDR and $V_HH$ domain sequences), sequences available in the art (such as framework sequences), and the genetic code. One of skill in the art can readily use the genetic code to construct a variety of functionally equivalent nucleic acid molecules, such as nucleic acid molecules which differ in sequence but which encode the same $V_HH$ monoclonal antibody sequence, or encode a conjugate or fusion protein including a $V_HH$ domain.

Nucleic acid molecules encoding the $V_HH$ monoclonal antibodies, antibody binding fragments, and conjugates that specifically bind canine PD-1 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4th ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acid molecules can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In some embodiments, the nucleic acid molecule encoding the $V_HH$ monoclonal antibody, or antigen binding fragment thereof, can be included in a vector (such as a lentiviral vector) for expression in a host cell. The host cell can be prokaryotic or eukaryotic. The nucleic acid molecules can be expressed in a recombinantly engineered cell such as bacteria, plant, yeast, insect and mammalian cells. Methods of expressing and purifying antibodies and antigen binding fragments are known and further described herein (see, e.g., Al-Rubeai (ed), *Antibody Expression and Production*, Springer Press, 2011). Those of skill in the art are knowledgeable in the numerous expression systems available for expression of proteins including *E. coli*, other bacterial hosts, yeast, and various higher eukaryotic cells such as the COS, CHO, HeLa and myeloma cell lines. In some non-limiting examples, nucleic acids encoding a $V_HH$ monoclonal antibody, or antigen binding fragment thereof, a provided that optionally encode a leader sequence.

One or more DNA sequences encoding the $V_HH$ monoclonal antibody, antigen binding fragment thereof, or conjugate thereof, can be expressed in vitro by DNA transfer into a suitable host cell. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding a $V_HH$ monoclonal antibody, antigen binding fragment thereof, or conjugate thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For E. coli, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for E. coli and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

The nucleic acid molecule encoding the antibody, or antigen binding fragment or conjugate thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be co-transformed with polynucleotide sequences encoding the antibody, labeled antibody, or antigen binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

Also provided is a population of cells including at least one host cell described herein. The population of cells can be a heterogeneous population including the host cell including any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population includes mainly host cells (e.g., consisting essentially of) including the recombinant expression vector. The population also can be a clonal population of cells, in which all cells of the population are clones of a single host cell including a recombinant expression vector, such that all cells of the population comprise the recombinant expression vector. In one embodiment of the invention, the population of cells is a clonal population including host cells including a recombinant expression vector as described herein Methods for expression of the $V_HH$ monoclonal antibodies, antigen binding fragments, and conjugates, and/or refolding to an appropriate active form, from mammalian cells, and bacteria such as E. coli have been described and are well-known and are applicable to the antibodies disclosed herein. See, e.g., Harlow and Lane, Antibodies: A Laboratory Manual, $2^{nd}$, Cold Spring Harbor Laboratory, New York, 2013, Simpson ed., Basic methods in Protein Purification and Analysis: A laboratory Manual, Cold Harbor Press, 2008, and Ward et al., Nature 341:544, 1989. Often, functional heterologous proteins from E. coli or other bacteria are isolated from inclusion bodies and require solubilization using strong denaturants, and subsequent refolding. During the solubilization step, as is well known in the art, a reducing agent must be present. An exemplary buffer with a reducing agent is: 0.1 M Tris pH 8, 6 M guanidine, 2 mM EDTA, 0.3 M DTE (dithioerythritol).

In addition to recombinant methods, the $V_HH$ monoclonal antibodies, antigen binding fragments, and conjugates of the present disclosure can also be constructed in whole or in part using standard peptide synthesis well known in the art. Solid phase synthesis of polypeptides can be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

The $V_HH$ monoclonal antibodies, antigen binding fragments, and conjugates can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin.

D. Methods of Detection

Methods are provided for detecting the presence of a canine cell that expresses PD-1 in a canine subject, such as a T cell, for example an exhausted T cell. The subject can be any canine subject, such as, but not limited to, a dog. In some embodiments, the methods include contacting a sample including cells from a subject with one or more of the disclosed $V_HH$ monoclonal antibodies, antigen binding fragments, or conjugates to form an immune complex. The presence (or absence) of the immune complex is then detected. The presence of the immune complex indicates the presence of a cell that expresses canine PD-1 in the subject. The detection methods can involve in vivo detection or in vitro detection of the immune complex. In several embodiments, detection of a cell that expresses canine PD-1 includes detecting cell-surface expression of canine PD-1 on a T cell. In several embodiments of the provided methods, detecting a T cell that expresses canine PD-1 in a subject detects the presence of exhausted T cells. In some embodiments, the sample is obtained from a subject with a tumor, such as an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy.

A variety of formats are of use for detecting a cell that expresses canine PD-1, for example, a T cell that expresses canine PD-1. In some embodiments, a subject is selected who has, is suspected of having, or is at risk of developing, a tumor, for example, an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy.

In one embodiment, a sample is obtained from a subject, and the presence of a T cell that expresses canine PD-1 is assessed in vitro. For example, such methods include contacting a T cell in a biological sample from the subject with one or more of the $V_HH$ monoclonal antibodies, antigen binding fragments or conjugates provided herein that specifically bind canine PD-1 to form an immune complex. The presence (or absence) of the immune complex is then detected. The presence of the immune complex on the cell from the subject indicates the presence of a T cell that expresses PD-1 in the canine subject. For example, an increase in the presence of the immune complex in the sample as compared to formation of the immune complex in a control sample indicates the presence of one or more T cells that express PD-1, such as exhausted T cells, in the canine subject. In some embodiments, a control can be utilized. The control can be a standard value, or a sample from a canine that does not have the tumor.

The biological sample can be any sample, including, but not limited to, blood, blood products, tissue from biopsies, such as from tumors, autopsies and pathology specimens. Biological samples also include sections of tissues, for example, frozen sections taken for histological purposes.

In some examples of the disclosed methods, the $V_HH$ monoclonal antibody or antigen binding fragment thereof is conjugated to a detectable marker. In some examples, the methods further include contacting a second antibody that specifically binds the Vial monoclonal antibody, antigen binding fragment thereof, or a conjugate including these molecules, for a sufficient amount of time to form an immune complex and detecting this immune complex. An increase in the presence of this immune complex in a biological sample from a selected subject (as described above) compared to the presence of the immune complex in a control sample or other standard detects the presence of a T cell that expresses canine PD-1 in the biological sample. In some examples, the second antibody is conjugated to a detectable marker.

Suitable detectable markers for the antibody or secondary antibody are described and known to the skilled artisan. For example, various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

The antibodies that specifically bind canine PD-1 and conjugates thereof can be used in immunohistochemical assays. These assays are well known to one of skill in the art (see Harlow & Lane, *Antibodies, A Laboratory Manual*, 2$^{nd}$ ed., Cold Spring Harbor Publications, New York (2013), for a description of immunoassay formats The antibodies disclosed herein can also be used to detect T cells that express PD-1 vivo. In some examples, methods are disclosed for detecting pathological conditions in a subject. In one embodiment, an effective amount of an antibody that specifically binds to canine PD-1, an antigen binding fragment thereof or a conjugate is administered to the subject for a sufficient amount of time to form an immune complex, which can then be detected. Detection of the immune complex in the subject determines the presence of T cells that express PD-1, such as infiltrating a tumor. In one specific, non-limiting example detection of an immune complex is performed by immunoscintography. Other specific, non-limiting examples of immune complex detection include radiolocalization, radioimaging, magnetic resonance imaging (such as using a biotinylated antibody and avidin-iron oxide), positron emission tomography (such as using an $^{111}$indium-labeled monoclonal antibody) or fluorescence imaging (such as using luciferase or green fluorescent protein labeled antibodies). See Paty et al., *Transplantation.*, 77:1133-1137, 2004, herein incorporated by reference.

In the setting of magnetic resonance imaging, contrast agent detection can be greatly impacted by magnetic resonance scanner field strength. Increased field strengths provide improvements by orders of magnitude in the ability to detect contrast agents (Hu et al., *Ann. Rev. Biomed. Eng.*, 6:157-184, 2004; Wedeking et al., *Magn. Reson. Imaging.*, 17:569-575, 1999). For example, the limit of detection of gadolinium at 2 tesla (T) is ~30 μM. At 4T the limit of detection is reduced to ~1 μM. With newly available 7 to 12T scanners one would expect to detect low (10-100) nM concentrations of this contrast agent. Similar sensitivity can also be identified using contrast agents such as iron oxide.

E. Methods of Treatment

Methods are disclosed for increasing cytotoxic activity of T cells in a canine subject, such as, but not limited to, a dog. In some embodiments, administration of a therapeutically effective amount of the $V_HH$ monoclonal antibody, antigen binding fragment, bispecific antibody, or conjugate (or a nucleic acid encoding these molecules) increases cytotoxic T cell activity in the subject. The subject can have a tumor, such as an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy. Methods are also disclosed for treating these tumors in a canine subject, such as a dog.

In some embodiments, a therapeutically effective amount of a $V_HH$ monoclonal antibody, antigen binding fragment, bispecific antibody, or conjugate (or a nucleic acid encoding these molecules) can be administered to a subject to treat a tumor, such as an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy. In some embodiments, administration of a therapeutically effective amount of the $V_HH$ monoclonal antibody, antigen binding fragment, or conjugate decreases a sign or symptom of the tumor.

In some examples, the $V_HH$ monoclonal antibody, antigen binding fragment, bispecific antibody, or conjugate disclosed herein (or a nucleic acid encoding these molecules) can be administered to a subject to slow or inhibit the growth or metastasis of a tumor, reduce tumor volume and/or reduce metastasis. In these applications, a therapeutically effective amount of the $V_HH$ monoclonal antibody, antigen binding fragment, bispecific antibody, or conjugate (or a nucleic acid encoding these molecules) is administered to a subject in an amount and under conditions sufficient to form an immune complex with canine PD-1, thereby increasing T cell activity, such as cytotoxic T cell activity. Examples of suitable subjects include those diagnosed with or suspecting of having an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy.

The therapeutically effective amount will depend upon the severity of the disease and the general state of the canine subject's health. A therapeutically effective amount is that which provides either subjective relief of a symptom(s) or an objectively identifiable improvement as noted by the clinician or other qualified observer. In one embodiment, a therapeutically effective amount is the amount necessary to inhibit tumor growth, inhibit metastasis, reduce tumor volume, and/or the amount that is effective at reducing a sign or a symptom of the tumor. In other embodiments, a therapeutically effective amount is sufficient to increase cytotoxicity in a canine subject. The therapeutically effective amount of the agents administered can vary depending upon the desired effects and the canine subject to be treated. In some examples, therapeutic amounts are amounts which eliminate or reduce the tumor burden, or which prevent or reduce the proliferation of metastatic cells, or reduce a symptom of the tumor.

Canine subjects can be screened prior to initiating the disclosed therapies, for example to determine whether the canine has a tumor. Thus, these a canine subject can be selected for treatment that has a tumor, such as an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy.

Any method of administration can be used for the a $V_HH$ monoclonal antibody, antigen binding fragment, bispecific antibody, or conjugate, nucleic acid molecules and/or pharmaceutical compositions including these agents, including local and systemic administration. For example, intratumoral, oral, intravascular such as intratumoral, intravenous, intramuscular, intraperitoneal, intranasal, intradermal, intrathecal and subcutaneous administration can be used. In a specific, non-limiting example, intravenous administration is utilized. The particular mode of administration and the dosage regimen will be selected by the attending clinician, taking into account the particulars of the case (for example the subject, the disease, and the disease state involved). In cases in which more than one agent or composition is being administered, one or more routes of administration may be used; for example, a chemotherapeutic agent may be administered orally and a $V_HH$ monoclonal antibody, antigen binding fragment, conjugate, bispecific antibody, or composition including one or more of these agents may be administered intravenously. Methods of administration include injection. In some embodiments, the a $V_HH$ monoclonal antibody, antigen binding fragment, bispecific antibody, or conjugate is provided in a nontoxic pharmaceutically acceptable carrier, such as water, saline, Ringer's solution, dextrose solution, 5% human serum albumin, fixed oils, ethyl oleate, or liposomes. In some embodiments, local administration of the disclosed a $V_HH$ monoclonal antibody, antigen binding fragment, bispecific antibody, or conjugate can be used, for instance by application to a region of tissue from which a tumor has been removed, or a region suspected of being prone to tumor development.

In some embodiments, sustained intra-tumoral (or near-tumoral) release of the pharmaceutical preparation that includes a therapeutically effective amount of the antibody or antigen binding fragment (or conjugate thereof) may be beneficial. In specific non-limiting examples, a slow release formulation or a delivery device is utilized.

The compositions that include a $V_HH$ monoclonal antibody, antigen binding fragment, bispecific antibody, or conjugate (or a nucleic acid encoding these molecules) can be formulated in unit dosage form suitable for individual administration of precise dosages. In addition, the compositions may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s)

over a period of a few days to months, or even years. Thus, the dosage regime will also, at least in part, be determined based on the particular needs of the canine subject to be treated and will be dependent upon the judgment of the administering practitioner, such as a veterinarian.

Typical dosages of the a $V_HH$ monoclonal antibody, antigen binding fragment, or conjugate can range from about 0.01 to about 30 mg/kg, such as from about 0.1 to about 10 mg/kg. In some examples, the dosage is at least about 0.1 mg/kg, at least about 0.2 mg/kg, at least about 0.3 mg/kg, at least about 0.4 mg/kg, at least about 0.5 mg/kg, at least about 1 mg/kg, at least about 4 mg/kg, at least about 3 mg/kg, at least about 5 mg/kg, at least about 6 mg/kg, at least about 7 mg/kg, at least about 8 mg/kg is at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, at least about 20 mg/kg, at least about 21 mg/kg, at least about 22 mg/kg, at least about 23 mg/kg, at least about 24 mg/kg at least about 25 mg/kg, at least about 26 mg/kg, at least about 27 mg/kg, at least about 28 mg/kg, at least about 29 mg/kg, or at least about 30 mg/kg.

In particular examples, the subject is administered a therapeutic composition that includes one or more of the a Vial monoclonal antibody, antigen binding fragment, bispecific antibody, or conjugate on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, a disclosed therapeutic agent is administered may be administered intravenously, subcutaneously or by another mode daily or multiple times per week for a period of time, followed by a period of no treatment, then the cycle is repeated. In some embodiments, the initial period of treatment (e.g., administration of the therapeutic agent daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the therapeutic agent is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

Administration of the a $V_HH$ monoclonal antibody, antigen binding fragment, bispecific antibody, or conjugate, or compositions can be accompanied by administration of other anti-cancer or anti-angiogenesis agents or therapeutic treatments (such as surgical resection of a tumor or radiation therapy). For example, prior to, during, or following administration of a therapeutic amount of the a $V_HH$ monoclonal antibody, antigen binding fragment, bispecific antibody, or conjugate the subject can receive one or more additional therapies. In one example, the subject receives one or more treatments to remove or reduce the tumor. For example, the additional agent may include, but is not limited to, a chemotherapeutic agent, an anti-angiogenic agent, or a combination thereof. In another example, at least part of the tumor is surgically or otherwise excised or reduced in size or volume prior to administering the therapeutically effective amount of the antibody or antigen binding fragment or conjugate.

Particular examples of additional therapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the $V_HH$ monoclonal antibody, antigen binding fragment, or conjugate. Methods and therapeutic dosages of such agents are known to those skilled in the art, and can be determined by a skilled clinician. In one example the chemotherapeutic agent includes 5-FU or IRT or both.

Microtubule binding agent refers to an agent that interacts with tubulin to stabilize or destabilize microtubule formation thereby inhibiting cell division. Examples of microtubule binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264, can be used.

Suitable DNA and RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-FU and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof.

Examples of the commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, IRT (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Thus, non-limiting examples of chemotherapeutic agents for use in combination with the disclosed a $V_HH$ monoclonal antibody, antigen binding fragment, conjugate, and nucleic acid molecules include chemotherapeutic agents such as erlotinib (TARCEVA®, Genentech/OSI Pharm.), bortezomib (VELCADE®, Millenium Pharm.), fulvestrant (FASLODEX®, AstraZeneca), sutent (SU11248, Pfizer), letrozole (FEMARA®, Novartis), imatinib mesylate (GLEEVEC®, Novartis), PTK787/ZK 222584 (Novartis), oxaliplatin (Eloxatin®, Sanofi), 5-FU (5-fluorouracil), leucovorin, Rapamycin (Sirolimus, RAPAMUNE®, Wyeth), lapatinib (TYKERB®, GSK572016, GlaxoSmithKline), lonafarnib (SCH 66336), sorafenib (BAY43-9006, Bayer Labs.), and gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; antifolate antineoplastic such as pemetrexed (ALIMTA® Eli Lilly), aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics, calicheamicin, calicheamicin gamma1I and calicheamicin omega1I; dynemicin, including dynemicin A; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, for example, paclitaxel (TAXOL®, Bristol-Myers Squibb Oncology, Princeton, N.J.), ABRAXANE™ Cremophor-free, albumin, nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylornithine (DMFO); retinoids such as retinoic acid; capecitabine; and pharmaceutically acceptable salts, acids or derivatives of any of the above.

Non-limiting examples of anti-angiogenic agents include molecules, such as proteins, enzymes, polysaccharides, oligonucleotides, DNA, RNA, and recombinant vectors, and small molecules that function to reduce or even inhibit blood vessel growth. Examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thromobospondin, endostatin, thalidomide, and derivatives and analogs thereof. For example, in some embodiments the anti-angiogenesis agent is an antibody that specifically binds to VEGF (for example, AVASTIN®, Roche) or a VEGF receptor (for example, a VEGFR2 antibody). In one example the anti-angiogenic agent includes a VEGFR2 antibody, or DMXAA (also known as Vadimezan or ASA404; available commercially, for example, from Sigma Corp., St. Louis, Mo.) or both. Exemplary kinase inhibitors include GLEEVAC®, IRESSA®, and TARCEVA® that prevent phosphorylation and activation of growth factors. Antibodies that can be used include HERCEPTIN® and AVASTIN® that block growth factors and the angiogenic pathway.

In some examples, the additional agent is a monoclonal antibody, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, sorafenib, sunitinib, Tacatuzumab tetraxetan, Taplitumomab paptox, Tenatumomab, TGN1412, Ticilimumab (=tremelimumab), Tigatuzumab, TNX-650, Trastuzumab, Tremelimumab, Tucotuzumab celmoleukin, Veltuzumab, Volociximab, Votumumab, Zalutumumab.

Another common treatment for some types of tumors is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection. The disclosed compositions can be used in conjunction with surgical resection or with radiation therapy.

Other therapeutic agents, for example anti-tumor agents, that may or may not fall under one or more of the classifications above, also are suitable for administration in combination with the disclosed therapies. By way of example, such agents include adriamycin, apigenin, rapamycin, zebularine, cimetidine, and derivatives and analogs thereof.

Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

G. Compositions

Compositions are provided that include a disclosed $V_HH$ monoclonal antibody, antigen binding fragment, bispecific antibody, conjugate, nucleic acid molecule, or vector in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, an effective amount of the disclosed $V_HH$ monoclonal antibody, antigen binding fragment, conjugate, or nucleic acid molecule, is/are formulated for parenteral administration, such as intravenous administration. Compositions including a disclosed Vial monoclonal antibody, antigen binding fragment, conjugate, bispecific antibody, or nucleic acid molecules as disclosed herein are of use, for example, for the treatment and/or detection of a tumor.

The compositions for administration can include a solution of the disclosed $V_HH$ monoclonal antibody, antigen binding fragments, conjugate, or nucleic acid molecule (or expression vector) in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the active agent in these formulations can vary widely, and will be selected primarily based on fluid volumes, viscosities, body weight and the like in accordance with the particular mode of administration selected and the subject's needs. Actual methods of preparing such dosage forms are known, or will be apparent, to those skilled in the art.

A typical composition including a $V_HH$ monoclonal antibody, antigen binding fragment thereof, bispecific antibody, or conjugate, for intravenous administration includes about 0.01 to about 30 mg/kg per canine subject per day. Actual methods for preparing administrable compositions will be known or apparent to those skilled in the art and are described in more detail in such publications as *Remington's Pharmaceutical Science,* 19th ed., Mack Publishing Company, Easton, Pa. (1995). In some embodiments, the composition can be a liquid formulation including one or more $V_HH$ monoclonal antibodies, antigen binding fragment thereof, or conjugate in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

$V_HH$ monoclonal antibodies, antigen binding fragments, bispecific antibodies, or conjugates may be provided in lyophilized form and rehydrated with sterile water before administration, although they are also provided in sterile solutions of known concentration. The $V_HH$ monoclonal antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of a $V_HH$ monoclonal antibody, antigen binding fragment, bispecific antibody, and a conjugate; for example, antibody drugs have been marketed in the U.S. since the approval of RITUXAN® in 1997. $V_HH$ monoclonal antibodies, antigen binding fragments, bispecific antibodies, and conjugates can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and U.S. Pat. No. 5,534,496).

In some examples, a canine subject is administered the DNA encoding the $V_HH$ monoclonal antibody, antigen binding fragments thereof, bi specific antibody, or conjugate to provide in vivo antibody production, for example using the cellular machinery of the subject. Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids encoding to an organism. The methods include liposomal delivery of the nucleic acids. Such methods can be applied to the production of a $V_HH$ monoclonal antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody, or antibody binding fragments thereof, can be placed under the control of a promoter to increase expression.

In another approach to using nucleic acids, a disclosed antibody, or antibody binding fragments thereof, or bispecific antibody can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (*Bacillus* Calmette Guerin) provides another vector for expression of the disclosed antibodies (see Stover, *Nature* 351:456-460, 1991).

In one embodiment, a nucleic acid encoding a disclosed $V_HH$ monoclonal antibody, or antibody binding fragment thereof, or bispecific antibody, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

F. Kits

Kits are also provided. For example, kits for detecting T cells that express PD-1 in a canine subject, increasing cytotoxic activity in a canine subject, or treating a tumor in a canine subject. The kits will typically include a $V_HH$ monoclonal antibody or antigen binding fragment that specifically binds canine PD-1, a specific antibody, and/or a conjugate thereof.

More than one of the VHH monoclonal antibodies, antigen binding fragments, bispecific antibodies, nucleic acid molecule, or vectors can be included in the kit. Thus, the kit can include two or more $V_HH$ monoclonal antibodies that specifically bind canine PD-1, antigen binding fragments that specifically binds canine PD-1, conjugates thereof, bispecific antibodies, or a combination of these molecules. The kit can also include components for expression in host cells, such as vectors encoding the $V_HH$ monoclonal antibody or antigen binding fragment thereof.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed canine PD-1-specific $V_HH$ monoclonal antibodies, antigen binding fragments, bispecific antibodies or conjugates. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use, for example, in a method of increasing cytotoxic T cell activity, or treating a tumor. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

Nanobodies are small antibody-like molecules (2.5 nm in diameter, and 4.2 nm in length), with a molecular weight of 12-15 kD, which is >10 times smaller than monoclonal antibodies (Arbabi-Gharhroudi, Historical Perspective and Future Outlook. Front Immunol, 2017. 8: p. 1589). Derived from a Heavy Chain-only form of an antibody and naturally produce by camelids (alpaca, llamas and camels) and cartilaginous fishes, nanobodies as a peptide chain of ~110 amino acids exhibit similar target affinity and drug-like targeting properties as monoclonal antibodies (MAbs) (Muyldermans, Nanobodies: natural single-domain antibodies. Annu Rev Biochem, 2013. 82: p. 775-97). Nanobodies are synthesized as only a single heavy chain variable domain ($V_HH$) with three complementarity determining regions (CDRs) that make up the epitope binding portion of the structure. In addition to being small, nanobodies have superior solubility, permeability of tissues and tumors, short plasma half-life and renal elimination (Kijanka et al., Nanomedicine (Lond), 2015. 10(1): p. 161-74; Hassanzadeh-Ghassabeh, et al., Nanomedicine (Lond), 2013. 8(6): p. 1013-26; Sheridan, C., Nat Biotechnol, 2017. 35(12): p. 1115-1117; Steeland, S., et al., Sci Rep, 2017. 7(1): p. 13646; Yan, J., et al., J Transl Med, 2014. 12: p. 343). Furthermore, nanobodies are less immunogenic and will not trigger complement mediated cytotoxicity (Jovcevska and Muyldermans, BioDrugs, 2020. 34(1): p. 11-26; Brahmer, et al., J Clin Oncol, 2010. 28(19): p. 3167-75; Dahan, et al., Cancer Cell, 2015. 28(3): p. 285-95).

Example 1

Antigen-specific immunization of a camelid with a canine PD-1 was used. The vaccination regimen was followed by the construction and antigen selection of a phage display library, that allowed isolation of several individual anti-canine PD-1 reactive phage clones. The nanobody sequences were determined and subcloned to produce recombinant nanobody and analyzed for specificity and affinity to bind to Canine PD-1 protein and inhibition of PD-1 binding to canine PD-L1.

Figure 4:
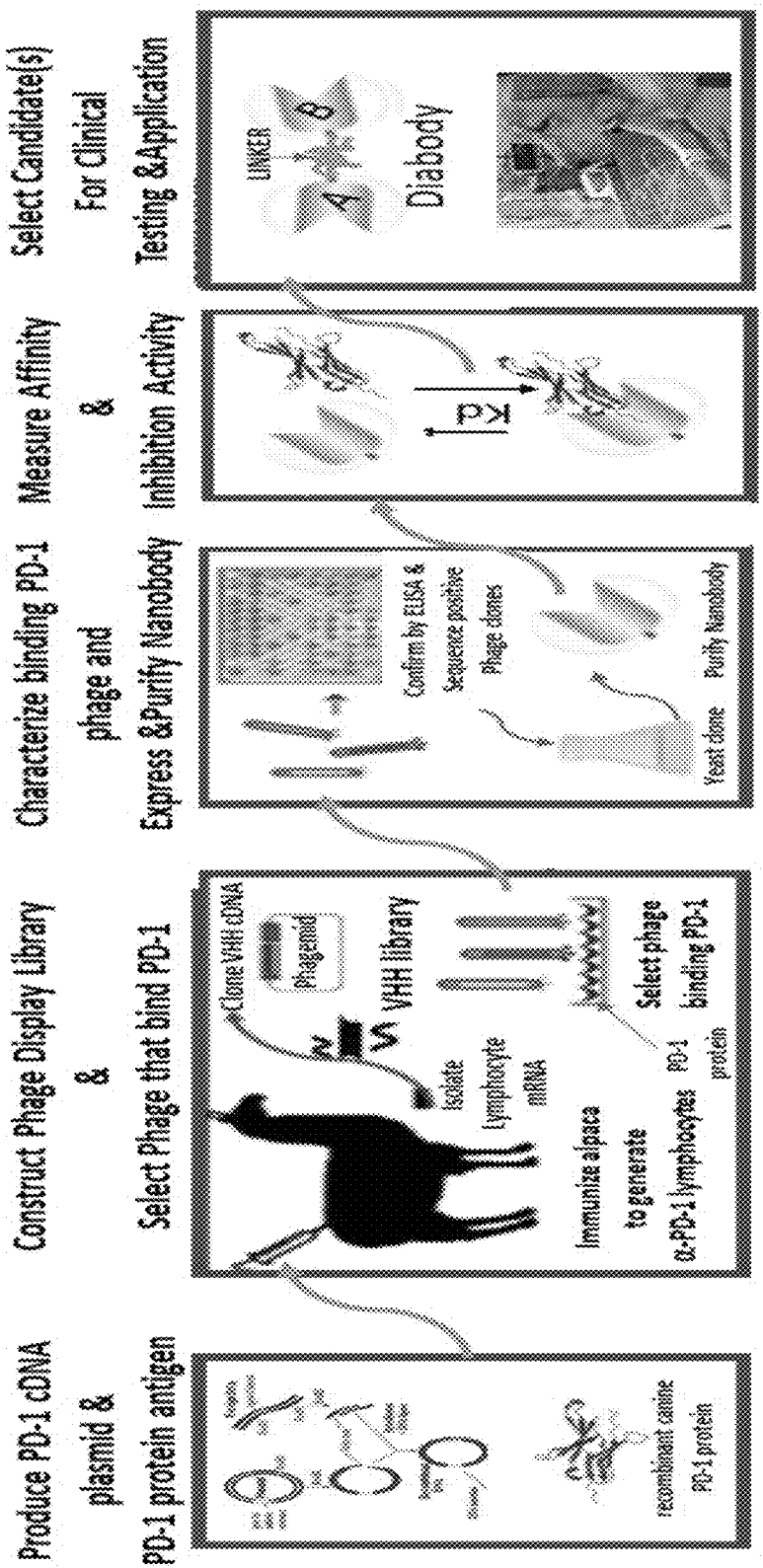
FIG. 4. Process for obtaining the $V_HH$ domains.

Briefly detailed, immunization of an alpaca with a plasmid DNA eukaryotic expression vector construct encoding canine PD-1 cDNA sequence was followed by booster immunizations with adjuvant mixed recombinant purified canine PD-1 protein, see FIG. 4. The canine PD-1 protein was derived from a cultured COS cell line transfected with a canine PD-1 construct. Sero-conversion and nanobody positivity of the animal's response was confirmed by Western blot reactivity to purified canine PD1 protein compared to pre-immune sera (see FIG. 1).

A phage display library was constructed and used to isolate M13 derivative phage clones expressing recombinant nanobody protein fused to the pelB-leader sequence and the pIII tail protein (Hassanzadeh, E et. al, 2010 Antibody Engineering Vol. 2 pp 251-266, Springer-Verlag Berlin Heidelberg R. Kontermann and S. Dubel (eds)). Lymphocytes were isolated from blood taken three days after the final immunization and RNA purified (Qiagen). RNA was converted to double stranded complementary DNA (ds cDNA) and amplified in two rounds of polymerase chain reaction (PCR) with gel size selection and purification steps in between each PCR. The reaction product from final amplification, with Camelid specific ($V_HH$ domain) primers complimentary to the variable heavy chain region of standard antibody and single domain heavy chain nanobody, was fractionated by agarose gel electrophoresis and the lower molecular weight band (~400 base pairs) isolated and purified. The purified material was used to produce a bacterial phagemid (pSEX81 PROGEN) library (Sabir, C R Bio. 337(4): p. 244-9, 2014). This library represented the repertoire of nanobody produced by hyper-immunization of the alpaca with the canine PD-1 antigen. PD-1 binding phage were selected either by: 1) bio-panning on PD-1 expressing COS cells after a round subtractive panning on regular COS cells; and/or 2) three rounds of selection on recombinant canine PD-1 protein coated culture wells. The resulting phagemid encoded sequences were isolated as individual clones and sequenced to determine the single domain antibody (nanobody) protein sequences. At least 30 individual clones were identified and binding to canine PD-1 protein verified and ranked via ELISA binding activity. High activity binders were converted to G-block sequences with optimized codons for bacterial expression and cloned into a pET28 protein expression vector and transformed into BL21 for production and purification of recombinant nanobody protein. High affinity PD-1 binding clones (Kd<10 nanomolar as calculated via ELISA method, Bobrovnik, J. Biochem Biophys Methods. 30; 57(3): p. 213-36) were tested to determine the capacity to block binding of PD-1 to its cognate-ligand recombinant canine PD-L1 (FIG. 2, TABLE 1). Briefly, biotin or nickel coated wells were coated with streptavidin- or His-tagged canine PD-1, respectively, to ensure effective binding. After washing and adding a 2% milk solution to reduce background, candidate nanobodies against canine PD-1 were placed in the wells at various concentrations. For the PD-L1 blocking assay, an equal amount of PD-L1 protein was also added to the well. Detection of candidate nanobody PD-1 binding or blockade of PD-L1 was carried out using antibodies specific for nanobodies or canine PD-L1, respectively. A colorimetric assay with a peroxidase-based enzyme determined candidate nanobody binding affinity to canine PD-1 and blockade of PD-L1 interactions with PD-1. A nonspecific nanobody was included in the assays as a control.

All resulting $V_HH$ monoclonal antibodies demonstrated binding to canine PD-1 protein. However, only five of the nanobodies had a Kd of less than 10 nM, see the table below. Some $V_HH$ monoclonal antibodies were not conclusive as to the binding affinity as they exhibited low expression efficiencies. The following data was obtained.

TABLE 1

| Sequence | Fusion Protein Binds to PD-1 | Protein Expression for Affinity Testing | Binding Affinity Kd (M) | Blocking (50% inhibition) |
|---|---|---|---|---|
| NAN1 | + | Insufficient | TBD | TBD |
| NAN2 | + | Insufficient | TBD | TBD |
| NAN3 | + | Insufficient | TBD | TBD |
| NAN4 | + | Sufficient | $7.00 \times 10^{-9}$ | $8.25 \times 10^{-9}$ M |
| NAN5 | + | Insufficient | TBD | TBD |
| NAN6 | + | Sufficient | $>10 \times 10^{-9}$ * | TBD |
| NAN7/8 | + | Sufficient | $5.01 \times 10^{-9}$ | $6.83 \times 10^{-9}$ M |
| NAN9 | + | Sufficient | $>10 \times 10^{-9}$ * | TBD |
| NAN10 | + | Sufficient | $2.30 \times 10^{-9}$ | $5.04 \times 10^{-9}$ M |
| NAN11 | + | Insufficient | TBD | TBD |
| NAN12 | + | Insufficient | TBD | TBD |
| NAN13/14 | + | Sufficient | $>10 \times 10^{-9}$ * | TBD |
| NAN15 | + | Sufficient | $2.51 \times 10^{-9}$ | $5.0 \times 10^{-9}$ M |
| NAN16 | + | Insufficient | TBD | TBD |
| NAN17/24 | + | Insufficient | TBD | TBD |
| NAN18 | + | Insufficient | TBD | TBD |
| NAN19 | + | Insufficient | TBD | TBD |
| NAN20 | + | Sufficient | $>10 \times 10^{-9}$ * | TBD |
| NAN21 | + | Insufficient | TBD | TBD |
| NAN22 | + | Insufficient | $>10 \times 10^{-9}$ * | TBD |
| NAN23 | + | Insufficient | TBD | TBD |
| NAN25 | + | Insufficient | TBD | TBD |
| NAN26 | + | Insufficient | TBD | TBD |
| NAN27 | + | Sufficient | $>10 \times 10^{-9}$ * | TBD |
| NAN28 | + | Sufficient | $0.95 \times 10^{-9}$ | $9.4 \times 10^{-9}$ M |
| NAN29 | + | Insufficient | TBD | TBD |
| NAN30 | + | Insufficient | TBD | TBD |

* Predicted affinity, not quantitatively measured.
TBD—To Be Determined, further testing required Example 2

Binding to Cellular PD-1

The detection of anti-PD-1 $V_HH$ monoclonal antibody binding to cellular PD-1 is accomplished by using canine PD-1-expressing COS cells. Briefly, a COS cell line was generated by transfecting the full-length canine PD-1 gene. The PD-1-expressing COS cells are incubated with various concentrations of the $V_HH$ monoclonal antibody (0.2-2.0 micrograms) and then anti-camelid/nb antibodies are added, followed by a fluorescent secondary antibody. The cells are interrogated by flow cytometry and PD-1 binding is determined by fluorescence intensity.

The determination of anti-PD-1 $V_HH$ monoclonal antibody-mediated blockade of PD-L1 binding to cellular PD-1 is preformed by adding both anti-PD-1 $V_HH$ monoclonal antibody and recombinant canine PD-L1-human IgG fusion protein to canine PD-1-expressing COS cells, previously described. Detection of bound canine PD-L1 is assessed by flow cytometry following incubation with a fluorescent secondary antibody specific to human IgG. Blockade is determined by a decrease in fluorescence intensity.

Functional effects of canine PD-1 blockade by anti-PD-1 $V_HH$ monoclonal antibody is assessed on canine T-cells in a method previously described (Coy et. Al., Veterinary and comparative oncology, 15(4), pp. 1487-1502, 2017, incorporated herein by reference). Briefly, isolated T-cells from canine blood are activated using the stimulant ConA. Mixtures of anti-PD-1 $V_HH$ monoclonal antibody and recombinant canine PD-L1 are added to the cells, and the cells are incubated for up to 4 days. Supernatants are collected and assayed for the determination of release of IFN-gamma, by ELISA.

Example 3

Clinical Trial

Dogs are selected who have been diagnosed with one or more of an a osteosarcoma, a hemangiosarcoma, a soft tissue sarcoma (fibrosarcoma, peripheral nerve a sheath tumor (eyomyosarcoma, rhabdomayosarcoma, a lymphangiosarcoma, a synovial cell sarcoma, or a myxosarcoma), a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy such as multiple myeloma, B-cell lymphoma, T-cell lymphoma, and chronic and acute lymphocytic leukemia. Dogs are selected for treatment based on samples obtained as tissue biopsies for immunohistochemistry or needle aspirates of the malignant tissues for flow cytometry evaluation. Tissues are then assayed to assess the proportion of PD-L1 expression on the malignant cells surface and the PD1 expression on the tumor or circulating lymphocytes. Complete blood account (CBC) and blood serum chemistry and urine analysis is obtained as a base line prior to each treatment and seven to ten days after the treatment.

One or more $V_HH$ monoclonal antibodies is/are administered intravenous in a dose of 1 µg-10 mg/kg over 30 minutes once every three weeks as long as there is a clinical response and there are no limiting toxicities. In certain patients the composition is administered intra lesional, intrathecal, or intravesical.

Example 4

Bi-Specific Forms

As disclosed above, a method of phage display selection with a library derived from a PD-1 hyperimmunized alpaca was used to isolate thirty individual canine PD-1 reactive phage clones. The nanobody sequences were determined and subcloned to produce individual recombinant nanobodies. Each were analyzed for specificity and affinity to canine PD-1 protein as determined via an enzyme-linked immunosorbent assay (ELISA), see FIG. 4.

Five nanobodies ($V_HH$), based on affinity for PD-1 binding are shown in TABLE 2. Also measured was the ability of each $V_HH$ clone to sterically inhibit canine PD-1 from binding to canine PD-L1, shown as the concentration of nanobody needed to produce a 50% inhibition

TABLE 2

| Clone | Affinity Kd (M) × $10^{-9}$ | 50% Inhibition (M) × $10^{-9}$ |
|---|---|---|
| 1B5 | 0.95 | 0.9 |
| 4B4 | 2.30 | 5.04 |
| 4B2 | 2.51 | 5.0 |
| 5A5 | 5.01 | 6.83 |
| 5A1 | 7.00 | 8.25 |

Activity ranging from 5 to ~10 nanomolar demonstrates functional efficacy as a PD-1 checkpoint inhibitor and thus usefulness for the treatment of canine cancer. In some embodiments, a 25 kg dog requires a dose of 3.5 mg/kg to obtain a theoretical therapeutic inhibition of PD-1/PDL-1. Therefore, approximately 1 gram of drug product would be required over a 2-week course of treatment.

Bivalency, a property of an antibody to bind two sites (epitopes) on a ligand, will increase the strength of binding through a characteristic in immunology termed avidity (see FIG. 5). By combining two different anti-canine PD-1 $V_HH$ that bind to two different epitopes on the same PD-1 molecule, through the process of cooperative binding, there can be additive or synergistic improvement in overall binding affinity. Furthermore, allosteric inhibition of PD-1/PD-L1 interaction can be markedly improved with two epitopes on PD-1 being simultaneously occupied. Thus, with increased affinity and or a more potent inhibition, a significant decrease in the amount of drug needed to provide efficacy can be obtained.

Ten combined pairings of the 5 different anti-canine PD1 nanobodies are tested. The top three are selected, and a "bi-epitope binding" version, also referred as a "diabody" is tested. This is achieved by linking two nano-bodies together with a polypeptide. The binding and blocking activity of these diabody bi-epitope linked antibody pairs is measured using optical biosensor binding assays and in vitro PD-1/PD-1.1 inhibition assays. The following combinations are ranked by highest to lowest blocking activity and functional avidity:

TABLE 3

| Combination | Functional Ranking |
|---|---|
| 4B2 + 4B4 | 1 |
| 4B2 + 5A5 | 2 |
| 4B4 + 5A5 | 3 |
| 4B2 + 5A1 | 4 |
| 4B4 + 5Al | 5 |
| 4B2 + 1B5 | 6 |

TABLE 3-continued

| Combination | Functional Ranking |
|---|---|
| 4B4 + 1B5 | 7 |
| 5A1 + 5A5 | 8 |
| 5A5 + 1B5 | 9 |
| 5A1 + 1B5 | 10 |

Small size and a long serum half-life are two important features for therapeutic applications of biologics. The resident plasma half-life of small protein can be significantly increased by linking to albumin or small peptide domains that bind albumin. Not only does such a modification provide a favorable pharmacological profile, slowing the elimination rate of the diabody, the linking peptide can provide additional steric blocking activity of PD1/PDL-1 interaction increasing the functional efficacy of the drug. Combined, functional benefits from the diabody can lengthen the duration needed between treatments and the amount of drug required for each treatment, thus lowering the cost of a treatment course. The two different linking strategies use either the larger canine albumin protein or smaller albumin binding peptide domain.

a) Measure and compare binding and blocking activity of nanobody pairs. Cellular Binding and Functional Effects of PD-1 nanobody. The detection of PD-1 $V_HH$ (also called nanobody (nb)) or diabody (PD-1 nb/db) binding to cellular PD-1 is accomplished by using canine PD-1-expressing COS cells. A COS cell line was generated by transfecting the full-length canine PD-1 gene. The PD-1-expressing COS cells are incubated with various concentrations of the PD-1 nb/db (0.2-2.0 micrograms) and then anti-camelid/nb antibodies are added, followed by a fluorescent secondary antibody. The cells are interrogated by flow cytometry and PD-1 nb/db binding determined by fluorescence intensity. The determination of PD-1 nb/db-mediated blockade of PD-L1 binding to cellular PD-1 is completed by adding both PD-1 nb/db and recombinant canine PD-L1-human IgG fusion protein to canine PD-1-expressing COS cells. Detection of bound canine PD-L1 is assessed by flow cytometry following incubation with a fluorescent secondary antibody specific to human IgG. Blockade is determined by a decrease in fluorescence intensity. Functional effects of canine PD-1 blockade by PD-1 nb/db is assessed on canine T-cells (Coy et al., Vet Comp Oncol, 2017. 15(4): p. 1487-1502). Briefly, isolated T-cells from canine blood are activated using the stimulant Concanavalin A. To these cells various mixtures of PD-1 nb and recombinant canine PD-L1 are added and the cells incubated for up to 4 days. Supernatants are collected and assayed for the determination of release of IFN-gamma, by ELISA.

b) Vector construction, expression, and purification of anti-PD-1 nanobody and diabody combinations. Production of large amounts of recombinant protein that require proper protein folding and or post translation modification are often facilitated by using yeast expression systems (Mattanovich, et al., Methods Mol Biol, 2012. 824: p. 329-58; Baghban et al., Curr Pharm Biotechnol, 2018. 19(6): p. 451-467). The pPICZα vector construct system from INVIROGEN™ (K1740-01) was used to produce large quantities of our recombinant PD-1nb proteins. Briefly, nanobody sequences were analyzed and optimized for yeast codon usage. G-block synthesis was carried out to insert the sequences into a pPICZα vector. Yeast clones with multiple recombinant genome insertions of the nanobody expression cassette were selected by plating onto increasing amounts of Zeocin antibiotic containing YPDS (yeast extract peptone dextrose) agar plates. Clones were confirmed by RT-PCR screening and nanobody protein production (Protein assay and Coomassie stain SDS-PAGE). Large scale production is done by creating a large biomass of a specific clone grown for 48 hours in a 1 liter shaker culture of Buffered Glycerol Minimal Media containing Histidine. This is inoculated into a 5 liter Chemostat containing Buffered Methanol (0.5%) Complex Media and grown for 7-8 days. Production of the diabody products is done in the same fashion with the vector constructs including a fusion of the two nanobody sequences bridged by canine serum albumin or albumin-binding domain from streptococcal protein G (Nilvebrant and Hober, Comput Struct Biotechnol J, 2013. 6: p. e20130300).

Example 5

Pharmacokinetic (PK), and Tolerability

The pharmacokinetics and tolerability are tested for two individual paired nanobodies targeting two epitopes on canine PD-1, in comparison to the same nanobodies linked by a pseudo albumin linker in one to one ratio (diabody). The study includes 6 male hound dogs, set in two cohorts of three dogs each. Each dog receives a single IV doses of 0.3, 3, or 30 mg/kg of the paired nanobody or the diabody based on their assigned cohort. Changes in body weight, clinical signs, and changes in clinical pathology parameters will be assessed over a period of two weeks after each injection for a total of 49 days (study days-7-42).

Population: Six healthy, adult, male, hound dogs are used. These six dogs are enrolled as two separate cohorts, three dogs are treated with one injection of two nanobodies mixed at equal concentrations, while the other three dogs are treated with linked diabody conformation of these nanobodies.

Procedures and sample collection: All the dogs are managed in accordance with approved animal care and procedural testing guidelines. The dogs are monitored throughout the study period on study days −7, and 1-42 with daily physical examinations, occasional blood pressure measurements, blood works, and urine analysis. Four ml of blood are collected for complete blood count (CBC) and serum biochemistry tests (EDTA tube and additive free tube correspondently) on days −7, 1 (prior to injection) and on days 2, 3, 4, 5, 6, 7 and 14. For the purpose of PK analysis 6 ml of whole blood is collected in serological tube (additive free tube) and is allowed to clot at room temperature for 30 minutes followed by centrifugation (1500 g for 5 min) and separation of the supernatant serum to cryovial tubes. The serum is than stored in −80° C. until analysis. Baseline samples are collected on study day −7 followed by collection on study day 1, prior to injection, every 15 min for the first hour, and on hours 1, 2, 4, 8, and 12 hours after injection (total of 54 ml over the period of 24 hours). Follow up samples for PK analysis are also collected on study days 2, 3, 4, 5, 6, and 7 and 14. This protocol is repeated three times for each of the three dosages, excluding day-7 routine which is done only prior to the first injection. At the end of the 42 days and after all the necessary samples have been collected, the animals are considered "off-study" the presence and concentration of the 4b4 nanobody is detected by liquid chromatography-mass spectrometry (LC-MS). The pharmacokinetic data is analyzed and compared between the two cohorts.

Drug preparation and handling: The formulations are prepared and stored under aseptic conditions, the bi-epitope nanobody pair mixture and Diabody link compounds are suspended in sterile saline at the concentration of 250 mg/ml. This solution is filtered through a 0.2 μm membrane to a sterile vial and stored in −20° C. The catheter placement and administration follow the guidelines for the administration of IV drugs.

Statistical analysis: A commercially available software (GraphPad Prism Version 5.02, GraphPad Software, Inc., La Jolla, Calif., USA) is used to analyze the results. All data is reported as mean±SEM. P values are determined using one-way analysis of variance (ANOVA). For the comparison between the two cohorts and the different concentrations a multivariate analysis of variance (MANOVA) will be used. In the event of significant main effect, Dunnett's post hoc tests will be used to determine the differences between the means at different time points post-nanobody administration in comparison to 0 h baseline. Statistical significance will be defined as $P \leq 0.05$.

After the canine study is completed, the raw data derived from the blood chemistry and plasma levels of drug product is used to determine any dose dependent toxicological indications and effects of the proposed modification on plasma half-life, Cmax, exposure and indications of distribution. These data and data determined in the binding blocking activity studies allow calculation of a theoretical effective dose.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated single heavy chain variable domain (V$_H$H) monoclonal antibody, or an antigen binding fragment thereof, comprising a V$_H$H domain, wherein the V$_H$H domain comprises a complementarity determining region (CDR)1, a CDR2 and a CDR3, and wherein the V$_H$H monoclonal antibody or antigen binding fragment specifically binds a canine programmed death (PD)-1, and wherein
a) the CDR1 comprises the amino acid sequence of SEQ ID NO: 2, the CDR2 comprises the amino acid sequence of SEQ ID NO: 3, and the CDR3 comprises amino the amino acid sequence of SEQ ID NO: 4;
b) the CDR1 comprises the amino acid sequence of SEQ ID NO: 6, the CDR2 comprises the amino acid sequence of SEQ ID NO: 7, and the CDR3 comprises amino the amino acid sequence of SEQ ID NO: 8;
c) the CDR1 comprises the amino acid sequence of SEQ ID NO: 10, the CDR2 comprises the amino acid sequence of SEQ ID NO: 11, and the CDR3 comprises amino the amino acid sequence of SEQ ID NO: 12;
d) the CDR1 comprises the amino acid sequence of SEQ ID NO: 14, the CDR2 comprises the amino acid sequence of SEQ ID NO: 15, and the CDR3 comprises amino the amino acid sequence of SEQ ID NO: 16; or
e) the CDR1 comprises the amino acid sequence of SEQ ID NO: 18, the CDR2 comprises the amino acid sequence of SEQ ID NO: 19, and the CDR3 comprises amino the amino acid sequence of SEQ ID NO: 20.

2. The isolated V$_H$H monoclonal antibody or antigen binding fragment of claim 1, wherein the V$_H$H domain comprises an amino acid sequence at least 90% identical to the amino acid sequence of one of SEQ ID NOs: 1, 5, 9, 13, or 17.

3. The isolated V$_H$H monoclonal antibody or antigen binding fragment of claim 1, comprising the amino acid sequence of one of SEQ ID NOs: 1, 5, 9, 13, or 17.

4. The isolated V$_H$H monoclonal antibody of claim 1, wherein the isolated V$_H$H monoclonal antibody is an IgG.

5. The isolated V$_H$H monoclonal antibody or antigen binding fragment of claim 1, further comprising a heterologous framework region.

6. The isolated V$_H$H monoclonal antibody or antigen binding fragment of claim 5, wherein the heterologous framework region is a canine framework region.

7. The isolated V$_H$H monoclonal antibody or antigen binding fragment of claim 1, further comprising a label.

8. The isolated V$_H$H monoclonal antibody or antigen binding fragment of claim 7, wherein the label is a fluorescent, an enzymatic, or a radioactive label.

9. A pharmaceutical composition comprising the V$_H$H monoclonal antibody or antigen binding fragment of claim 1, or a bispecific antibody comprising the Vial monoclonal antibody or the antigen binding fragment of claim 1, and a pharmaceutically acceptable carrier.

10. An isolated nucleic acid molecule encoding the V$_H$H monoclonal antibody or antigen binding fragment of claim 1.

11. An expression vector comprising the isolated nucleic acid molecule of claim 10 operably linked to a promoter.

12. An isolated host cell transformed with either the nucleic acid molecule of claim 10, or an expression vector comprising the nucleic acid molecule.

13. A method of detecting PD-1 in a biological sample from a canine subject comprising:
contacting a biological sample from the canine subject with at least one V$_H$H monoclonal antibody of claim 1, or the antigen binding fragment thereof; and
detecting antibody bound to the biological sample,
wherein the presence of antibody bound to the sample indicates the presence of T cells expressing PD-1 in the biological sample from the canine subject.

14. The method of claim 13, wherein the at least one V$_H$H monoclonal antibody or antigen binding fragment is labeled.

15. A method of increasing cytotoxic T cell activity in a canine subject, comprising
administering to the canine subject a therapeutically effective amount of a pharmaceutical composition comprising the isolated V$_H$H monoclonal antibody of claim 1 or antigen binding fragment of claim 1 or an expression vector comprising a nucleic acid molecule encoding the isolated V$_H$H monoclonal antibody or antigen binding fragment of claim 1,
thereby increasing cytotoxic T cell activity in the canine subject.

16. The method of claim 15, wherein the canine subject has a tumor.

17. The method of claim 15, wherein the tumor is an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy.

18. The method of claim 16, further comprising administering to the canine subject an effective amount of a chemotherapeutic agent.

19. A method of treating a tumor in a canine subject, comprising,
administering to the canine subject a therapeutically effective amount of a pharmaceutical composition comprising the isolated V$_H$H monoclonal antibody or antigen binding fragment of claim 1 or an expression vector comprising a nucleic acid molecule encoding the isolated V$_H$H monoclonal antibody or antigen binding fragment of claim 1,
thereby treating the tumor in the canine subject.

20. The method of claim 19, wherein the tumor is an osteosarcoma, a hemangiosarcoma, a soft tissue, a head and neck squamous cell carcinoma, a salivary adenocarcinoma, a gastric adenocarcinoma, an intestinal adenocarcinoma, a pancreatic adenocarcinoma, a hepatocellular adenocarcinoma, a biliary carcinoma, a lung adenocarcinoma, a mammary adenocarcinoma, a transitional cell carcinoma, a prostatic carcinoma, melanoma, a histiocytic sarcoma, a mast cell tumor, or a hematologic malignancy.

* * * * *

UNITED STATES PATENT AND TRADEMARK OFFICE
CERTIFICATE OF CORRECTION

Page 1 of 1

PATENT NO. : 11,629,190 B2
APPLICATION NO. : 16/992412
DATED : April 18, 2023
INVENTOR(S) : Mourich et al.

It is certified that error appears in the above-identified patent and that said Letters Patent is hereby corrected as shown below:

In the Claims

Claim 1, Column 121, Lines 54-55, "sequence of SEQ ID NO: 3, and the CDR3 comprises amino the amino acid sequence of SEQ ID NO: 4;" should read -- sequence of SEQ ID NO: 3, and the CDR3 comprises the amino acid sequence of SEQ ID NO: 4 --.

Claim 9, Column 123, Line 6, "1, or a bispecific antibody comprising the Vial monoclonal" should read -- 1, or a bispecific antibody comprising the $V_HH$ monoclonal --.

Signed and Sealed this
Twenty-first Day of November, 2023

Katherine Kelly Vidal
*Director of the United States Patent and Trademark Office*